United States Patent
Franklin

(10) Patent No.: US 9,333,233 B2
(45) Date of Patent: May 10, 2016

(54) METHODS AND COMPOSITIONS FOR THE DELAYED TREATMENT OF STROKE

(71) Applicant: TARIX PHARMACEUTICALS LTD., Cambridge, MA (US)

(72) Inventor: Richard Franklin, Cambridge, MA (US)

(73) Assignee: TARIX PHARMACEUTICALS LTD., Cambridge, MA (US)

(\*) Notice: Subject to any disclaimer, the term of this patent is extended or adjusted under 35 U.S.C. 154(b) by 0 days.

(21) Appl. No.: 14/549,096

(22) Filed: Nov. 20, 2014

(65) Prior Publication Data

US 2015/0238560 A1 Aug. 27, 2015

Related U.S. Application Data

(60) Provisional application No. 61/991,698, filed on May 12, 2014, provisional application No. 61/944,303, filed on Feb. 25, 2014.

(51) Int. Cl.
*A61K 38/08* (2006.01)

(52) U.S. Cl.
CPC ..................... *A61K 38/085* (2013.01)

(58) Field of Classification Search
CPC .................................................. A61K 38/085
See application file for complete search history.

(56) References Cited

U.S. PATENT DOCUMENTS

| | | | |
|---|---|---|---|
| 4,244,946 A | 1/1981 | Rivier et al. |
| 4,305,872 A | 12/1981 | Johnston et al. |
| 4,316,891 A | 2/1982 | Guillemin et al. |
| 5,629,292 A | 5/1997 | Rodgers et al. |
| 5,716,935 A | 2/1998 | Rodgers et al. |
| 5,834,432 A | 11/1998 | Rodgers et al. |
| 5,955,430 A | 9/1999 | Rodgers et al. |
| 6,096,709 A | 8/2000 | Rodgers et al. |
| 6,110,895 A | 8/2000 | Rodgers et al. |
| 6,177,407 B1 | 1/2001 | Rodgers et al. |
| 6,235,766 B1 | 5/2001 | Heitsch et al. |
| 6,239,109 B1 | 5/2001 | Rodgers et al. |
| 6,248,587 B1 | 6/2001 | Rodgers et al. |
| 6,258,778 B1 | 7/2001 | Rodgers et al. |
| 6,335,195 B1 | 1/2002 | Rodgers et al. |
| 6,444,646 B1 | 9/2002 | Rodgers et al. |
| 6,455,500 B1 | 9/2002 | Rodgers et al. |
| 6,475,988 B1 | 11/2002 | Rodgers et al. |
| 6,482,800 B1 | 11/2002 | Rodgers et al. |
| 6,498,138 B1 | 12/2002 | Rodgers et al. |
| 6,566,335 B1 | 5/2003 | Rodgers et al. |
| 6,730,775 B1 | 5/2004 | Rodgers et al. |
| 6,747,008 B1 | 6/2004 | Rodgers et al. |
| 6,762,167 B1 | 7/2004 | Rodgers et al. |
| 6,821,953 B1 | 11/2004 | Rodgers et al. |
| 6,916,783 B2 | 7/2005 | Rodgers et al. |
| 7,118,748 B1 | 10/2006 | Rodgers et al. |
| 7,122,523 B2 | 10/2006 | Rodgers et al. |
| 7,173,011 B2 | 2/2007 | Rodgers et al. |
| 7,176,183 B2 | 2/2007 | Rodgers et al. |
| 7,288,522 B1 | 10/2007 | Rodgers et al. |
| 7,338,938 B2 | 3/2008 | Rodgers et al. |
| 7,744,927 B2 | 6/2010 | Rodgers et al. |
| 7,745,411 B2 | 6/2010 | Rodgers et al. |
| 7,776,828 B2 | 8/2010 | Rodgers et al. |
| 7,786,085 B2 | 8/2010 | Rodgers et al. |
| 8,633,158 B1 | 1/2014 | Franklin |
| 2001/0018449 A1 | 8/2001 | Heitsch et al. |
| 2002/0077344 A1 | 6/2002 | Heitsch et al. |
| 2005/0009893 A1\* | 1/2005 | Schrader ............... A61K 31/00 514/381 |
| 2005/0069533 A1 | 3/2005 | Millan et al. |
| 2008/0312129 A1 | 12/2008 | Souza Dos Santos et al. |
| 2009/0221498 A1 | 9/2009 | Souza Dos Santos et al. |
| 2009/0227507 A1 | 9/2009 | Rodgers et al. |
| 2010/0055146 A1 | 3/2010 | Haas et al. |
| 2010/0316624 A1 | 12/2010 | Loibner et al. |
| 2011/0020315 A1 | 1/2011 | Loibner et al. |
| 2011/0033524 A1 | 2/2011 | Janzek-hawlat et al. |
| 2011/0281805 A1\* | 11/2011 | Walther et al. ............... 514/21.7 |
| 2012/0070403 A1 | 3/2012 | Fisher et al. |
| 2012/0172301 A1 | 7/2012 | Ocaranza Jeraldino et al. |

(Continued)

FOREIGN PATENT DOCUMENTS

| | | |
|---|---|---|
| AU | 723373 B2 | 8/2000 |
| CA | 2205092 A1 | 5/1996 |
| CA | 2221730 A1 | 12/1996 |

(Continued)

OTHER PUBLICATIONS

Mecca et al., "Cerebroprotection by angiotensin-(1-7) in endothelin-1-induced ischaemic stroke", Exp Physiol, 2011, pp. 1084-1096.\*
Mocco et al., "Overexpression of Angiotensin (1-7) In Hematopoietic Stem Cells: A Novel Route of Delivery in Stoke", Presentation No. LB P21, International Stroke Conference, Abstract, pp. 1-4, 2012.\*
Bachem, "H-7424", pp. 1-2; obtained from shop.bachem.com on Apr. 3, 2015.\*
Yonit, "Novel Therapy for the Metabolic Syndrome: Reversibly pegylated Angiotensin 1-7 as a long acting pro-drug", Scientific Council of the Weizmann Institute of Science Rehovot, Israel, 2012, pp. 1-10.\*

(Continued)

*Primary Examiner* — Lianko Garyu
(74) *Attorney, Agent, or Firm* — Choate, Hall & Stewart LLP; Brian E. Reese

(57) ABSTRACT

The present invention provides, among other things, method of treating stroke including a step of administering an angiotensin (1-7) peptide to a subject suffering from a stroke, approximately 24 hours after the stroke. In some embodiments, treatment begins more than 24 hours after the stroke. In some embodiments, administration of an angiotensin (1-7) peptide results in a reduction in the intensity, severity, duration, and/or frequency of at least one symptom or feature of the one or more complications of stroke.

24 Claims, 24 Drawing Sheets

(56) References Cited

U.S. PATENT DOCUMENTS

| | | | |
|---|---|---|---|
| 2013/0210726 A1 | 8/2013 | Franklin | |
| 2013/0237478 A1 | 9/2013 | Franklin | |

FOREIGN PATENT DOCUMENTS

| | | | |
|---|---|---|---|
| CN | 1349530 A | 5/2002 | |
| CN | 100525830 C | 8/2009 | |
| CN | 102164614 A | 8/2011 | |
| EP | 0914828 A2 | 5/1999 | |
| EP | 2163259 A1 | 3/2010 | |
| SU | 1067796 A1 | 1/1986 | |
| WO | WO-95/08565 A1 | 3/1995 | |
| WO | WO-96/14858 A1 | 5/1996 | |
| WO | WO-96/39164 A1 | 12/1996 | |
| WO | WO-98/02452 A2 | 1/1998 | |
| WO | WO-98/26795 A1 | 6/1998 | |
| WO | WO-98/32457 A2 | 7/1998 | |
| WO | WO-99/10205 A1 | 3/1999 | |
| WO | WO-99/26644 A1 | 6/1999 | |
| WO | WO-99/40106 A2 | 8/1999 | |
| WO | WO-99/45945 A1 | 9/1999 | |
| WO | WO-99/46285 A2 | 9/1999 | |
| WO | WO-99/52540 A1 | 10/1999 | |
| WO | WO-00/02905 A2 | 1/2000 | |
| WO | WO-00/09144 A1 | 2/2000 | |
| WO | WO-00/56345 A2 | 9/2000 | |
| WO | WO-01/43761 A2 | 6/2001 | |
| WO | WO-01/44270 A2 | 6/2001 | |
| WO | WO-01/53331 A2 | 7/2001 | |
| WO | WO-01/98325 A1 | 12/2001 | |
| WO | WO-02/087504 A2 | 11/2002 | |
| WO | WO-03/039434 A2 | 5/2003 | |
| WO | WO-2007/000036 A2 | 1/2007 | |
| WO | WO-2009/114461 A2 | 9/2009 | |
| WO | WO-2010/028845 A2 | 3/2010 | |

OTHER PUBLICATIONS

Bachem, "H-2888", pp. 1-2; obtained from shop.bachem.com on Apr. 3, 2015.*
Bennion et al., Abstract W P219: Delivery of an Oral Formulation of Angiotensin-(1-7) After Stroke is Neuroprotective; International Stroke Conference 2014, Feb. 11-13, 2014, pp. 1-2.*
Shahid,The angiotensin-converting enzyme 2—angiotensin-(1-7) axis: the other side of the renin-angiotensin system, Experimental Physiology, 2011, pp. 987-989.*
International Stroke Conference:Final Program, Feb. 11-14, 2014, Title page and p. 64.*
Merriam Webster Dictionary, Definition for the term "start", obtained from http://www.merriam-webster.com/dictionary/start on Nov. 14, 2015; p. 1.*
Benter et al., "Antihypertensive actions of angiotensin-(1-7) in spontaneously hypertensive rats", American Journal of Physiology—Heart and Circulatory Physiology Published Jul. 1, 1995.*
Altschul, S. and Gish, W., Local alignment statistics, Methods in Enzymology, 266:460-480 (1996).
Bodanszky, M. and Sheehan, J. et al., Active esters and resins in peptide synthesis, Chemistry and Industry (London), 38:1597-1598 (1966).
Brady, L. and Dodson, G., Drug design. Reflections on a peptide, Nature 368(6473):692-693 (1994).
Fauchere, J. et al., Association with HeLa cells of *Campylobacter jejuni* and *Campylobacter coli* isolated from human feces, Infection and Immunity, 54(2):283-287 (1986).
Galande, A. et al., Understanding base-assisted desulfurization using a variety of disulfide-bridged peptides, Biopolymers, 71(5):534-551 (2003).
Godeny, M. and Sayeski, P., ANG II-induced cell proliferation is dually mediated by c-Src/Yes/Fyn-regulated ERK1/2 activation in the cytoplasm and PKCzeta-controlled ERK1/2 activity within the nucleus, American Journal of Physiology—Cell Physiology, 291(6):C1297-C1307 (2006).
Hudson, D. et al., Methionine enkephalin and isosteric analogues. I. Synthesis on a phenolic resin support, International Journal of Peptide Protein Research, 14:177-185 (1979).
Jameson, B. et al., A rationally designed CD4 analogue inhibits experimental allergic encephalomyelitis, Nature 368(6473):744-746 (1994).
Kelly-Hayes, M. et al., The American Heart Association Stroke Outcome Classification, Stroke, 29(6):1274-1280 (1998).
Koziarz, P. et al., Reciprocal modulation of the binding of angiotensin agonists and antagonists to angiotensin receptors in smooth muscle, General Pharmacology, 24(3):705-713 (1933).
Merrifield, R.B., Solid Phase Peptide Synthesis, Journal of the American Chemical Society, 85:2149-2154 (1963).
Powell, M. et al., Peptide stability in drug development. II. Effect of single amino acid substitution and glycosylation on peptide reactivity in human serum, Pharmaceutical Research, 10(9):1268-1273 (1993).
Rizo, J. and Gierasch, L., Constrained peptides: models of bioactive peptides and protein substructures, Annual Review of Biochemistry, 61:387-418 (1992).
Sarr, M. et al., Red wine polyphenols prevent angiotensin II-induced hypertension and endothelial dysfunction in rats: role of NADPH oxidase, Cardiovascular Research, 71(4):794-802 (2006).
Saver, Jeffrey L., Time is Brain—Quantified, Stroke, 37(1):263-266 (2006).
Singh, P. et al., Endovascular treatment of acute ischemic stroke, Journal of Neurosciences in Rural Practice, 4(3):298-303 (2013).
Spatola, A. et al., Structure-activity relationships of enkephalins containing serially replaced thiomethylene amide bond surrogates, Life Sciences, 38(14):1243-1249 (1986).
Vale, W. et al., Characterization of a 41-residue ovine hypothalamic peptide that stimulates secretion of corticotropin and beta-endorphin, Science, 213(4514):1394-1397 (1981).
Mocco, J. et al., Overexpression of Angiotensin (1-7) in Hematopoietic Stem Cells: A novel Route of Delivery to Site of Injury in the Brain, International Stroke Conference, pp. 1-8 (2012).
Amaro, S. and Chamorro, A., Translational Stroke Research of the Combination of Thrombolysis and Antioxidant Therapy, Stroke, 42:1495-1499 (2011).
Bealer, S. et al., Anteroventral third ventricle lesions reduce anidiuretic responses to angiotensin II, American Journal of Physiology, 236(6):e610-e615 (1979).
Benter, I. et al., Angiotensin-(1-7) prevents diabetes-induced cardiovascular dysfunction, American Journal of Physiology—Heart Circulatory Physiology, 292:H666-H672 (2007).
Brasnjevic, I. et al., Delivery of peptide and protein drugs over the blood-brain barrier, Progress in Neurobiology, 87(4):212-251 (2009).
Brass, E. et al., Parental therapy with lipo-ecraprost, a lipid-based formulation of a PGEI analog does not alter six-month outcomes in patients with critical leg ischemia, Journal of Vascular Surgery, 43:752-759 (2006).
Chappell, M. et al., Metabolism of angiotensin (1-7) by angiotensin converting enzyme, Hypertension, 31:362-367 (1998).
Ciobica, A. et al., Brain renin-angiotensin system in cognitive function: pre-clinical findings and implications for prevention and treatment of dementia, Acta Neurol. Belg., 109:171-180 (2009).
Clark, M. et al., Angiotensin-(1-7) Downregulates the Angiotensin II Type I Receptor in Vascular Smooth Muscle Cells, Hypertension, 37:1141-1146 (2001).
Dharmani, M. et al., Effects of angiotensin 1-7 on the actions of angiotensin II in the renal and mesenteric vasculature of hypertensive and streptozotocin-induced diabetic rats, European Journal of Pharmacology, Abstract only, 561(1-3):144-150 (2007).
Ebermann L. et al., The angiotensin-(1-7) receptor agonist AVE0991 is cardioprotective in diabetic rats, European Journal of Pharmacology, 590:276-280 (2008).
Extended European Search Report for 13746438.4, 6 pages (Aug. 28, 2015).
Fang H.J. et al., Tissue-specific Pattern of Angiotensin-converting Enzyme 2 Expression in Rat Pancreas, The Journal of International Medical Research, 38:558-569 (2010).

(56) References Cited

OTHER PUBLICATIONS

Ferreira De Lima, G. et al., Structure and Dynamics of Angiotensin (1-7) Vasoactive Peptide in Aqueous Solution at the Density-Functional Based Tight Binding Level, Macromolecular Symposia, 254: 80-86 (2007).
Ford, et al., Pre-Diabetes and the Risk for Cardiovascular Disease, A Systematic Review of the Evidence, Journal of the American College of Cardiology, 55(13):1310-1317 (2010).
Fraga-Silva, R.A. et al., ACE2 Activation Promotes Antithrombotic Activity, Molecular Medcine, 16(5-6):210-215 (2010).
Fraga-Silva, R.A. et al., The Antithrombotic Effect of Angiotensin-(1-7) Involves Mas-Mediated NO Release from Platelets, Journal of Molecular Medicine, 14(1-2):28-35 (2008).
Giani, J. et al., Chronic infusion of angiotensin-(1-7) improves insulin resistance and hypertension induced by high-fructose diet in rats, American Journal of Physiology, Endocrinology and Metabolism, 296(2):E262-E271 (2009).
Hellner, K. et al., Angiotensin (1-7) enhances LTP in the hippocampus through the G-protein-coupled receptor, Molecular and Cellular Neuroscience, 29(3): 427-35 (2005).
International Search Report and Written Opinion for PCT/US13/46429, mailed Jan. 31, 2014.
International Search Report and Written Opinion for PCT/US13/62969, mailed on Jan. 16, 2014.
International Search Report for PCT/US2015/17350, 9 pages (Aug. 5, 2015).
Jiang, T. et al., Suppressing inflammation by inhibiting the Nf-kB pathway contributes to the neuroprotective effect of angiotensin-(1-7) in rats with permanent cerebral ischaemia, British Journal of Pharmacology, 167(7):1520-1532 (2012).
Kluskens, L. et al., Angiotensin (1-7) with thioether bridge: an angiotensin converting enzyme resistant, potent angiotensin (1-7) analog, Journal of Pharmacology Experiment Therapy, 328(3):849-855 (2009).
Le Tourneau, C. et al., Dose escalation methods in phase I cancer clinical trials, Journal of National Cancer Institute, 101:708-720 (2009).
Lee, J. et al., Brain tissue responses to ischemia, The Journal of Clinical Investigation, 106(6):723-731 (2000).
Lu, J. et al., The expression of angiotensin-converting enzyme 2-angiotensin-(1-7)-Mas receptor axis are upregulated after acute cerebral ischemic stroke in rats, Neuropeptides, 47:289-295 (2013).
Machado, R.D.P. et al., Mechanisms of angiotensin-(1-7)-induced inhibition of angiogenesis, American Journal of Physiology—Regulatory, Integrative and Comparative Physiology, 280(4):R994-R1000 (2001).
Marcus, Y., Novel Therapy for the Metabolic Syndrome: Reversibly pegylated Angiotensin 1-7 as a long-acting pro-drug [online] Weizmann Institute of Science (Israel), 108 pages (2010).
Pardridge, W.M., The Blood-Brain Barrier: Bottleneck in Brain Drug Development, Journal of the American Society for Experimental NeuroTherapeutics, 2(1):3-14 (2005).
Pasut, G. et al., Protein, peptide and non-peptide drug PEGylation for therapeutic application, Expert Opinion on Therapeutic Patents, 14:859-894 (2004).
Powell, R. et al., Cellular Therapy with lxmyelocel-T to Treat Critical Limb Ischemia: the Randomized, Double-blind, Placebo-controlled RESTORE-CLI Trial, The American Society of Gene & Cell Therapy, 20(6):1280-1286 (2012).
Prather, W.R. et al., The role of placental derived adherent stromal cell (plx-pad) in the treatment of critical limb ischemi, Cytotherapy, 11(4): 427-434 (2009).
Rabelo, L.A. et al., ACE2-angiotensin-(1-7)-Mas axis and oxidative stress in cardiovascular disease, Hypertension Research, 34(2):154-160, Abstract only (2011).
Regenhardt, R.W. et al., Angiotensin (1-7) has therapeutic potential in hemorrhagic stroke, Physiology, University of Florida, Gainesville, FL, USA, Presentation Abstract No. 1049, May 25-28, 2011.
Regenhardt, R.W. et al., Angiotensin (1-7) reduces cerebral cortical iNOS expression in ischemic stroke: Possible mechanism for cerebroprotection?, Presentation Abstract Program#/Poster#: 658.7/Q9, 40th Annual Meeting Neuroscience 2010, Nov. 16, 2010.
Regenhardt, R.W. et al., Anti-inflammatory effects of angiotensin-(1-7) in ischemic stroke, Neuropharmacology, 71:154-163 (2013).
Regenhardt, R.W., Understanding the Cerebroprotective Actions of the ACE2/ANG-(1-7)Mas Axis During Ischemic and Hemorrhagic Stroke, a dissertation, University of Florida, 146 pages (2012).
Rodgers, K. et al., Accelerated healing of diabetic wound by NorLeu3-angiotensin (1-7), Expert Opinion on Investigational Drugs, 20(11):1575-1781 (2011).
Rodgers, K. et al., Effect of NorLeu3-A(1-7) on scar formation over time after full-thickness incision injury in the rat, Wound Repair and Regeneration, 13(3):309-317 (2005).
Santos, R. et al., Angiotensin-(1-7) is an endogenous ligand for the G protein-coupled receptor Mas, PNAS, 100(14):8258-8263 (2003).
Santos, S. et al., Improved Lipid and Glucoze Metabolism in Transgenic Rats with Increased Circulating Angiotensin-(1-7), Arteriosclerosis, Thrombosis, and Vascular Biology, 30:953-961 (2010).
Siegal, R. et al., Prostaglandin $E_1$ infusion in unstable angina: Effects on anginal frequency and cardiac function, American Heart Journal, 108(4):863-868 (1984).
Soto-Pantoja, D.R. et al., Angiotensin-(1-7) inhibits tumor angiogenesis in human lung cancer xenografts with a reduction in vascular endothelial growth factor, Molecular Cancer Therapeutics, 8(6):1676-1683 (2009).
Suga, H. et al., Suppressive effects of Lipo-$PGE_1$ on intimal hyperplasia after balloon injury in rabbits, The Japanese Journal of Pharmacology, Abstract only, 79(1):173P (1999).
Tamarat, R. et al., Endothelial nitric oxide synthase lies downstream from angiotensin II induced angiogenesis in ischemic hindlimb, Hypertension, 39: 830-835 (2002).
Toton-Zuranska, J. et al., AVE 0991—Angiotensin-(1-7) Receptor Agonist, Inhibits Atherogenesis in Apoe—Knockout Mice, Journal of Physiology and Pharmacology, 61(2):181-183 (2010).
Varagic, J. et al, New angiotensins, Journal of Molecular Medicine, (Berl), 86(6):663-671 (2008).
Written Opinion for PCT/US2015/17350, 5 pages (Aug. 5, 2015).
Xue, H. et al., Counteraction between angiotensin II and angiotensin-(1-7) via activating angiotensin type I and Mas receptor on rat renal mesangial cells, Regulatory Peptides, 177(1-3):12-20 (2012).
Yang, L., Effects of ACE2-Ang(1-7)-Mas Mediated Pancreatic Endothelial Function on Beta Cell Function in Rats, PhD thesis, Huazhong University of Science and Technology (2011).
Zhang, F. et al., Different effects of angiotensin II and angiotensin-(1-7) on vascular smooth muscle cell proliferation and migration, PLoS One, 5(8):e12323 (2010).

* cited by examiner

FIG. 1 Distribution of body weight in the groups during the study

FIG. 2 Neuroscore by group throughout the study

FIG 3 Stepping test by treatment group throughout the study

FIG. 4 Forelimb placement test by treatment group through the study

FIG. 5 Body swing test delta (left turn-right turn) by group throughout the study FIG. 6 Percent change of Vessels Average Diameter in all groups as compared to vehicle control on Day 50

FIG. 7 Percent change of Vessels Average Diameter in all groups as compared to vehicle control on Day 50

FIG. 8 Percent change of Blood Flow in all groups as compared to vehicle control on Day 50

FIG. 9 Percent change in Blood Flow in all groups as compared to vehicle control on Day 50

FIG. 10 Neuroscore for groups 1a and 1b from Day 51 throughout rest of study

FIG. 11 Stepping test for groups treated from Day 51 through the end of the study FIG. 12 Forelimb placement test delta for the groups treated from Day 51 through the end of the study FIG. 13 Body swing test delta (left-right) for groups treated from Day 51 through the study FIG. 14 Percent change of Blood Flow and Vessels Diameter in groups treated from Day 51 on Day 108

```
                        SEQUENCE LISTING

<160> NUMBER OF SEQ ID NOS: 35

<210> SEQ ID NO 1
<211> LENGTH: 7
<212> TYPE: PRT
<213> ORGANISM: Homo sapiens

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Val Ser Ile His Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Val Ser Ile His Cys
1               5

<210> SEQ ID NO 4
<211> LENGTH: 12
<212> TYPE: PRT
<213> ORGANISM: Homo sapiens

<400> SEQUENCE: 4

Asp Arg Val Tyr Ile His Pro Phe His Leu Val Ile
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any amino acid or dicarboxylic acid
<220> FEATURE:
<221> NAME/KEY: MOD_RES
<222> LOCATION: (2)..(2)
<223> OTHER INFORMATION: Arg, Lys, Ala, Cit, Orn, acetylated Ser, Sar,
      D-Arg or D-Lys
<220> FEATURE:
<221> NAME/KEY: MOD_RES
<222> LOCATION: (3)..(3)
<223> OTHER INFORMATION: Val, Ala, Leu, Nle, Ile, Gly, Lys, Pro,
      HydroxyPro, Aib, Acpc or Tyr
<220> FEATURE:
<221> NAME/KEY: MOD_RES
<222> LOCATION: (4)..(4)
<223> OTHER INFORMATION: Tyr, Tyr(PO3), Thr, Ser, homoSer, azaTyr or Ala
<220> FEATURE:
<221> NAME/KEY: MOD_RES
<222> LOCATION: (5)..(5)
<223> OTHER INFORMATION: Ile, Ala, Leu, norLeu, Val or Gly
<220> FEATURE:
<221> NAME/KEY: MOD_RES
<222> LOCATION: (6)..(6)
<223> OTHER INFORMATION: His, Arg or 6-NH2-Phe
<220> FEATURE:
<221> NAME/KEY: MOD_RES
<222> LOCATION: (7)..(7)
<223> OTHER INFORMATION: Cys, Pro or Ala
<220> FEATURE:
<223> OTHER INFORMATION: see specification as filed for detailed
      description of substitutions and preferred embodiments

<400> SEQUENCE: 5

Xaa Xaa Xaa Xaa Xaa Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 6

Asp Arg Leu Tyr Ile His Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Cross link between residues
<220> FEATURE:
<221> NAME/KEY: MOD_RES
<222> LOCATION: (7)..(7)
<223> OTHER INFORMATION: Any cross-linked amino acid

<400> SEQUENCE: 7
```

```
Asp Arg Val Xaa Ile His Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Cross link between residues
<220> FEATURE:
<221> NAME/KEY: MOD_RES
<222> LOCATION: (7)..(7)
<223> OTHER INFORMATION: Any cross-linked amino acid

<400> SEQUENCE: 8

Asp Arg Leu Xaa Ile His Xaa Phe His Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Cross link between residues
<220> FEATURE:
<221> NAME/KEY: MOD_RES
<222> LOCATION: (7)..(7)
<223> OTHER INFORMATION: Any cross-linked amino acid

<400> SEQUENCE: 9

Asp Arg Leu Xaa Ile His Xaa Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
```

```
<223> OTHER INFORMATION: Any cross-linked amino acid
<220> FEATURE:
<221> NAME/KEY: misc_feature
<222> LOCATION: (3)..(6)
<223> OTHER INFORMATION: Cross link between residues
<220> FEATURE:
<221> NAME/KEY: MOD_RES
<222> LOCATION: (6)..(6)
<223> OTHER INFORMATION: Any cross-linked amino acid

<400> SEQUENCE: 10

Arg Leu Xaa Ile His Xaa Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Any cross-linked amino acid
<220> FEATURE:
<221> NAME/KEY: misc_feature
<222> LOCATION: (2)..(5)
<223> OTHER INFORMATION: Cross link between residues
<220> FEATURE:
<221> NAME/KEY: MOD_RES
<222> LOCATION: (5)..(5)
<223> OTHER INFORMATION: Any cross-linked amino acid

<400> SEQUENCE: 11

Leu Xaa Ile His Xaa Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Cross link between residues
<220> FEATURE:
<221> NAME/KEY: MOD_RES
<222> LOCATION: (7)..(7)
<223> OTHER INFORMATION: Any cross-linked amino acid

<400> SEQUENCE: 12

Asp Arg Leu Xaa Ile His Xaa
1               5

<210> SEQ ID NO 13
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Cross link between residues
<220> FEATURE:
<221> NAME/KEY: MOD_RES
<222> LOCATION: (7)..(7)
<223> OTHER INFORMATION: Any cross-linked amino acid

<400> SEQUENCE: 13

Asp Arg Leu Xaa Ile His Xaa Phe His
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any positively-charged amino acid
<220> FEATURE:
<221> NAME/KEY: MOD_RES
<222> LOCATION: (3)..(3)
<223> OTHER INFORMATION: Any aliphatic amino acid
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Thioether bridge between residues
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any cross-linked amino acid

<400> SEQUENCE: 14

Xaa Xaa Xaa Xaa Xaa His Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

<223> OTHER INFORMATION: Abu

<400> SEQUENCE: 15

Asp Arg Val Ala Ile His Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Val Ala Ile His Ala
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (2)..(2)
<223> OTHER INFORMATION: Any positively charged amino acid or absent
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any cross-linked amino acid
<220> FEATURE:
<221> NAME/KEY: misc_feature
<222> LOCATION: (4)..(7)
<223> OTHER INFORMATION: Thioether bridge between residues
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any cross-linked amino acid
<220> FEATURE:
<221> NAME/KEY: MOD_RES
<222> LOCATION: (8)..(8)
<223> OTHER INFORMATION: Any amino acid other than Pro or absent
<220> FEATURE:
<221> NAME/KEY: misc_feature
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Any aliphatic residue or absent
<220> FEATURE:
<223> OTHER INFORMATION: see specification as filed for detailed
      description of substitutions and preferred embodiments

<400> SEQUENCE: 17

Xaa Xaa Leu Xaa Xaa His Xaa Xaa His Xaa
1               5                   10

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 18

Asp Arg Leu Ala Ile His Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 19

Asp Arg Leu Ala Ile His Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 20

Asp Arg Leu Ala Ile His Ala Ile
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 21

Asp Arg Leu Ala Ile His Ala Ile
1               5
```

```
<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Arg Val Tyr Ile His Pro Phe His
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Arg Val Tyr Ile His Pro
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(7)
<223> OTHER INFORMATION: Cross link between residues

<400> SEQUENCE: 24

Asp Arg Val Ser Ile His Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(7)
<223> OTHER INFORMATION: Cross link between residues

<400> SEQUENCE: 25

Ala Arg Val Ser Ile His Cys
1               5

<210> SEQ ID NO 26
<211> LENGTH: 8
<212> TYPE: PRT
<213> ORGANISM: Homo sapiens

<400> SEQUENCE: 26

Asp Arg Val Tyr Ile His Pro Phe
1               5

<210> SEQ ID NO 27
<211> LENGTH: 9
<212> TYPE: PRT
```

<213> ORGANISM: Homo sapiens

<400> SEQUENCE: 27

Asp Arg Val Tyr Ile His Pro Phe His
1               5

<210> SEQ ID NO 28
<211> LENGTH: 10
<212> TYPE: PRT
<213> ORGANISM: Homo sapiens

<400> SEQUENCE: 28

Asp Arg Val Tyr Ile His Pro Phe His Leu
1               5                   10

<210> SEQ ID NO 29
<211> LENGTH: 6
<212> TYPE: PRT
<213> ORGANISM: Homo sapiens

<400> SEQUENCE: 29

Arg Val Tyr Ile His Pro
1               5

<210> SEQ ID NO 30
<211> LENGTH: 7
<212> TYPE: PRT
<213> ORGANISM: Homo sapiens

<400> SEQUENCE: 30

Arg Val Tyr Ile His Pro Phe
1               5

<210> SEQ ID NO 31
<211> LENGTH: 8
<212> TYPE: PRT
<213> ORGANISM: Homo sapiens

<400> SEQUENCE: 31

Arg Val Tyr Ile His Pro Phe His
1               5

<210> SEQ ID NO 32
<211> LENGTH: 9
<212> TYPE: PRT
<213> ORGANISM: Homo sapiens

<400> SEQUENCE: 32

Arg Val Tyr Ile His Pro Phe His Leu
1               5

<210> SEQ ID NO 33
<211> LENGTH: 6
<212> TYPE: PRT
<213> ORGANISM: Homo sapiens

<400> SEQUENCE: 33

Val Tyr Ile His Pro Phe
1               5

<210> SEQ ID NO 34
<211> LENGTH: 7
<212> TYPE: PRT
<213> ORGANISM: Homo sapiens

```
<400> SEQUENCE: 34

Val Tyr Ile His Pro Phe His
1               5

<210> SEQ ID NO 35
<211> LENGTH: 8
<212> TYPE: PRT
<213> ORGANISM: Homo sapiens

<400> SEQUENCE: 35

Val Tyr Ile His Pro Phe His Leu
1               5
```

METHODS AND COMPOSITIONS FOR THE DELAYED TREATMENT OF STROKE

CROSS-REFERENCE TO RELATED APPLICATIONS

This application claims priority to U.S. provisional patent application No. 61/944,303, filed Feb. 25, 2014, and U.S. provisional patent application No. 61/991,698, filed May 12, 2014 the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 15, 2015, is named 2009912-0127_SL.txt and is 11,553 bytes in size.

BACKGROUND

Proper functioning of the central nervous system is essential in any animal. Damage to the central nervous system, and particularly the brain, can have a wide range of physical, cognitive, and behavioral effects, including paralysis, dementia, disruption of proper motor function, and even death. As a result, timely administration of effective treatment is of critical importance. Unfortunately several obstacles often make treatment difficult. One such obstacle is the blood brain barrier, which is a collection of tight junctions between neighboring capillary endothelial cells of the brain. These junctions prevent most substances from crossing unless they are either highly lipophilic or specifically transported across the blood brain barrier. A second obstacle is time itself. Specifically, it is well known that many medical treatments are most effective, or even, in some cases, only effective if administered quickly after injury. In the case of a stroke, for example, this critical period of time is known as the "golden hour". A study by Jeffrey Saver is often referenced in the stroke literature wherein it was estimated that a stroke sufferer loses approximately 1.9 million neurons every minute that the stroke remains untreated (see Saver, J L, Time is Brain—Quantified, 2006, Stroke 37:263-266). This study lead to the often used phrase "time is brain" to describe how rapid administration of therapy is critical to treating the effects of a stroke.

SUMMARY OF THE INVENTION

The present invention is based, in part, on the surprising discovery that angiotensin(1-7) peptides can be used for long term treatment of stroke past the "golden hour," i.e., even days or weeks after the "golden hour" has passed, resulting in the alleviation or amelioration of one or more signs, symptoms, or complications of stroke. This result is particularly surprising since it is well known that as the time from stroke event to treatment increases, outcomes get progressively worse. See, inter alia, Hacke et al., 2004, Association of outcome with early stroke treatment: pooled analysis of ATLANTIS, ECASS and NINDS rt-PA stroke trials, Lancet, 363:768-774. In fact, prior to the present invention, only recombinant tissue plasminogen activator (rt-PA) has been shown to provide significant benefit to stroke sufferers past the "golden hour" and then is "only useful within a period of fewer than 3 or 4.5 hours" (see Singh et al., 2013, Endovascular treatment of acute ischemic stroke, J Neurosci Rural Pract, 4(3): 298-303).

Accordingly, the present invention provides a fundamentally different approach effective for long term treatment of stroke.

Thus, in one aspect, the present application provides methods of treating stroke include a step of administering an angiotensin (1-7) peptide to a subject suffering from a stroke approximately 24 hours after the stroke. In some embodiments, provided methods may include administering an angiotensin (1-7) peptide approximately 25 hours, 30 hours, 36 hours, 42 hours, 48 hours, 72 hours, 96 hours, and/or 120 hours after a stroke. In some embodiments, provided methods may include administration of an angiotensin (1-7) peptide approximately 1 week, 2 weeks, 3 weeks, 4 weeks, 5, weeks, 6 weeks, and/or 7 weeks after the stroke.

In some embodiments, the step of administering an angiotensin (1-7) peptide may be the first treatment of a stroke in a subject. The invention also provides, in some embodiments, administration of an angiotensin (1-7) peptide subsequent to a prior treatment of stroke in a subject. In some embodiments, prior treatment of stroke takes place within 3 hours of a stroke. In some embodiments, the prior treatment of stroke takes place within 12 hours of a stroke.

Various embodiments may be administered via any medically appropriate route. In some embodiments, the administration is via systemic administration. In some embodiments, systemic administration is oral administration. In some embodiments, systemic administration is intravenous administration. In some embodiments, systemic administration is not intracerebroventricular administration.

The treatment of various types of stroke and stroke-related brain conditions are contemplated according to various embodiments, In some embodiments, a stroke is ischemic stroke, hemorrhagic stroke, or a combination thereof In some embodiments, an angiotensin (1-7) peptide is administered at an effective dose periodically at an administration interval such that at least one symptom or feature of stroke is reduced in intensity, severity, duration, or frequency or has delayed onset. In some embodiments, the angiotensin (1-7) peptide is administered once per day. In some embodiments, the angiotensin (1-7) peptide is administered once per week. In some embodiments, the angiotensin (1-7) peptide is administered three times per month. In some embodiments, the angiotensin (1-7) peptide is administered twice per month. In some embodiments, the angiotensin (1-7) peptide is administered once per month.

Any of a variety of doses may be used according to various embodiments. In some embodiments, the angiotensin (1-7) peptide is administered at an effective dose ranging from about 1-1,000 μg/kg/day. In some embodiments, the angiotensin (1-7) peptide is administered at an effective dose ranging from about 50-500 μg/kg/day. In some embodiments, the angiotensin (1-7) peptide is administered at an effective dose ranging from about 1-60 μg/kg/day.

In some embodiments, the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO: 1).

In some embodiments, the angiotensin (1-7) peptide is a functional equivalent of SEQ ID NO: 1. In some embodiments, the functional equivalent is a linear peptide. In some embodiments, the linear peptide comprises a sequence that includes at least four amino acids from the seven amino acids that appear in the naturally-occurring Angiotensin (1-7), wherein the at least four amino acids maintain their relative positions as they appear in the naturally-occurring Angiotensin (1-7). In some embodiments, the linear peptide contains 4-25 amino acids. In some embodiments, the linear peptide is a fragment of the naturally-occurring Angiotensin (1-7). In some embodiments, the linear peptide contains amino acid substitutions, deletions and/or insertions in the naturally-occurring Angiotensin (1-7). In some embodiments, the linear peptide has an amino acid sequence of Asp$^1$-Arg$^2$-Val$^3$-Ser$^4$-Ile$^5$-His$^6$-Cys$^7$ (SEQ ID NO: 2). In some embodiments, the linear peptide has an amino acid sequence of Ala$^1$-Arg$^2$-Val$^3$-Ser$^4$-Ile$^5$-His$^6$-Cys$^7$ (SEQ ID NO: 3). In some embodiments, an angiotensin (1-7) peptide is a non-cyclic peptide.

In some embodiments, the angiotensin (1-7) peptide comprises one or more chemical modifications to increase protease resistance, serum stability and/or bioavailability. In some embodiments, the one or more chemical modifications comprise pegylation.

In some embodiments, the angiotensin (1-7) peptide is a non-peptidic angiotensin(1-7) receptor agonist. In some embodiments, the non-peptidic angiotensin(1-7) receptor agonist is a compound with the following structure:

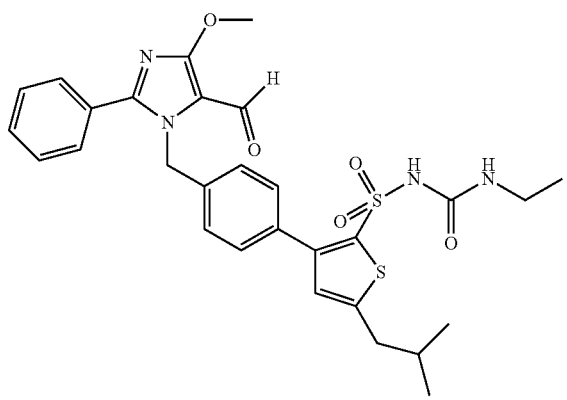 [SMILES: CCNC(=O)NS(=O)(=O)c1sc(CC(C)C)cc1-c1ccc(Cn2c(-c3ccccc3)nc(OC)c2C=O)cc1]

or a pharmaceutically acceptable salt thereof

In some embodiments, administration of an angiotensin (1-7) peptide results in a reduction in the intensity, severity, duration, or frequency of at least one sign, symptom or feature of the one or more complications of stroke. In some embodiments, the one or more complications of stroke is selected from paralysis, memory loss, pain, seizure, dysphagia (difficulty swallowing), aphasia (loss of speech or language ability), dysarthria (difficulty articulating words), ataxia (lack of coordinated movements), depression, mood swings, and loss of vision.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
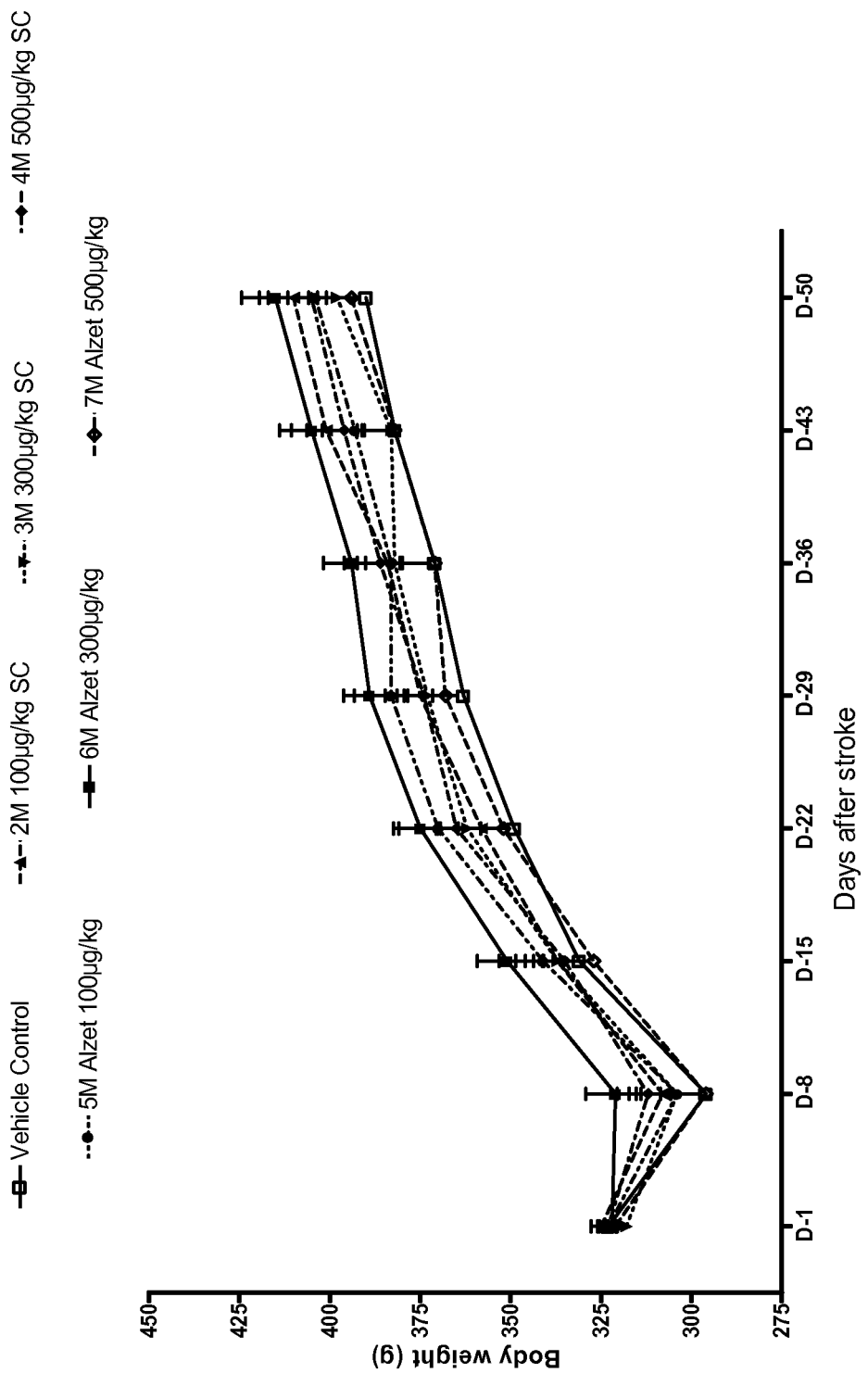
FIG. 1 shows a graph of exemplary body weights in rats exposed to one of: vehicle, 100 μg/kg TXA127 (SEQ ID NO: 1), 300 μg/kg TXA127, 500 μg/kg TXA127, 100 μg/kg TXA127, 300 μg/kg TXA127, or 500 μg/kg TXA127 given either subcutaneously or via continuous infusion (Alzet pump) for up to seven weeks.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Brain Condition—as used herein, a "brain condition" is any disease, disorder or event that results in damage and/or dysfunction of at least a portion of a subject's brain. Non-limiting examples of brain conditions include: stroke (both ischemic and hemorrhagic), vascular dementia, and traumatic brain injury.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Complication: As used herein, the term "complication" refers to an unfavorable evolution of a disease including the development of one or more signs, symptoms or, in some embodiments, even new pathological changes that manifest for a sustained period of time (e.g., weeks, months or years). In some embodiments, complication(s) may include a progression of a sign, symptom or other pathological change, for example, a minor memory loss growing worse over time, or a difficulty with one or more motor functions progressing to paralysis.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., stroke). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., stroke). In some embodiments a reference sample or group of reference samples are from individuals comparable to a particular individual. In some embodiments, relative risk is 0, 1, 2, 3, 4, 5, 6, 7, 8, 9, 10, or more.

Sign: As used herein, the term "sign" refers to a departure from normal body function that indicates the presence of a disease or abnormality that is noticed by a person other than the patient (as opposed to a symptom, see below).

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, ischemic stroke) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Symptom: As used herein, the term "symptom" refers to a departure from normal body function that indicates the presence of a disease or abnormality that is noticed by the subject or patient.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating stroke, including, but not limited to, ischemic and hemorrhagic stroke. In some embodiments, provided methods of treating stroke include a step of administering an angiotensin (1-7) peptide to a subject suffering from a stroke approximately 24 hours after the stroke. In some embodiments, administration occurs 25 hours, 30 hours, 36 hours, 42 hours, 48 hours, 72 hours, 96 hours, or 120 hours after the stroke. In some embodiments, administration occurs 1 week, 2 weeks, 3 weeks, 4 weeks, 5, weeks, 6 weeks, or 7 weeks after the stroke.

The ability of angiotensin(1-7) peptides to treat stroke when administered well after a stroke event, even days or weeks after a stroke is particularly surprising, given the dogma in the art that treatments administered outside this window have limited effectiveness. In particular, the ability of angiotensin (1-7) peptides to treat stroke when administered days or even weeks after the stroke is wholly unexpected as no known stroke therapy has shown such an ability. Accordingly, embodiments of the present invention provide a fundamentally different approach effective for long term treatment of stroke.

Various aspects of the invention are described in detail in the following sections. The use of sections is not meant to limit the invention. Each section can apply to any aspect of the invention. In this application, the use of "or" means "and/or" unless stated otherwise.

Stroke

The brain is highly vulnerable to a disturbance in its oxygen supply. Anoxia and ischemia lasting only a few seconds can cause symptoms and if the condition persists for minutes, they can cause irreversible neuronal damage. Accordingly, stroke is a prominent cause of serious, long-term disability and a leading cause of death in the United States, with 500,000 new or recurrent cases occurring each year (see Kelly-Hayes et al., 1998, The American Heart Association Stroke Outcome Classification, Stroke, 29: 1274-1280). Stroke is also a significant burden on the medical industry, with total health costs for disability due to stroke being estimated at approximately $53 billion annually. Despite its prevalence, the number of available treatments that exist for use during and subsequent to stroke, absent preventative and rehabilitative measures, has remained relatively static and sparse; there are several treatments aimed at preventing initial or subsequent stroke, but few to treat stroke in an interventional and/or acute manner.

There are two major types of stroke: ischemic and hemorrhagic. Ischemic stroke involves an obstruction in one or more blood vessels that supply blood to brain tissue, for example, occlusion resulting from atherosclerotic thrombii, or embolism. Ischemic stroke (cerebral ischemia) represent approximately 88% of all strokes, making ischemic stroke one of the most common types of cerebrovascular injury. Ischemic conditions in the brain quickly lead to neuronal death, often leading to permanent sensorimotor deficits. A hemorrhagic stroke is defined herein as the accumulation of blood anywhere within the cranial vault. Hemorrhagic strokes may result from many causes, including injury resulting from an expanding hematoma, which can disrupt or distort tissue.

A stroke may cause a wide variety of symptoms and/or complications. Without wishing to be held to a particular theory, it is thought that the specific signs, symptoms and/or complications, as well as their severity and duration, may be determined by where the stroke occurs in a brain as well as how severe it is. Because the brain controls or modulates nearly every system in the body, the range of potential signs, symptoms and/or complications is vast. In some embodiments, the signs, symptoms, and/or complications arising from a stroke include one or more of neurological impairment, cognitive impairment, language impairment, emotional impairment (e.g., depression, anxiety), and motor impairment. According to various embodiments, exemplary, non-limiting signs, symptoms and/or complications of stroke include, but are not limited to: paralysis, memory loss, pain, seizure, dysphagia (difficulty swallowing), aphasia (loss of speech or language ability), dysarthria (difficulty articulating words), ataxia (lack of coordinated movements), depression, mood swings, and loss of vision. In some embodiments, paralysis is partial (e.g., limited to one muscle group, area of the body, and/or side of the body). In some embodiments, paralysis is substantially complete (e.g., affecting both sides of the body and most or all voluntary muscles below the neck). Those of skill in the art will be able to readily identify several additional signs, symptoms and/or complications of stroke, the treatment of each of which is contemplated as within the scope of the present invention.

While it can be difficult to accurately catalog every sign, symptom or complication in order to determine an accurate clinical picture of a stroke sufferer, several impairment and rating scales exist to aid medical personnel in determining the proper therapy(ies) for a patient as well as the effectiveness of therapy. Exemplary, non-limiting assessment/rating scales include, but are not limited to: the National Institutes of Health Stroke Scale (NIHSS), the Canadian Neurological Scale, the Middle Cerebral Artery Neurological Score, Guy's Prognostic Score, the American Heart Association's Stroke Outcome Classification (AHA SOC), the Mini-Mental State Examination (MMSE), the Neurobehavioral Cognitive Status Examination (NCSE), the American Speech-Language-Hearing Association Functional Assessment of Communication Skills for Adults, the Boston Diagnostic Aphasia Examination, the Center for Epidemiologic Studies Depression (CES-D) Scale, the Geriatric Depression Scale, the Basic Activities of Daily Living (BADL), the Instrumental Activities of Daily Living (IADL), the Functional Independence Measure (FIM), and the Barthel Index. Those of skill in the art will recognize additional rating scales that may be of use according to some embodiments.

A major barrier in the treatment of both ischemic and hemorrhagic stroke is delivery of a therapeutic that will reach affected tissue. Given the effectiveness of the blood brain barrier, few compounds are capable of crossing into and affecting cerebral tissue. Previously, delivery of compounds such as angiotensin (1-7), had to be made using intracerebroventricular (ICV) delivery. Significantly, embodiments of the present invention, including the exemplary angiotensin (1-7) peptides described below, are able to cross the blood brain barrier without complex delivery systems such as modified stem cells or the like. Rather, in some embodiments, angiotensin (1-7) peptides may be delivered via, inter alia, intravenous or subcutaneous routes.

Despite many medical advancements over the last several decades, the treatment of stroke remains very difficult. Without wishing to be held to a particular theory, factors contributing to the difficulty in treating stroke are thought to include: a) the difficulty in getting therapies to the brain due to the blood-brain-barrier, b) the difficulty in getting a patient treated within the limited window during which previously known therapies have been shown to be effective, and c) the heterogeneity of stroke manifestations which can lead to drastically differing signs, symptoms and/or complications and which may not manifest or become obvious until a significant period of time has passed since the stroke.

Despite the difficulties, several forms of therapy and/or treatment exist for stroke sufferers. One primary form of treatment for ischemic strokes is reperfusion therapy, wherein the clot or other obstruction is targeted for destruction. Recombinant tissue plasminogen activator (rt-PA), also known as a "clot busting" drug, is one of the primary drugs used in this context, though it is known that rt-PA only has a limited time window of 4.5 hours or less during which it has a significant effect, with earlier treatment being correlated with better outcomes (see American Heart Association, Target: Stroke Time Lost is Brain Lost, Target: Stroke Campaign Manual, 2010, available at www.strokeassociation.org/idc/groups/heart-public/@wcm/@hcm/@gwtg/documents/ downloadable/ucm_308277.pdf; see also Singh et al., Endovascular treatment of acute ischemic stroke, 2013, J. Neurosci Rural Pract., 4(3): 298-303).

Additional drugs used in reperfusion therapy include recombinant pro-urokinase, anticoagulants, antiplatelet therapies, and antihypertensives. In some cases, such as when an obstruction is severe enough, or when treatment with one or more drugs is either not appropriate or sufficient, a surgical endovascular procedure is often used. One primary type of surgical therapy is endovascular thrombectomy, in which the clot/thrombus is removed. Exemplary types of endovascular thrombectomy include, but are not limited to: proximal endovascular thrombectomy (e.g., suction thrombectomy) and distal endovascular thrombectomy (e.g., wherein the clot is physically seized and removed from the cerebral vessels). Use of angioplasty, such as balloon angioplasty and/or placement of one or more stents are also common interventional therapies used in certain stroke cases.

Other types of acute interventions include, but may not be limited to, physical removal of clots using modern devices such as the Penumbra or Merci systems or other endovascular approaches to otherwise open, to at least some degree, vessels that may be occluded, partially-occluded, collapsed or otherwise narrowed or closed and to restore, to at least some degree, blood flow to and through the patient, including the area of the infarct. The endovascular approach may include angiography and/or stent-placement. In addition, while these treatments are appropriate for embolic/ischemic-type strokes, they can be contraindicated in the case of hemorrhagic strokes. In the case of hemorrhage, interventional or treatment approaches can include controlling blood pressure, endovascular or surgical approaches to physically repair disrupted vasculature or remove blood clots, or treatment to control any brain swelling and/or aberrant activity resulting from the hemorrhage. Treatment and intervention in stroke remains challenging and persists as an area of unmet need in medicine.

Angiotensin (1-7) Peptides

As used herein, the term "angiotensin (1-7) peptide" refers to both naturally-occurring Angiotensin (1-7) and any functional equivalent, analogue or derivative of naturally-occurring Angiotensin (1-7). As used herein, "peptide" and "polypeptide" are interchangeable terms and refer to two or more amino acids bound together by a peptide bond. As used herein, the terms "peptide" and "polypeptide" include both linear and cyclic peptide. The terms "angiotensin-(1-7)", "Angiotensin-(1-7)", and "Ang-(1-7)" are used interchangeably.

Naturally-Occurring Angiotensin (1-7)

Naturally-occurring Angiotensin (1-7) (also referred to as Ang-(1-7)) is a seven amino acid peptide shown below:

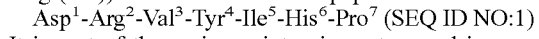
$Asp^1$-$Arg^2$-$Val^3$-$Tyr^4$-$Ile^5$-$His^6$-$Pro^7$ (SEQ ID NO:1)

It is part of the renin-angiotensin system and is converted from a precursor, also known as Angiotensinogen, which is an α-2-globulin that is produced constitutively and released into the circulation mainly by the liver. Angiotensinogen is a member of the serpin family and also known as renin substrate. Human angiotensinogen is 452 amino acids long, but other species have angiotensinogen of varying sizes. Typically, the first 12 amino acids are the most important for angiotensin activity:

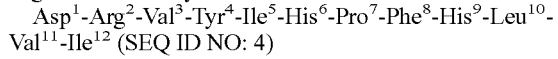
$Asp^1$-$Arg^2$-$Val^3$-$Tyr^4$-$Ile^5$-$His^6$-$Pro^7$-$Phe^8$-$His^9$-$Leu^{10}$-$Val^{11}$-$Ile^{12}$ (SEQ ID NO: 4)

Different types of angiotensin may be formed by the action of various enzymes. For example, Angiotensin (1-7) is generated by action of Angiotensin-converting enzyme 2 (ACE 2).

Ang-(1-7) is an endogenous ligand for Mas receptors. Mas receptors are G-protein coupled receptor containing seven transmembrane spanning regions. As used herein, the term "angiotensin-(1-7) receptor" encompasses the G Protein-Coupled Mas Receptors.

As used herein, the term "naturally-occurring Angiotensin (1-7)" includes any Angiotensin (1-7) peptide purified from natural sources and any recombinantly produced or chemically synthesized peptides that have an amino acid sequence identical to that of the naturally-occurring Angiotensin (1-7).

Functional Equivalents, Analogs or Derivatives of Ang-(1-7)

In some embodiments, an angiotensin (1-7) peptide suitable for the present invention is a functional equivalent of naturally-occurring Ang-(1-7). As used herein, a functional equivalent of naturally-occurring Ang-(1-7) refers to any peptide that shares amino acid sequence identity to the naturally-occurring Ang-(1-7) and retain substantially the same or similar activity as the naturally-occurring Ang-(1-7). For example, in some embodiments, a functional equivalent of naturally-occurring Ang-(1-7) described herein has pro-angiogenic activity as determined using methods described herein or known in the art, or an activity such as nitric oxide release, vasodilation, improved endothelial function, antidiuresis, or one of the other properties discussed herein, that positively impacts angiogenesis. In some embodiments, a functional equivalent of naturally-occurring Ang-(1-7) described herein can bind to or activate an angiotensin-(1-7) receptor (e.g., the G protein-coupled Mas receptor) as determined using various assays described herein or known in the art. In some embodiments, a functional equivalent of Ang-(1-7) is also referred to as an angiotensin (1-7) analogue or derivative, or functional derivative. In some embodiments, a functional equivalent of Ang-(1-7) is a non-cyclic peptide. In some embodiments, a functional equivalent of Ang-(1-7) is not a cyclic peptide with SEQ ID NO: 1. In some embodiments, a functional equivalent of Ang-(1-7) is not a cyclic peptide with SEQ ID NO: 3. In some embodiments, a functional equivalent of Ang-(1-7) is not a cyclic peptide with a 4, 7 thioether bridge.

Typically, a functional equivalent of angiotensin (1-7) shares amino acid sequence similarity to the naturally-occurring Ang-(1-7). In some embodiments, a functional equivalent of Ang-(1-7) according to the invention contains a sequence that includes at least 3 (e.g., at least 4, at least 5, at least 6, at least 7) amino acids from the seven amino acids that appear in the naturally-occurring Ang-(1-7), wherein the at least 3 (e.g., at least 4, at least 5, at least 6, or at least 7) amino acids maintain their relative positions and/or spacing as they appear in the naturally-occurring Ang-(1-7).

In some embodiments, a functional equivalent of Ang-(1-7) may encompass any peptide that contains a sequence at least 50% (e.g., at least 60%, 70%, 80%, or 90%) identical to the amino acid sequence of naturally-occurring Ang-(1-7). Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

In some embodiments, a functional equivalent, analogue or derivative of Ang-(1-7) is a fragment of the naturally-occurring Ang-(1-7). In some embodiments, a functional equivalent, analogue or derivative of Ang-(1-7) contains amino acid substitutions, deletions and/or insertions in the naturally-occurring Ang-(1-7). Ang-(1-7) functional equivalents, analogues or derivatives can be made by altering the amino acid sequences by substitutions, additions, and/or deletions. For example, one or more amino acid residues within the sequence of the naturally-occurring Ang-(1-7) (SEQ ID NO: 1) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophane, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

Examples of Ang-(1-7) functional equivalents, analogues and derivatives are described in the section entitled "Exemplary Angiotensin(1-7) Peptides" below.

An angiotensin-(1-7) peptide can be of any length. In some embodiments, an angiotensin-(1-7) peptide according to the present invention can contain, for example, from 4-25 amino acids (e.g., 4-20, 4-15, 4-14, 4-13, 4-12, 4-11, 4-10, 4-9, 4-8, 4-7 amino acids). In some embodiments, the linear peptide contains 4, 5, 6, 7, 8, 9, 10, 11, 12, 13, 14, 16, 17, 18, 19, 20, 21, 22, 23, 24, or 25 amino acids.

In some embodiments, an angiotensin-(1-7) peptide contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In certain embodiments, an amino acid has the general structure $H_2N$—$C(H)(R)$—$COOH$. In certain embodiments, an amino acid is a naturally-occurring amino acid. In certain embodiments, an amino acid is a synthetic or un-natural amino acid (e.g., α,α-disubstituted amino acids, N-alkyl amino acids); in some embodiments, an amino acid is a d-amino acid; in certain embodiments, an amino acid is an l-amino acid. "Standard amino acid" refers to any of the twenty standard amino acids commonly found in naturally occurring peptides including both l- and d-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to, salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4 (R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In certain embodiments, angiotensin-(1-7) peptides contain one or more L-amino acids, D-amino acids, and/or unnatural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., Infect. Immun. 54:283-287 (1986); Evans et al., J. Med. Chem. 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH$_2$—CH$_2$—, —CH=CH— (cis and trans), —CH$_2$SO—, —CH(OH)CH$_2$—, —COCH$_2$— etc., by methods well known in the art (Spatola, Peptide Backbone Modifications, Vega Data, 1(3):267 (1983); Spatola et al. Life Sci. 38:1243-1249 (1986); Hudson et al. Int. J. Pept. Res. 14:177-185 (1979); and Weinstein. B., 1983, Chemistry and Biochemistry, of Amino Acids, Peptides and Proteins, Weinstein eds, Marcel Dekker, New-York,). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Ang-(1-7) peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Ang-(1-7) peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, J. Am. Chem. Soc. 85: 2149 (1964); Vale et al., Science 213:1394-1397 (1981), in U.S. Pat. Nos. 4,305,872 and 4,316,891, Bodonsky et al. Chem. Ind. (London), 38:1597 (1966); and Pietta and Marshall, Chem. Comm. 650 (1970) by techniques reviewed in Lubell et al. "Peptides" Science of Synthesis 21.11, Chemistry of Amides. Thieme, Stuttgart, 713-809 (2005). The coupling of amino acids to appropriate resins is also well known in the art and has been disclosed in U.S. Pat. No. 4,244,946. (Reviewed in Houver-Weyl, Methods of Organic Chemistry. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., Current Protocols in Molecular Biology, Wiley Interscience, New York, 2001; and Sambrook et al., Molecular Cloning: A Laboratory Manual, 3$^{rd}$ edition, Cold Spring Harbor Laboratory Press, N.Y., 2001.

During any process of the preparation of an Ang-(1-7) peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, Ang-(1-7) peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B.

"Solid-Phase Peptide Synthesis" *Methods in Enzymology*. Vol. 289, Academic Press, 1997).

Alternatively, Ang-(1-7) peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of Ang-(1-7) but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); Jameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include $\alpha,\alpha$-disubstituted amino acids, N-alkyl amino acids, C-$\alpha$-methyl amino acids, $\beta$-amino acids, and $\beta$-methyl amino acids. Amino acids analogs useful in the present invention may include, but are not limited to, $\beta$-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formyl-methionine, 3-methylhistidine and other unconventional amino acids. Furthermore, the synthesis of peptides with non-naturally-occurring amino acids is routine in the art.

In addition, constrained peptides comprising a consensus sequence or a substantially identical consensus sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of naturally-occurring Ang-(1-7) is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; $\alpha$- and $\beta$-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Angiotensin-(1-7) Peptides

In certain aspects, the invention provides non-cyclic (e.g., linear) angiotensin-(1-7) peptides. As discussed above, the structure of naturally-occurring Ang-(1-7) is as follows:

$Asp^1$-$Arg^2$-$Val^3$-$Tyr^4$-$Ile^5$-$His^6$-$Pro^7$ (SEQ ID NO: 1)

The peptides and peptide analogs of the invention can be generally represented by the following sequence:

$Xaa^1$-$Xaa^2$-$Xaa^3$-$Xaa^4$-$Xaa^5$-$Xaa^6$-$Xaa^7$ (SEQ ID NO: 5), or a pharmaceutically acceptable salt thereof.

$Xaa^1$ is any amino acid or a dicarboxylic acid. In certain embodiments, $Xaa^1$ is Asp, Glu, Asn, Acpc (1-aminocyclopentane carboxylic acid), Ala, $Me_2Gly$ (N,N-dimethylglycine), Pro, Bet (betaine, 1-carboxy-N,N,N-trimethylmethanaminium hydroxide), Glu, Gly, Asp, Sar (sarcosine) or Suc (succinic acid). In certain such embodiments, $Xaa^1$ is a negatively-charged amino acid, such as Asp or Glu, typically Asp.

$Xaa^2$ is Arg, Lys, Ala, Cit (citrulline), Orn (ornithine), acetylated Ser, Sar, D-Arg and D-Lys. In certain embodiments, $Xaa^2$ is a positively-charged amino acid such as Arg or Lys, typically Arg.

$Xaa^3$ is Val, Ala, Leu, Nle (norleucine), Ile, Gly, Lys, Pro, HydroxyPro (hydroxyproline), Aib (2-aminoisobutyric acid), Acpc or Tyr. In certain embodiments, $Xaa^3$ is an aliphatic amino acid such as Val, Leu, Ile or Nle, typically Val or Nle.

$Xaa^4$ is Tyr, Tyr($PO_3$), Thr, Ser, homoSer (homoserine), azaTyr (aza-$α^1$-homo-L-tyrosine) or Ala. In certain embodiments, $Xaa^4$ is a hydroxyl-substituted amino acid such as Tyr, Ser or Thr, typically Tyr.

$Xaa^5$ is Ile, Ala, Leu, norLeu, Val or Gly. In certain embodiments, $Xaa^5$ is an aliphatic amino acid such as Val, Leu, Ile or Nle, typically Ile.

$Xaa^6$ is His, Arg or 6-$NH_2$-Phe (6-aminophenylalaine). In certain embodiments, $Xaa^6$ is a fully or partially positively-charged amino acid such as Arg or His.

$Xaa^7$ is Cys, Pro or Ala.

In certain embodiments, one or more of $Xaa^1$-$Xaa^7$ is identical to the corresponding amino acid in naturally-occurring Ang-(1-7). In certain such embodiments, all but one or two of $Xaa^1$-$Xaa^7$ are identical to the corresponding amino acid in naturally-occurring Ang-(1-7). In other embodiments, all of $Xaa^1$-$Xaa^6$ are identical to the corresponding amino acid in naturally-occurring Ang-(1-7).

In certain embodiments, $Xaa^3$ is Nle. When $Xaa^3$ is Nle, one or more of $Xaa^1$-$Xaa^2$ and $Xaa^{4-7}$ are optionally identical to the corresponding amino acid in naturally-occurring Ang-(1-7). In certain such embodiments, all but one or two of $Xaa^1$-$Xaa^2$ and $Xaa^{4-7}$ are identical to the corresponding amino acid in naturally-occurring Ang-(1-7). In other embodiments, all of $Xaa^1$-$Xaa^2$ and $Xaa^{4-7}$ are identical to the corresponding amino acid in naturally-occurring Ang-(1-7), resulting in the amino acid sequence: $Asp^1$-$Arg^2$-$Nle^3$-$Tyr^4$-$Ile^5$-$His^6$-$Pro^7$ (SEQ ID NO: 6).

In certain embodiments, the peptide has the amino acid sequence $Asp^1$-$Arg^2$-$Val^3$-$Ser^4$-$Ile^5$-$His^6$-$Cys^7$ (SEQ ID NO: 2) or $Ala^1$-$Arg^2$-$Val^3$-$Ser^4$-$Ile^5$-$His^6$-$Cys^7$ (SEQ ID NO: 3).

In some embodiments, a linear angiotensin (1-7) peptide as described herein is a peptide having a sequence of $Asp^1$-$Arg^2$-$Val^3$-$Tyr^4$-$Ile^5$-$His^6$-$Pro^7$-$Phe^8$-$His^9$ (SEQ ID NO: 22), which is identical to the sequence of Ang(1-9). In some embodiments, an angiotensin (1-7) peptide is a derivative of Ang (1-9). For exemplary Ang (1-9) peptides, including Ang(1-9) derivatives, see U.S. Patent Publication 2012/0172301, the disclosure of which is hereby incorporated by reference.

In some embodiments, a linear angiotensin (1-7) peptide is a peptide with an amino acid sequence of Ala$^1$-Arg$^2$-Val$^3$-Tyr$^4$-Ile$^5$-His$^6$-Pro$^7$ (SEQ ID NO: 23). Additional sequences derived from SEQ ID NO: 23 may be found in European Patent Application 2,264,048, the disclosure of which is hereby incorporated by reference.

Exemplary Cyclic Angiotensin (1-7) Peptides

In certain aspects, the invention provides cyclic angiotensin-(1-7) peptide analogs comprising a linkage, such as between the side chains of amino acids corresponding to positions Tyr$^4$ and Pro$^7$ in Ang. These peptide analogs typically comprise 7 amino acid residues, but can also include a cleavable sequence. As discussed in greater detail below, the invention includes fragments and analogs where one or more amino acids are substituted by another amino acid (including fragments). One example of such an analog is Asp$^2$-Arg$^2$-Val$^3$-Ser$^4$-Ile$^5$-His$^6$-Cys$^7$(SEQ ID NO: 24), wherein a linkage is formed between Ser$^4$ and Cys$^7$. Another example of such an analog is Ala$^1$-Arg$^2$-Val$^3$-Ser$^4$-Ile$^5$-His$^6$-Cys$^7$ (SEQ ID NO: 25), wherein a linkage is formed between Ser$^4$ and Cys$^7$. In some embodiments, a cyclic angiotensin (1-7) peptide analog is a cyclic analog that does not have a sequence according to SEQ ID NO: 1. In some embodiments, a cyclic angiotensin (1-7) peptide analog is a cyclic analog that does not have a sequence according to SEQ ID NO: 2. In some embodiments, a cyclic angiotensin (1-7) peptide analog is a cyclic analog that does not have a sequence according to SEQ ID NO: 3.

Although the following section describes aspects of the invention in terms of a thioether bond linking residues at the 4- and 7-positions, it should be understood that other linkages (as described above) could replace the thioether bridge and that other residues could be cyclized. A thioether bridge is also referred to as a monosulfide bridge or, in the case of Ala-S-Ala, as a lanthionine bridge. Thioether bridge-containing peptides can be formed by two amino acids having one of the following formulas:

Formula (I)

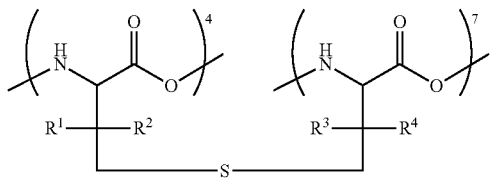

Formula (II)

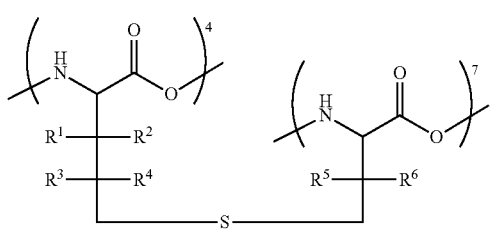

Formula (III)

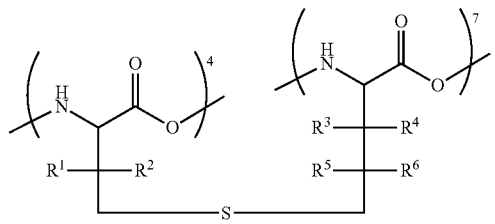

In these formulae, R$^1$, R$^2$, R$^3$, R$^4$, R$^5$ and R$^6$ are independently —H, an alkyl (e.g., C$_1$-C$_6$ alkyl, C$_1$-C$_4$ alkyl) or an aralkyl group, where the alkyl and aralkyl groups are optionally substituted with one or more halogen, —OH or —NRR' groups (where R and R' are independently —H or C$_1$-C$_4$ alkyl). In certain embodiments, R$^1$, R$^2$, R$^3$, R$^4$, R$^5$ and R$^6$ are each independently —H or —CH$_3$, such where all are —H.

In certain embodiments, the invention provides an Ang analog or derivative comprising a thioether bridge according to formula (I). Typically, R$^1$, R$^2$, R$^3$ and R$^4$ are independently selected from —H and —CH$_3$. Peptides comprising a thioether bridge according to formula (I) can be produced, for example, by lantibiotic enzymes or by sulfur extrusion of a disulfide. In one example, the disulfide from which the sulfur is extruded can be formed by D-cysteine in position 4 and L-cysteine in position 7 or by D-cysteine in position 4 and L-penicillamine in position 7 (see, e.g., Galande, Trent and Spatola (2003) *Biopolymers* 71, 534-551).

In other embodiments, the linkage of the two amino acids can be the bridges depicted in Formula (II) or Formula (III). Peptides comprising a thioether bridge according to Formula (II) can be made, for example, by sulfur extrusion of a disulfide formed by D-homocysteine in position 4 and L-cysteine in position 7. Similarly, peptides comprising a thioether bridge as in Formula (III) can be made, for example, by sulfur extrusion of a disulfide formed by D-cysteine in position 4 and L-homocysteine in position 7.

As discussed above, the Ang analogs and derivatives of the invention vary in length and amino acid composition. The Ang analogs and derivatives of the invention preferably have biological activity or are an inactive precursor molecule that can be proteolytically activated (such as how angiotensin(I), with 10 amino acids, is converted to active fragments by cleavage of 2 amino acids). The size of an Ang analog or derivative can vary but is typically between from about 5 to 10 amino acids, as long as the "core" pentameric segment comprising the 3-7 Nle-thioether-ring structure is encompassed. The amino acid sequence of an analog or derivative of the invention can vary, typically provided that it is biologically active or can become proteolytically activated. Biological activity of an analog or derivative can be determined using methods known in the art, including radioligand binding studies, in vitro cell activation assays and in vivo experiments. See, for example, Godeny and Sayeski, (2006) *Am. J. Physiol. Cell. Physiol.* 291:C1297-1307; Sarr et al., *Cardiovasc. Res.* (2006) 71:794-802; and Koziarz et al., (1933) *Gen. Pharmacol.* 24:705-713.

Ang analogs and derivatives where only the length of the peptide is varied include the following:

a 4,7-cyclized analog designated [Cyc$^{4-7}$]Ang-(1-7), which is derived from natural Ang-(1-7) (Asp$^1$-Arg$^2$-Val$^3$-Cyc$^4$-Ile$^5$-His$^6$-Cyc$^7$, SEQ ID NO: 7).

a 4,7-cyclized analog designated [Nle$^3$, Cyc$^{4-7}$]Ang-(1-10), which is derived from natural Angiotensin I (Ang-(1-10)) (Asp$^1$-Arg$^2$-Nle$^3$-Cyc$^4$-Ile$^5$-His$^6$-Cyc$^7$-Phe$^8$-His$^9$-Leu$^{10}$, SEQ ID NO: 8);

a 4,7-cyclized analog designated [Nle$^3$, Cyc$^{4-7}$]Ang-(1-8), which is derived from natural Angiotensin II (Ang-(1-8)) (Asp$^1$-Arg$^2$-Nle$^3$-Cyc$^4$-Ile$^5$-His$^6$-Cyc$^7$-Phe$^8$, SEQ ID NO: 9);

a 4,7-cyclised analog designated [Nle$^3$, Cyc$^{4-7}$]Ang-(2-8), which is derived from natural Angiotensin III (Ang-(2-8)) (Arg$^2$-Nle$^3$-Cyc$^4$-Ile$^5$-His$^6$-Cyc$^7$-Phe$^8$, SEQ ID NO: 10);

a 4,7-cyclised analog designated [Nle$^3$, Cyc$^{4-7}$]Ang-(3-8), which is derived from natural Angiotensin IV (Ang-(3-8)) (Nle$^3$-Cyc$^4$-Ile$^5$-His$^6$-Cyc$^7$-Phe$^8$, SEQ ID NO: 11);

a 4,7-cyclised analog designated [Nle$^3$, Cyc$^{4-7}$]Ang-(1-7) derived from natural Ang-(1-7) (Asp$^1$-Arg$^2$-Nle$^3$-Cyc$^4$-Ile$^5$-His$^6$-Cyc$^7$, SEQ ID NO: 12); and a 4,7-cyclised analog designated [Nle$^3$, Cyc$^{4-7}$]Ang-(1-9) derived from natural Ang-(1-9) (Asp$^1$-Arg$^2$-Nle$^3$-Cyc$^4$-Ile$^5$-His$^6$-Cyc$^7$-Phe$^8$-His$^9$, SEQ ID NO: 13).

These analogs can have one of the thioether bridges shown in Formulae (I)-(III) as the Cyc$^{4-7}$ moiety, for example, where Cyc$^4$ and Cyc$^7$ are represented by Formula (I), such as where R$^1$-R$^4$ are each —H or —CH$_3$, typically —H.

As compared to the amino acid sequence of the natural angiotensin peptide, the amino acids at positions 4 and 7 of the Cyc$^{4-7}$ analog are modified to allow introduction of the thioether-ring structures shown above. In addition to the length of the Ang analogs, the amino acids at positions other than 3, 4 and 7 can be the same or different from the naturally-occurring peptide, typically provided that the analog retains a biological function. For analogs of inactive precursors, like [Cyc$^{4-7}$]Ang-(1-10), biological function refers to one or both of an analog's susceptibility to angiotensin-converting enzymes that can cleave it to a biologically active fragment (e.g. Ang-(1-8) or Ang-(1-7)) or the biological activity of the fragment itself. In certain embodiments, an Ang analog or derivative of the invention has no intrinsic function but inhibits the effects of one or more naturally-occurring angiotensin compounds.

In certain embodiments, an Ang analog of the invention is represented by Formula (IV):

Xaa$^1$-Xaa$^2$-Xaa$^3$-Cyc$^4$-Xaa$^5$-Xaa$^6$-Cyc$^7$ (IV, SEQ ID NO: 14)

Xaa$^1$ is any amino acid, but typically a negatively-charged amino acid such as Glu or Asp, more typically Asp.

Xaa$^2$ is a positively-charged amino acid such as Arg or Lys, typically Arg.

Xaa$^3$ is an aliphatic amino acid, such as Leu, Ile or Val, typically Val.

Cyc$^4$ forms a thioether bridge in conjunction with Cyc$^7$. Cyc$^4$ can be a D-stereoisomer and/or a L-stereoisomer, typically a D-stereoisomer. Examples of Cyc$^4$ (taken with Cyc$^7$) are shown in Formulas (I), (II) and (III). Typically, the R groups in Formulae (I), (II) and (III) are —H or —CH$_3$, especially —H.

Xaa$^5$ is an aliphatic amino acid, such as Leu, Ile or Val, typically Ile.

Xaa$^6$ is His.

Cyc$^7$ forms a thioether bridge in conjunction with Cyc$^4$, such as in Formula (I), (II) or (III). Cyc$^7$ can be a D-stereoisomer and/or a L-stereoisomer, typically a L-stereoisomer. Examples of Cyc$^7$ (taken with Cyc$^4$) are shown in Formulas (I), (II), (III) and (IV). Typically, the R groups in Formulae (I), (II),) and (III) and (IV) are —H or —CH$_3$, especially —H.

In certain embodiments, one or more of Xaa$^1$-Xaa$^6$ (excluding Cyc$^4$ and Cyc$^7$) is identical to the corresponding amino acid in naturally-occurring Ang-(1-7). In certain such embodiments, all but one or two of Xaa$^1$-Xaa$^6$ are identical to the corresponding amino acid in naturally-occurring Ang-(1-7). In other embodiments, all of Xaa$^1$-Xaa$^6$ are identical to the corresponding amino acid in naturally-occurring Ang-(1-7).

In certain embodiments, Cyc$^4$ and Cyc$^7$ are independently selected from Abu (2-aminobutyric acid) and Ala (alanine), where Ala is present in at least one position. Thus, cyclic analogs can have a thioether linkage formed by -Ala$^4$-S-Ala$^7$- (Formula (I), where R$^1$-R$^4$ are each —H); -Ala$^4$-S-Abu$^7$- (Formula (I): R$^1$-R$^3$ are —H and R$^4$ is —CH$_3$) or -Abu$^4$-S-Ala$^7$- (Formula (I): R$^1$, R$^3$ and R$^4$ are —H and R$^2$ is —CH$_3$). Specific examples of cyclic analogs comprise a -Abu$^4$-S-Ala$^7$- or -Ala$^4$-S-Ala$^7$-linkage.

In certain embodiments, the invention provides an Ang-(1-7) analog with a thioether-bridge between position 4 and position 7 having the amino acid sequence Asp$^1$-Arg$^2$-Val$^3$-Abu$^4$-Ile$^5$-His$^6$-Ala$^7$ (SEQ ID NO: 15) or the amino acid sequence Asp$^1$-Arg$^2$-Val$^3$-Ala$^4$-Ile$^5$-His$^6$-Ala$^7$ (SEQ ID NO: 16), which are represented by the following structural diagrams:

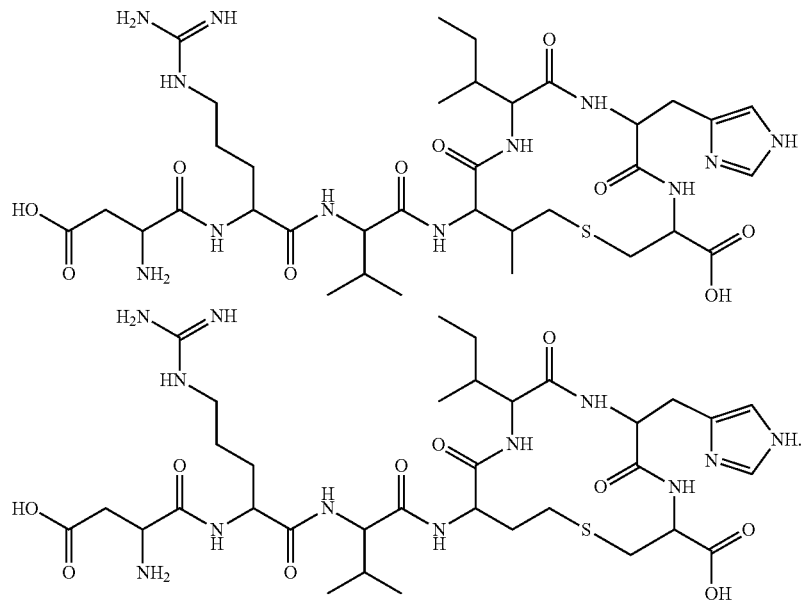

In certain embodiments, an Ang analog or derivative of the invention is represented by Formula (V):

Xaa¹-Xaa²-Nle³-Cyc⁴-Xaa⁵-Xaa⁶-Cyc⁷-Xaa⁸-Xaa⁹-Xaa¹⁰ (V, SEQ ID NO: 17)

As discussed above, one or more of Xaa¹, Xaa², Xaa⁸, Xaa⁹ and Xaa¹⁰ are absent in certain embodiments. For example, (1) Xaa¹⁰ is absent, (2) Xaa⁹ and Xaa¹⁰ are absent, (3) Xaa⁸, Xaa⁹ and Xaa¹⁰ are absent, (4) Xaa¹ is absent, (5) Xaa¹ and Xaa¹⁰ are absent, (6) Xaa¹, Xaa⁹ and Xaa¹⁰ are absent, (7) Xaa¹, Xaa⁸, Xaa⁹ and Xaa¹⁰ are absent, (8) Xaa¹ and Xaa² are absent, (9) Xaa¹, Xaa² and Xaa¹⁰ are absent, (10) Xaa¹, Xaa², Xaa⁹ and Xaa¹⁰ are absent, or (11) Xaa¹, Xaa², Xaa⁸, Xaa⁹ and Xaa¹⁰ are absent. For each of these embodiments, the remaining amino acids have the values described below.

Xaa¹, when present, is any amino acid, but typically a negatively charged amino acid such as Glu or Asp, more typically Asp.

Xaa², when present, is a positively charged amino acid such as Arg or Lys, typically Arg.

Nle³ is norleucine.

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Nle, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II) and (III). Typically, the R groups in Formulae (I), (II) and (III) are —H or —CH₃, especially —H.

Xaa⁸, when present, is an amino acid other than Pro, typically Phe or Ile. In certain embodiments, Ile results in an inhibitor of Ang(1-8). In certain embodiments, Phe maintains the biological activity of Ang(1-8) or Ang(1-10).

Xaa⁹, when present, is His.

Xaa¹⁰, when present, is an aliphatic residue, for example, Ile, Val or Leu, typically Leu.

In certain embodiments, one or more of Xaa¹-Xaa¹⁰ (excluding Nle³, Cyc⁴ and Cyc⁷) is identical to the corresponding amino acid in naturally-occurring Ang (including Ang-(1-7) (SEQ ID NO: 1), Ang(1-8) (SEQ ID NO: 26), Ang(1-9) (SEQ ID NO: 27), Ang(1-10) (SEQ ID NO: 28), Ang(2-7) (SEQ ID NO: 29), Ang(2-8) (SEQ ID NO: 30), Ang(2-9) (SEQ ID NO: 31, Ang(2-10) (SEQ ID NO: 32), Ang(3-8) (SEQ ID NO: 33), Ang(3-9) (SEQ ID NO: 34) and Ang(3-10) (SEQ ID NO: 35). In certain such embodiments, all but one or two of Xaa¹-Xaa¹⁰ (for those present) are identical to the corresponding amino acid in naturally-occurring Ang. In other embodiments, all of Xaa¹-Xaa¹⁰ (for those present) are identical to the corresponding amino acid in naturally-occurring Ang.

In certain embodiments, Cyc⁴ and Cyc⁷ are independently selected from Abu (2-aminobutyric acid) and Ala (alanine), where Ala is present at at least one position. Thus, encompassed are cyclic analogs comprising a thioether linkage formed by -Ala⁴-S-Ala⁷-(Formula (I), where R¹-R⁴ are each —H); -Ala⁴-S-Abu⁷- (Formula (I): R¹-R³ are —H and R⁴ is —CH₃) or -Abu⁴-S-Ala⁷- (Formula (I): R¹, R³ and R⁴ are —H and R² is —CH₃). Specific cyclic analogs comprise a -Abu⁴-S-Ala¹- or -Ala⁴-S-Ala⁷-linkage.

In particular, the invention provides an Ang-(1-7) analog or derivative with a thioether-bridge between position 4 and position 7 having the amino acid sequence Asp¹-Arg²-Nle³-Abu⁴-Ile⁵-His⁶-Ala⁷ (SEQ ID NO: 18) or the amino acid sequence Asp¹-Arg²-Nle³-Ala⁴-Ile⁵-His⁶-Ala⁷ (SEQ ID NO: 19).

In another aspect, the invention provides an Ang-(1-8) analog or derivative with a thioether-bridge between position 4 and position 7 having Ang-(1-8) antagonistic activity, in particular an Ang(1-8) analog or derivative having the amino acid sequence Asp¹-Arg²-Nle³-Abu⁴-Ile⁵-His⁶-Ala⁷-Ile⁸ (SEQ ID NO: 20), or the amino acid sequence Asp¹-Arg²-Nle³-Ala⁴-Ile⁵-His⁶-Ala⁷-Ile⁸ (SEQ ID NO: 21).

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An aralkyl group is an alkyl group substituted by an aryl group. Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Ang (1-7) Receptor Agonists

In some embodiments, the present invention provides methods of treating stroke including administering an angiotensin (1-7) receptor agonist to a subject suffering from a stroke, approximately 24 hours after the stroke. As used herein, the term "angiotensin-(1-7) receptor agonist" encompasses any molecule that has a positive impact in a function of an angiotensin-(1-7) receptor, in particular, the G-protein coupled Mas receptor. In some embodiments, an angiotensin-(1-7) receptor agonist directly or indirectly enhances, strengthens, activates and/or increases an angiotensin-(1-7) receptor (i.e., the Mas receptor) activity. In some embodiments, an angiotensin-(1-7) receptor agonist directly interacts with an angiotensin-(1-7) receptor (i.e., the Mas receptor). Such agonists can be peptidic or non-peptidic including, e.g., proteins, chemical compounds, small molecules, nucleic acids, antibodies, drugs, ligands, or other agents. In some embodiments, the angiotensin (1-7) receptor agonist is a non-peptidic agonist.

An exemplary class of angiotensin-(1-7) receptor agonists are 1-(p-thienylbenzyl)imidazoles. Examples of these non-peptide angiotensin-(1-7) receptor agonists are represented by Structural Formula (VI):

(VI)

or pharmaceutically acceptable salts thereof, wherein:

$R^1$ is halogen, hydroxyl, $(C_1\text{-}C_4)$-alkoxy, $(C_1\text{-}C_8)$-alkoxy wherein 1 to 6 carbon atoms are replaced by the heteroatoms O, S, or NH (preferably by O), $(C_1\text{-}C_4)$-alkoxy substituted by a saturated cyclic ether such as tetrahydropyran or tetrahydrofuran, O—$(C_1\text{-}C_4)$-alkenyl, O—$(C_1\text{-}C_4)$-alkylaryl, or aryloxy that is unsubstituted or substituted by a substituent selected from halogen, $(C_1\text{-}C_3)$-alkyl, $(C_1\text{-}C_3)$-alkoxy and trifluoromethyl;

$R^2$ is CHO, COOH, or (3) CO—O—$(C_1\text{-}C_4)$-alkyl;

$R^3$ is $(C_1\text{-}C_4)$-alkyl or aryl;

$R^4$ is hydrogen, halogen (chloro, bromo, fluoro), or $(C_1\text{-}C_4)$-alkyl;

X is oxygen or sulfur;

Y is oxygen or —NH—;

$R^5$ is hydrogen, $(C_1\text{-}C_6)$-alkyl; or $(C_1\text{-}C_4)$-alkylaryl, where $R^5$ is hydrogen when Y is —NH—; and $R^6$ is $(C_1\text{-}C_5)$-alkyl.

In certain embodiments, $R^1$ is not halogen when $R^2$ is COOH or CO—O—$(C_1\text{-}C_4)$-alkyl.

In some embodiments, an angiotensin-(1-7) receptor agonist is AVE 0991, 5-formyl-4-methoxy-2-phenyl-1[[4-[2-(ethylaminocarbonylsulfonamido)-5-isobutyl-3-thienyl]-phenyl]-methyl]-imidazole, which is represented by the following structure:

Another exemplary class of angiotensin-(1-7) receptor agonists are p-thienylbenzylamides. Examples of these non-peptide angiotensin-(1-7) receptor agonists are represented by Structural Formula (VII):

(VII)

or a pharmaceutically acceptable salt thereof, wherein:

$R^1$ is $(C_1\text{-}C_5)$-alkyl that is unsubstituted or substituted by a radical chosen from $NH_2$, halogen, O—$(C_1\text{-}C_3)$-alkyl, CO—O—$(C_1\text{-}C_3)$-alkyl and $CO_2H$, $(C_3\text{-}C_8)$-cycloalkyl, $(C_1\text{-}C_3)$-alkyl-$(C_3\text{-}C_8)$-cycloalkyl, $(C_6\text{-}C_{10})$-aryl that is unsubstituted or substituted by a radical chosen from halogen and O—$(C_1\text{-}C_3)$-alkyl, $(C_1\text{-}C_3)$-alkyl-$(C_6\text{-}C_{10})$-aryl where the aryl radical is unsubstituted or substituted by a radical chosen from halogen and O—$(C_1\text{-}C_3)$-alkyl, $(C_1\text{-}C_5)$-heteroaryl, or $(C_1\text{-}C_3)$-alkyl-$(C_1\text{-}C_5)$-heteroaryl;

$R^2$ is hydrogen, $(C_1\text{-}C_6)$-alkyl that is unsubstituted or substituted by a radical chosen from halogen and O—$(C_1\text{-}C_3)$-alkyl, $(C_3\text{-}C_8)$-cycloalkyl, $(C_1\text{-}C_3)$-alkyl-$(C_3\text{-}C_8)$-cycloalkyl, $(C_6\text{-}C_{10})$-aryl that is unsubstituted or substituted by a radical chosen from among halogen, O—$(C_1\text{-}C_3)$-alkyl and CO—O—$(C_1\text{-}C_3)$-alkyl, or $(C_1\text{-}C_3)$-alkyl-$(C_6\text{-}C_{10})$-aryl that is unsubstituted or substituted by a radical chosen from halogen and O—$(C_1\text{-}C_3)$-alkyl;

$R^3$ is hydrogen, COOH, or COO—$(C_1\text{-}C_4)$-alkyl;

$R^4$ is hydrogen, halogen; or $(C_1\text{-}C_4)$-alkyl;

$R^5$ is hydrogen or $(C_1\text{-}C_6)$-alkyl;

$R^6$ is hydrogen, $(C_1\text{-}C_6)$-alkyl, $(C_1\text{-}C_3)$-alkyl-$(C_3\text{-}C_8)$-cycloalkyl, or $(C_2\text{-}C_6)$-alkenyl; and X is oxygen or NH.

Additional examples of angiotensin-(1-7) receptor agonists are described in U.S. Pat. No. 6,235,766, the contents of which are incorporated by reference herein.

Various angiotensin-(1-7) receptor agonists described above can be present as pharmaceutically acceptable salts. As used herein, "a pharmaceutically acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts formed from a cationic material may utilize the conjugate base of these inorganic and organic acids. Salts may also be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin.

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An alkenyl group is a straight chained or branched non-aromatic hydrocarbon that is includes one or more double bonds. Typically, a straight chained or branched alkenyl group has from 2 to about 20 carbon atoms, preferably from 2 to about 10. Examples of straight chained and branched alkenyl groups include ethenyl, n-propenyl, and n-butenyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

An aralkyl group is an alkyl group substituted by an aryl group.

Formulations and Dosing

In accordance with the methods of the invention, an Ang (1-7) peptide or angiotensin (1-7) receptor agonist as described herein of the invention can be administered to a subject alone (e.g., as a purified peptide or compound), or as a component of a composition or medicament (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An Ang (1-7) peptide or angiotensin (1-7) receptor agonist as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An Ang (1-7) peptide or angiotensin (1-7) receptor agonist as described herein (or a composition or medicament containing an Ang (1-7) peptide or angiotensin (1-7) receptor agonist described herein) is administered by any appropriate route. In some embodiments, an Ang (1-7) peptide or angiotensin (1-7) receptor agonist described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an Ang (1-7) peptide or angiotensin (1-7) receptor agonist described herein is administered intravenously. Alternatively, an Ang (1-7) peptide or angiotensin (1-7) receptor agonist described herein (or a composition or medicament containing an Ang (1-7) peptide or angiotensin (1-7) receptor agonist described herein) can be administered by inhalation, parenterally, intradermally, transdermally, rectally, or transmucosally. In some embodiments, an Ang(1-7) peptide or angiotensin (1-7) receptor agonist is administered orally. More than one route can be used concurrently, if desired. In some embodiments, an Ang (1-7) peptide is administered in any non-intracerebroventricular manner.

In some embodiments, a composition is administered in a therapeutically effective amount and/or according to a dosing regimen that is correlated with a particular desired outcome (e.g., with treating or reducing risk for ischemic stroke).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

In various embodiments, an Ang (1-7) peptide or angiotensin (1-7) receptor agonist is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of angiotensin (1-7) peptides or angiotensin (1-7) receptor agonists, including derivatives, analogs, and/or salts may be present in varying amounts in various embodiments. For example, in some embodiments, a therapeutically effective amount of an angiotensin (1-7) peptide may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, an angiotensin (1-7) peptide or angiotensin (1-7) receptor agonist is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, an angiotensin (1-7) peptide or angiotensin (1-7) receptor agonist is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, the angiotensin (1-7) peptide is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the angiotensin (1-7) peptide is administered at an effective dose ranging from about 1-500 µg/kg/day. In some embodiments, the angiotensin (1-7) peptide is administered at an effective dose ranging from about 1-100 µg/kg/day. In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 µg/kg/day.

Dosing Schedules

According to various embodiments, the present invention provides several new dosing schedules not previously thought appropriate or beneficial in the treatment of stroke. In contrast to the established thinking regarding stroke treatment, where "time is brain," some embodiments of the present invention allow for treatment to begin well after a stroke event. Alternatively or additionally, some embodiments provide methods wherein treatment occurs well after a stroke event (whether or not such treatment is a first treatment), a strategy that was previously thought to be ineffective. In particular, several embodiments may include a dosing schedule wherein a treatment of a patient with an Ang (1-7) peptide occurs more than 3 hours after the stroke event. In some embodiments, a treatment of a patient with an Ang (1-7) peptide occurs more than 4 hours, 5 hours, 6 hours, 7 hours, 8 hours, 9 hours, 10 hours, 12 hours, 15 hours, 18 hours, 20 hours, 24 hours, 30 hours, 36 hours, 42 hours, 48 hours, 54 hours, 60 hours, 66 hours, 72 hours, 78 hours, 84 hours, 90 hours, or 96 hours after the stroke event. In some embodiments, a treatment of a patient with an Ang (1-7) peptide occurs more than 1 day, 2 days, 3 days, 4 days, 5 days, or 6 days after a stroke event. In some embodiments, a treatment of a patient with an Ang (1-7) peptide occurs more than 1 week, 2 weeks, 3 weeks, 4 weeks, 5 weeks, 6 weeks, 7 weeks, 8 weeks, 9 weeks, or 10 weeks after the stroke event. In some embodiments, such treatment with an angiotensin (1-7) peptide is the first treatment of stroke in a subject.

Combination Therapies

In some embodiments, an Ang (1-7) peptide or an angiotensin (1-7) receptor agonist may be used as a part of a combination therapy. It is contemplated that any known therapy or therapeutic for the treatment of stroke may be used with one or more Ang (1-7) peptides and/or angiotensin (1-7) receptor agonists as disclosed herein. Exemplary therapies that may be used with one or more Ang (1-7) peptides and/or angiotensin (1-7) receptor agonists include, but are not limited to, pro-urokinase, anticoagulants, antiplatelet therapies, antihypertensives, thrombolytic compounds, antioxidants or other reactive oxygen species agents, and combinations thereof. Exemplary, non-limiting, specific therapeutic agents which may be used as a part of a combination therapy according to provided methods include interferon beta-1a (e.g. Avonex, Rebif, CinnoVex, ReciGen), interferon beta-1b (Betaseron), glatiramer acetate (Copaxone), mitoxantrone (Novantrone), natalizumab (Tysabri), fingolimod (Gilenya), Teriflunomide (Aubagio), aspirin, dipyridamole (Aggrenox), clopidogrel (Plavix) warfarin (Coumadin), one or more statins, and combinations thereof. In some embodiments, an Ang(1-7) peptide and/or an angiotensin (1-7) receptor agonist may be administered prior to, concurrently with, or subsequent to one or more surgical procedures, such as those outlined above (e.g., thrombectomy).

In some embodiments, an Ang (1-7) peptide and/or Ang (1-7) receptor agonist may be administered subsequent to a prior treatment of stroke in a subject, for example, one or more of the therapeutics and/or surgical interventions described above. In some embodiments, the prior treatment of stroke takes place within 3 hours of a stroke. In some embodiments, the prior treatment takes place within 12 hours of a stroke. In some embodiments, a prior treatment comprises administration of an Ang (1-7) peptide and/or Ang (1-7) receptor agonist.

Kits

In some embodiments, the present invention further provides kits or other articles of manufacture which contains an Ang (1-7) peptide, an angiotensin (1-7) receptor agonist, or a formulation containing the same and provides instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold one or more formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing an Ang (1-7) peptide or angiotensin (1-7) receptor agonist. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

EXAMPLES

Example 1

Delayed Treatment of Stroke with TXA127 (SEQ ID NO: 1)

In this Example, angiotensin (1-7) peptides were used in a rat Transient Middle Cerebral Artery Occlusion (tMCAO) model, which is generally accepted model of ischemic stroke.

Specifically, a total of 105 Sprague Dawley rats were used, as seven groups with 15 rats in each. Each rat was approximately 3 months old and weighed approximately 300 grams±20% at the initiation of the study.

Animal handling was performed according to the guidelines of the National Institutes of Health (NIH) and the Association for the Assessment and Accreditation of Laboratory Animal Care (AAALAC). Animals were fed ad libitum a commercial rodent diet, had free access to drinking water, and were housed under standard laboratory conditions with a 12 hour light/dark cycle.

In this Example, the day of the tMCAO procedure is defined as "Day 1" of the study.

TXA127 (SEQ ID NO: 1) dose volume was 0.5 ml/kg for daily injections. TXA127 was dissolved in PBS buffer to a concentration of 25 mg/ml (stock solution). For the working solution by daily injections TXA127 was dissolved in PBS in concentration of 0.2 mg/ml for dose level 100 µg/kg; 0.6 mg/ml for dose level 300 µg/kg; 1 mg/ml for dose level 500 µg/kg. For Alzet pump injections TXA127 was dissolved in PBS in concentration of 5 mg/ml for dose level 100 µg/kg; 15 mg/ml for dose level 300 µg/kg; 25 mg/ml for dose level 500 µg/kg. Alzet pump dose volume per 24 h was 6 µg total.

Transient middle cerebral artery occlusion was performed according to the method described R. Schmid-Eisaesser et al. Briefly, the right CCA (Common Carotid Artery) was exposed through a midline neck incision and carefully dissected free from surrounding nerves and fascia —from its bifurcation to the base of the skull. The occipital artery branches of the ECA (External Carotid Artery) were then isolated, and these branches were dissected and coagulated. The ECA was dissected further distally and coagulated along with the terminal lingual and maxillary artery branches, which was then divided. The ICA (Internal Carotid Artery) was isolated and carefully separated from the adjacent vagus nerve, and the pterygopalatine artery was ligated close to its origin with a 5-0 nylon suture (SMI, Belgium). Next a 4-0 silk suture was tied loosely around the mobilized ECA stump, and a 4 cm length of 4-0 monofilament nylon suture (the tip of the suture was blunted by using a flame, and the suture was coated with polylysine, prior to insertion) was inserted through the proximal ECA into the ICA and thence into the circle of Willis, effectively occluding the MCA. The surgical wound was closed and the animals were returned to their cages to recover from anesthesia. One hour and a half after occlusion rats were re-anesthetized, the monofilament was withdrawn to allow reperfusion, the surgical wound was closed and rats were returned to their cages.

Animals were subjected to the mNSS test (Neuroscore) at Day 2, 24 hours post reperfusion. Only animals with an overall score of ≥10 were included in this Example.

Evaluation of the blood flow in the brain cortex and vessel constriction was carried out using a Flow-R Laser Doppler system, in which intracranial blood flow and vessel diameter (constriction/dilation) was monitored.

First Phase of Study—Treatment of Stroke Complications Wherein Treatment is Initiated 24 Hours after Stroke Event In the first phase of this Example, rats were exposed to an angiotensin (1-7) peptide (TXA127) beginning on the day after the stroke event and continuing for 49 days. Starting on Day 2, 24 hours post-surgery, animals in group 5 (100 µg/kg Alzet), Group 6 (300 µg/kg Alzet) and Group 7 (500 µg/kg Alzet) were implanted subcutaneously with osmotic Alzet pump and were treated via continuous TXA127 administration. Animals in Group 2 (100 µg/kg SC), Group 3 (300 µg/kg SC) and Group 4 (500 µg/kg SC) received TXA127 administered subcutaneously with daily injection. Animals in Group 1 (vehicle control) were treated with a vehicle. Table 1 shows the group design used in this Example.

TABLE 1

Group Allocation

| Group | Treatment | Dose | Treatment Duration (days) | Total Rats |
|---|---|---|---|---|
| 1 | Vehicle | 0 | 28 | 15 |
| 2 | TXA127 | 100 µg/kg | 28 | 15 |
| 3 | TXA127 | 300 µg/kg | 28 | 15 |
| 4 | TXA127 | 500 µg/kg | 28 | 15 |
| 5 | TXA127 | 100 µg/kg (Alzet) | 28 | 15 |
| 6 | TXA127 | 300 µg/kg (Alzet) | 28 | 15 |
| 7 | TXA127 | 500 µg/kg (Alzet) | 28 | 15 |

Body Weight (Day 1, 8, 15, 22, 29, 36, 43, 50)

Body weight of each animal was measured once a week in all treatment groups and the results are shown in FIG. 1.

Neurological Scoring (Pre-Operation, and Day 2, 15, 22, 29, 36, 43, and 50)

Each animal was also subjected to a neuroscore test. The Modified Neurological Rating Scale (mNRS), or Neuroscore, was performed before the operation, on Day 2 and on Day 15, Day 22, Day 29, Day 36 Day 43 and Day 50. The individual making the behavioral assessments was unaware of the drug/dose given (blind test). A total Neuroscore of 18 was possible, with higher scores correlating to worse functioning.

Figure 2:
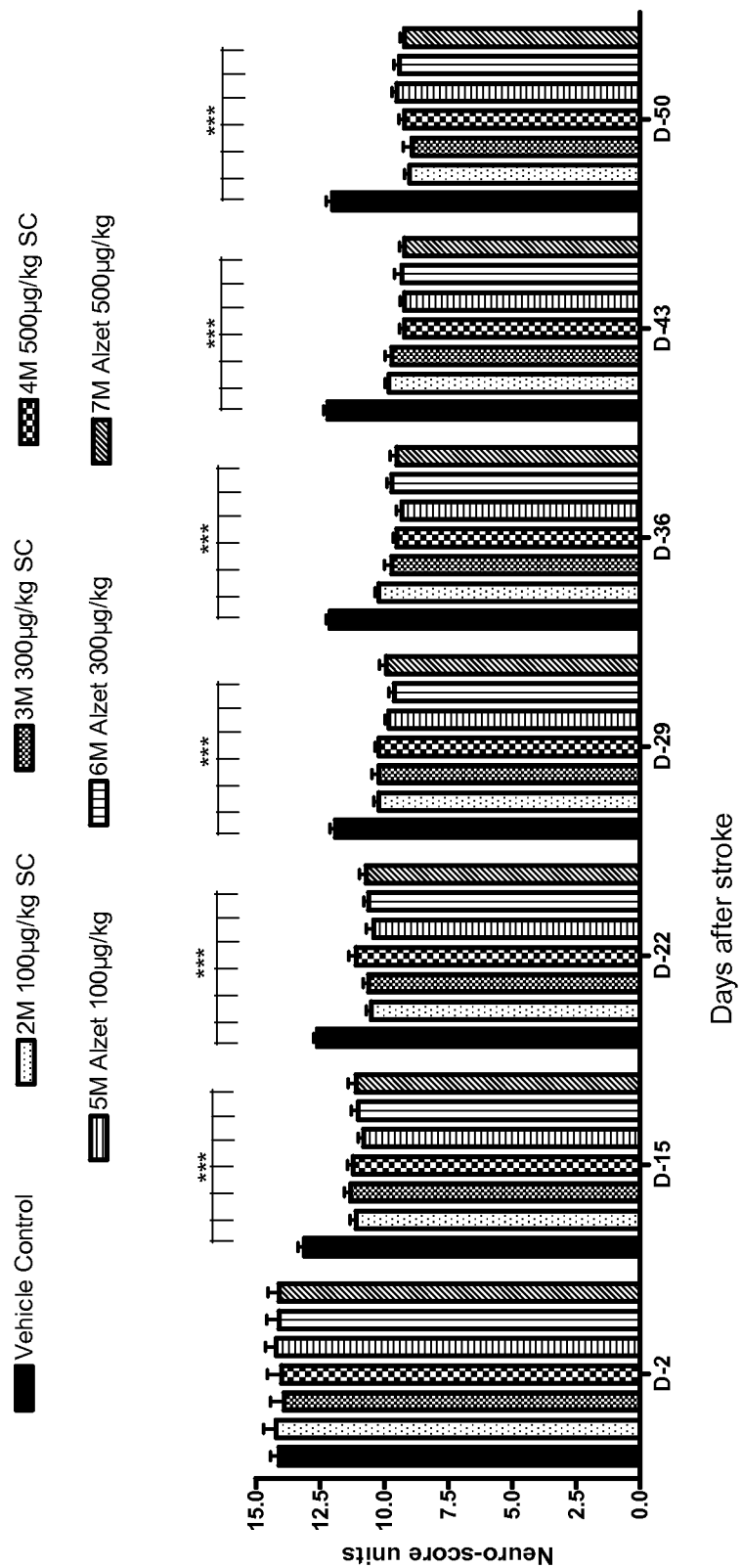
FIG. 2 shows a graph of exemplary neuroscores from rats exposed to one of: vehicle, 100 μg/kg TXA127 (SEQ ID NO: 1), 300 μg/kg TXA127, 500 μg/kg TXA127, 100 μg/kg TXA127, 300 μg/kg TXA127, or 500 μg/kg TXA127 given either subcutaneously or via continuous infusion for up to seven weeks.

As shown in FIG. 2, by day 15, all treatment groups showed a statistically significant reduction in neuroscore as compared to vehicle control animals by day 15, and this effect was maintained through day 50.

Stepping Test (Pre-Operation, and Day 15, 22, 29, 36, 43, and 50)

Animals were tested for forelimb akinesia in a stepping test (ST). The animal was held by its hind limbs fixed with one hand and the forelimb not to be monitored with the other, while the unrestrained fore-paw touched the table. The number of adjusting steps were counted while the animal is moved, sideways along the table surface (85 cm in approximately five seconds), in the forehand & backhand direction for both forelimbs.

Figure 3:
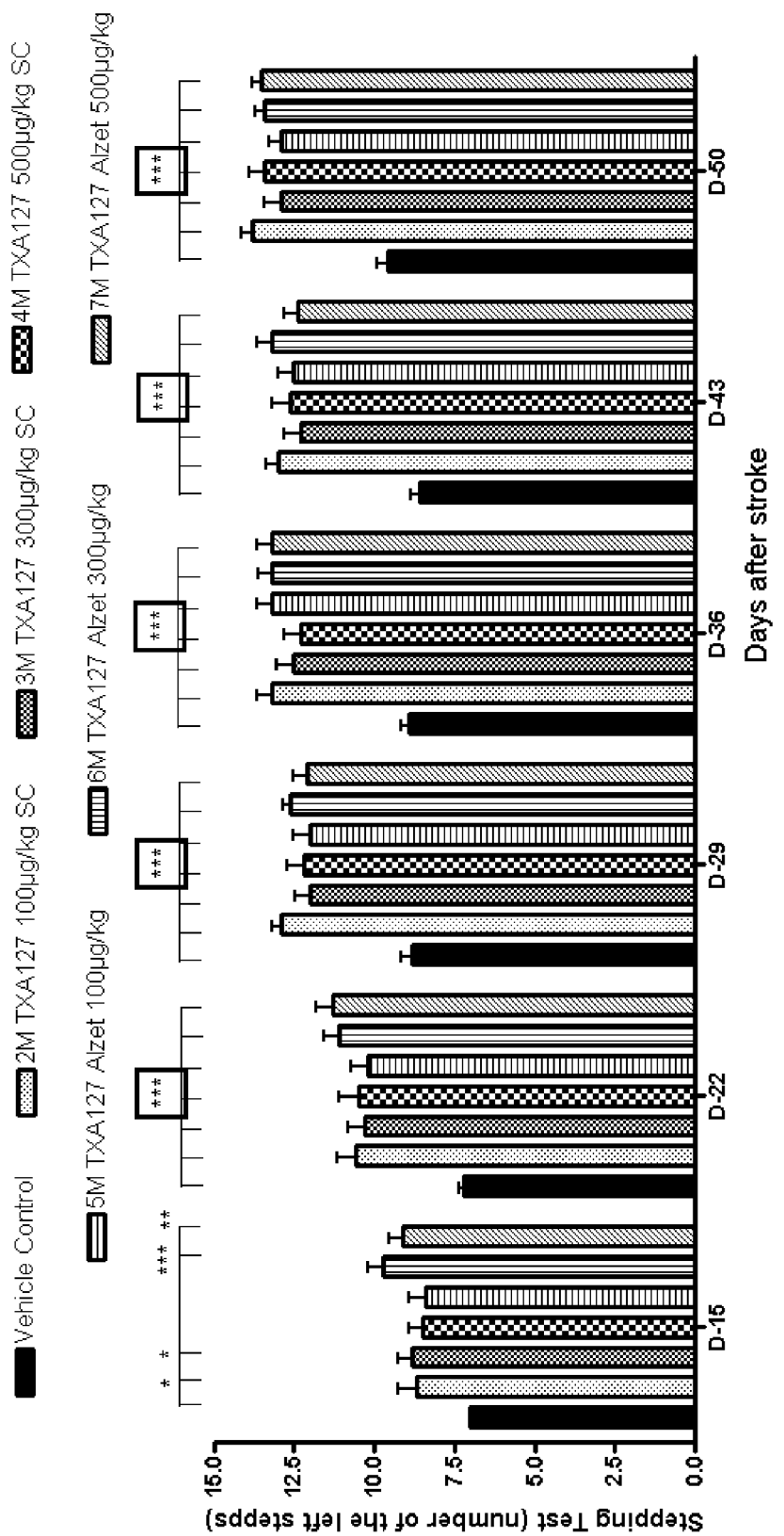
FIG. 3 shows exemplary results in a stepping test from rats exposed to one of: 100 μg/kg TXA127 (SEQ ID NO: 1), 300 μg/kg TXA127, 500 μg/kg TXA127, 100 μg/kg TXA127, 300 μg/kg TXA127, or 500 μg/kg TXA127 given either subcutaneously or via continuous infusion for up to seven weeks.

FIG. 3 shows that administration of TXA127 provided a significant improvement in performance in all treatment groups by day 22, as compared to vehicle control animals. By Day 15, all treatment groups were either trending toward improvement or already showing statistically significant improvement.

Limb Placement Test (Pre-Operation, and Day 15, 22, 29, 36, 43 and 50)

Animals were subjected to a limb placement test. The limb placing tests were divided into both forelimb and hindlimb tests. For the forelimb-placing test, the examiner held the rat close to a tabletop and scored the rat's ability to place the forelimb on the tabletop in response to whisker, visual, tactile or proprioceptive stimulation. Similarly, for the hindlimb placing test, the examiner assessed the rat's ability to place the hindlimb on the tabletop in response to tactile and proprioceptive stimulation. Separate sub-scores are obtained for each mode of sensory input and added to give total scores (for the forelimb placing test: 0=normal, 12=maximally impaired; for the hindlimb placing test: 0=normal; 6=maximally impaired). Scores were given in half-point increments (see below).

Forelimb placing test (0-12);
Whisker placing (0-2);
Visual placing (forward (0-2), sideways (0-2))
Tactile placing (dorsal (0-2), lateral (0-2))
Proprioceptive placing (0-2)

Figure 4:
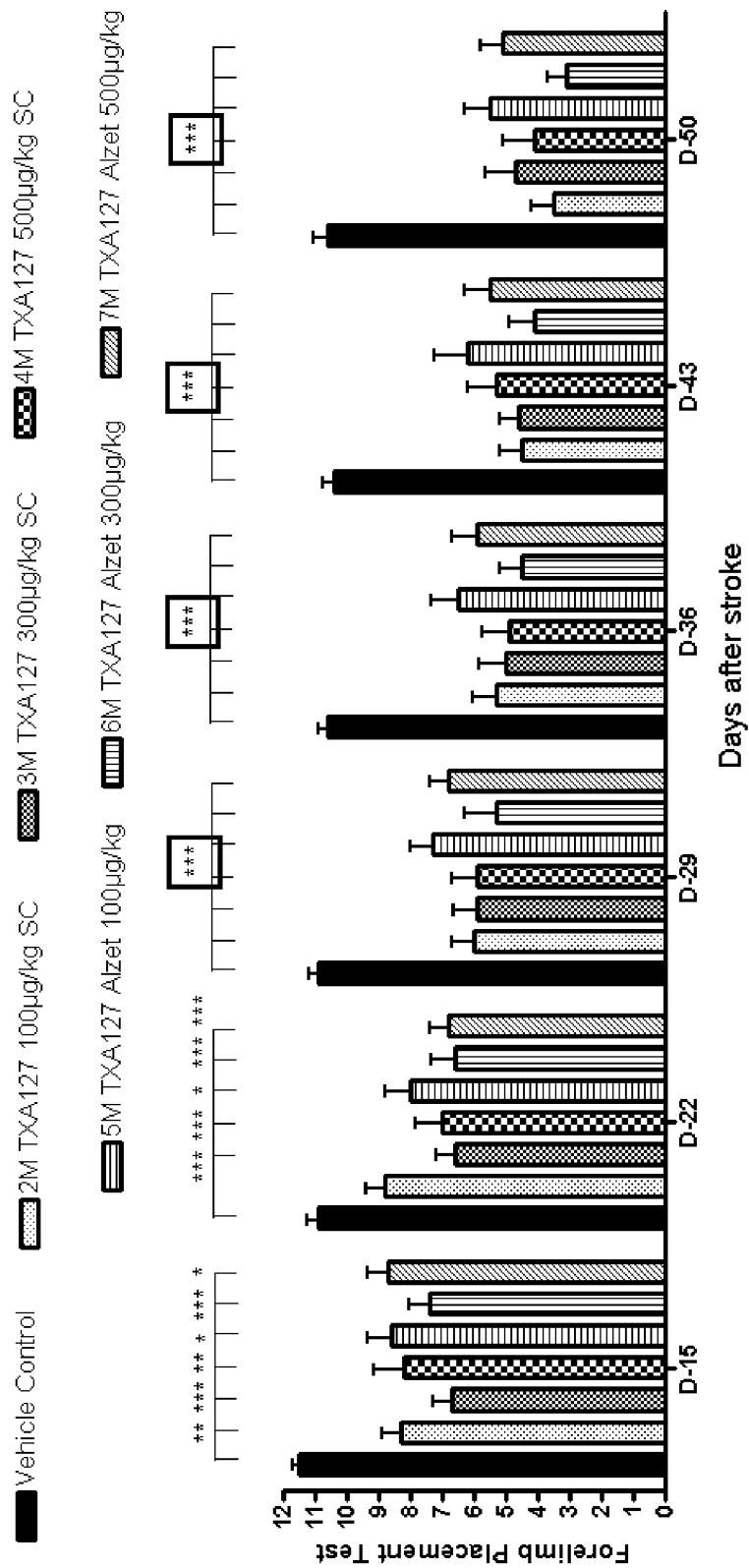
FIG. 4 shows exemplary results from a forelimb placement tests from rats exposed to one of: 100 μg/kg TXA127 (SEQ ID NO: 1), 300 μg/kg TXA127, 500 μg/kg TXA127, 100 μg/kg TXA127, 300 μg/kg TXA127, or 500 μg/kg TXA127 given either subcutaneously or via continuous infusion for up to seven weeks.

The results provided in FIG. 4 show that all treatment groups enjoyed statistically significant improvements in performance by day 15 as compared to vehicle control. Also, as shown in FIG. 4, these improvements continued through day 50, in many groups trending toward increased performance over time.

Body Swing Test (Pre-Operation, and Day 15, 22, 29, 36, 43, and 50)

Animals were also subjected to a body swing test. Each rat was held approximately one inch from the base of its tail. It was then elevated to an inch above a surface of a table. The rat was held in the vertical axis, defined as no more than 10° to either the left or the right side. A swing was recorded whenever the rat moved its head out of the vertical axis to either side. Before attempting another swing, the rat had to return to the vertical position for the next swing to be counted, Twenty (20) total swings were counted. A normal rat typically has an equal number of swings to either side. Following focal ischemia, the rat tends to swing to the contralateral side (left side in this Example). Body swing scores were expressed as a percentage of rightward over total swings.

Figure 5:
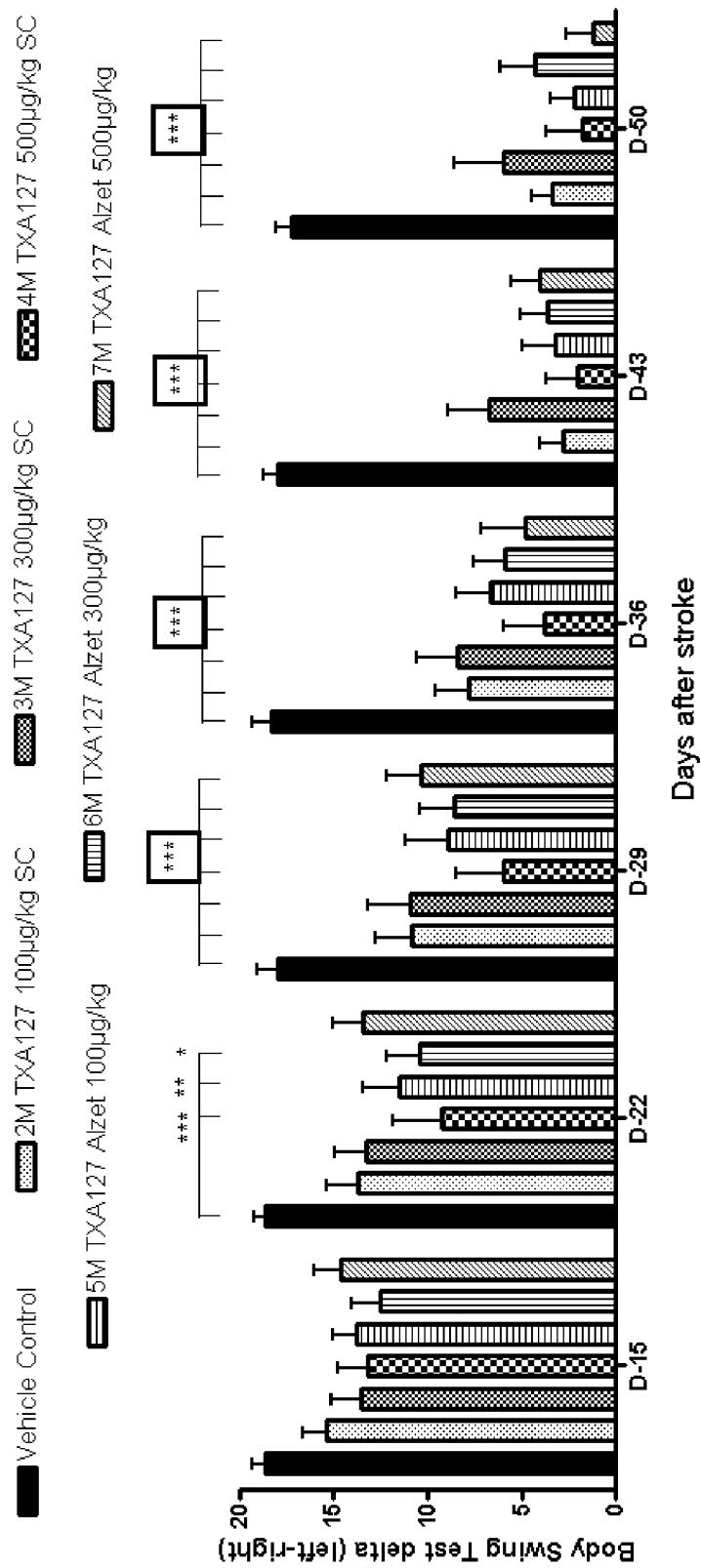
FIG. 5 shows exemplary results from a body swing test (left turn-right turn) from rats exposed to one of: 100 μg/kg TXA127 (SEQ ID NO: 1), 300 μg/kg TXA127, 500 μg/kg TXA127, 100 μg/kg TXA127, 300 μg/kg TXA127, or 500 μg/kg TXA127 given either subcutaneously or via continuous infusion for up to seven weeks.

The results of the body swing test are provided in FIG. 5, which shows that by day 15 an improvement in performance is enjoyed by all treatment groups, with statistical significance being achieved by day 22 in some groups, and day 29 in all treatment groups. As with the limb placement test above, performance appears to continue to improve over time.

Blood Vessel Diameter and Blood Flow Ratios

Figure 6:
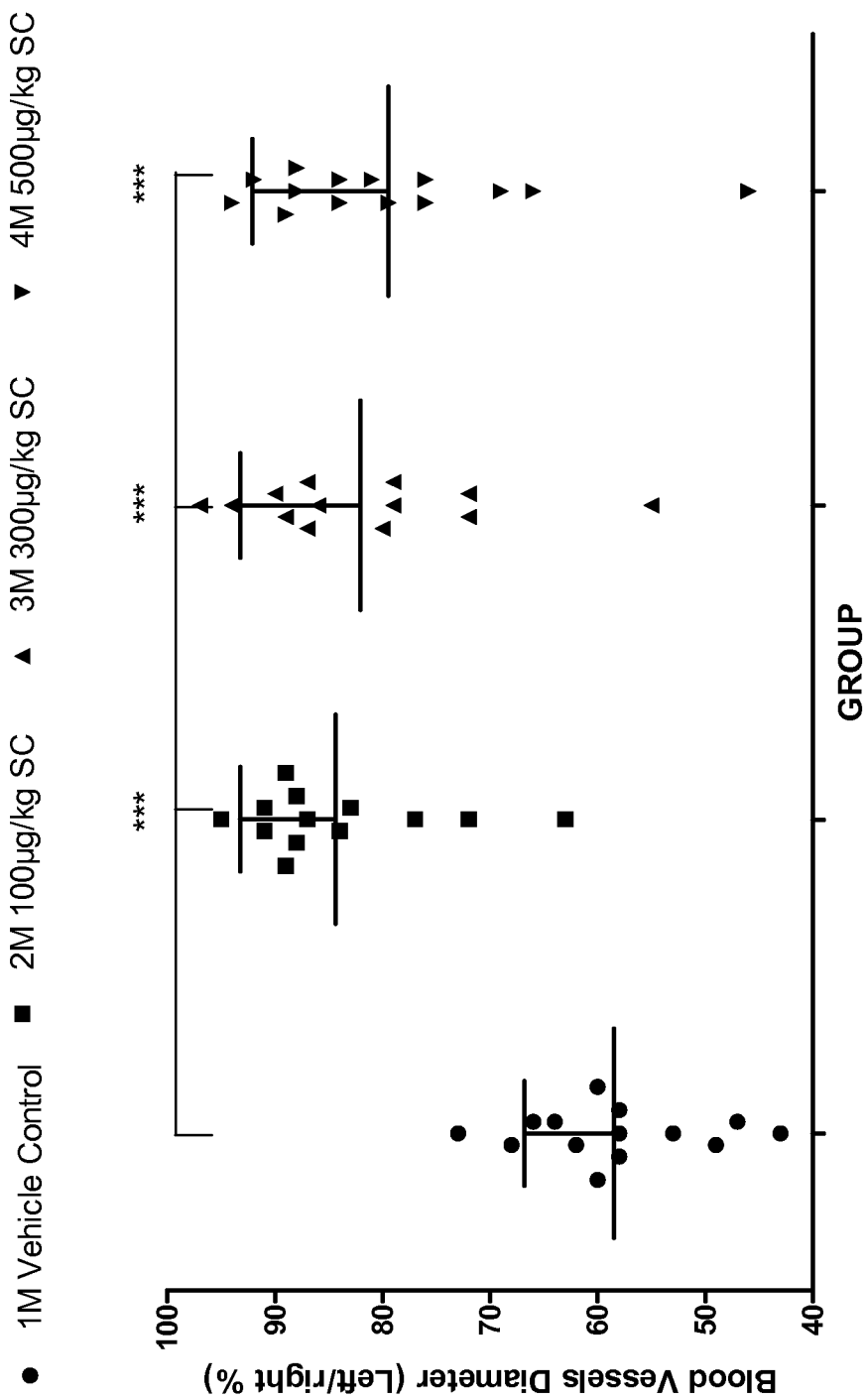
FIG. 6 shows an example of the percent change of average vessel diameter in rats exposed to one of: vehicle, 100 μg/kg TXA127 (SEQ ID NO: 1), 300 μg/kg TXA127, or 500 μg/kg TXA127 given subcutaneously for 50 days.
Figure 7:
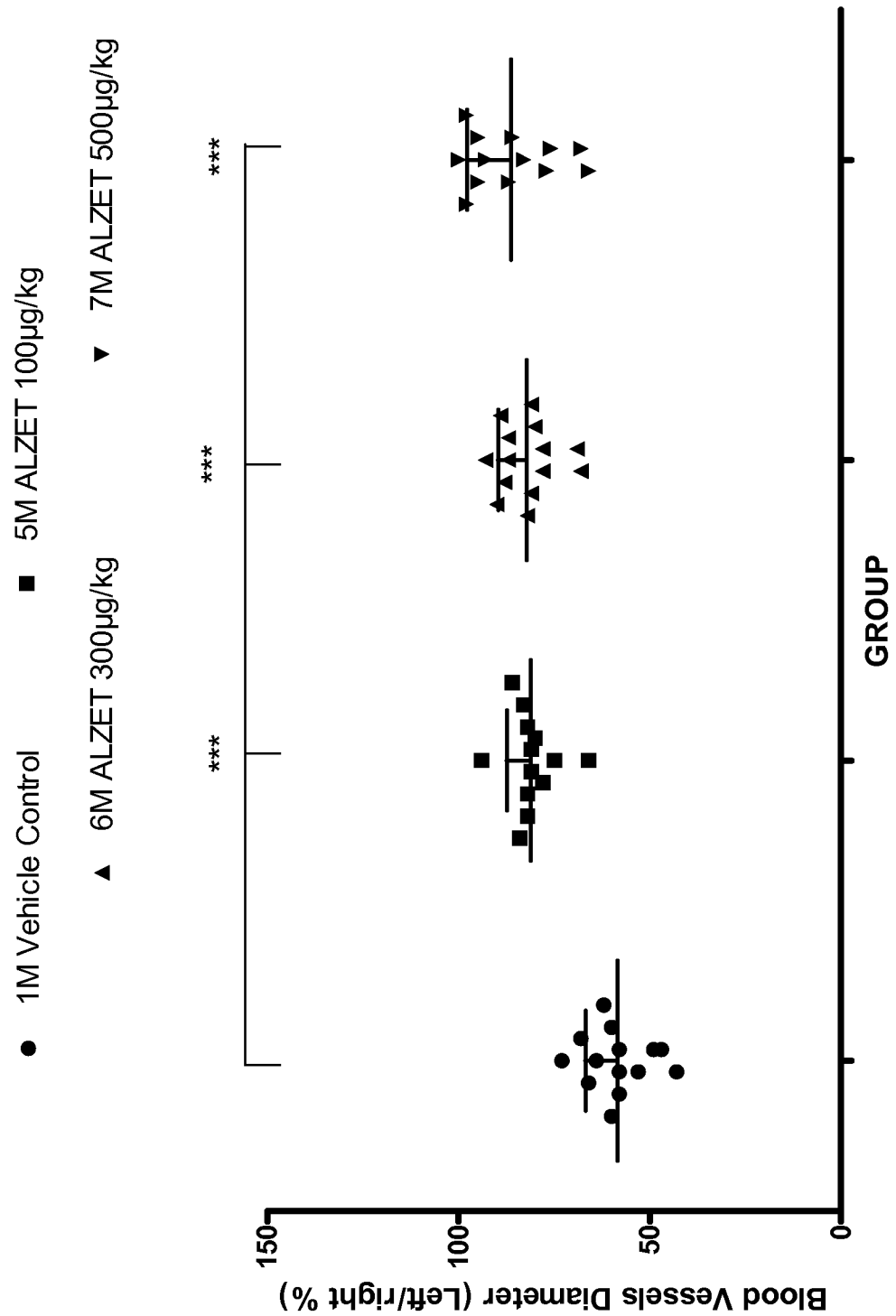
FIG. 7 shows an example of the percent change of average vessel diameter in rats exposed to one of: vehicle, 100 μg/kg TXA127 (SEQ ID NO: 1), 300 μg/kg TXA127, or 500 μg/kg TXA127 given via continuous infusion for 50 days.

On day 50 (49 days after the stroke event), the blood vessel diameter of all animals was tested. FIGS. 6 and 7 show that by day 50 animals in all treatment groups showed statistically significant improvement in blood vessel diameter, as compared to vehicle control animals. Specifically, FIG. 6 shows that each treatment group receiving subcutaneously administered TXA127 showed enhanced blood vessel diameter of approximately 20% larger than vehicle control animals. FIG. 7 shows an even greater improvement (~40%) in animals receiving a continuous infusion of TXA127 via Alzet pump, as compared to vehicle controls.

Figure 8:
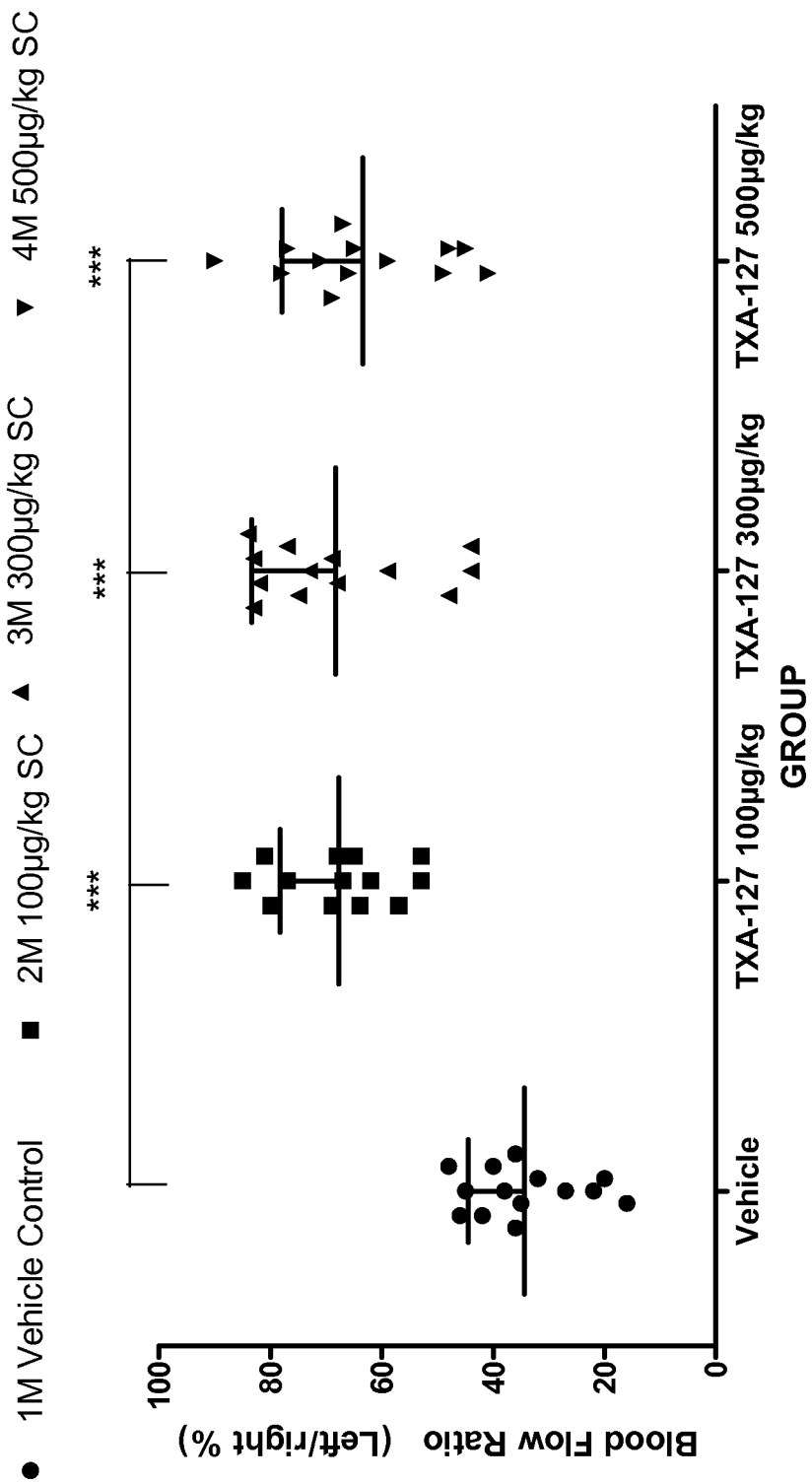
FIG. 8 shows exemplary changes in blood flow in rats exposed to one of: vehicle, 100 μg/kg TXA127 (SEQ ID NO: 1), 300 μg/kg TXA127, or 500 μg/kg TXA127 given subcutaneously for 50 days.
Figure 9:
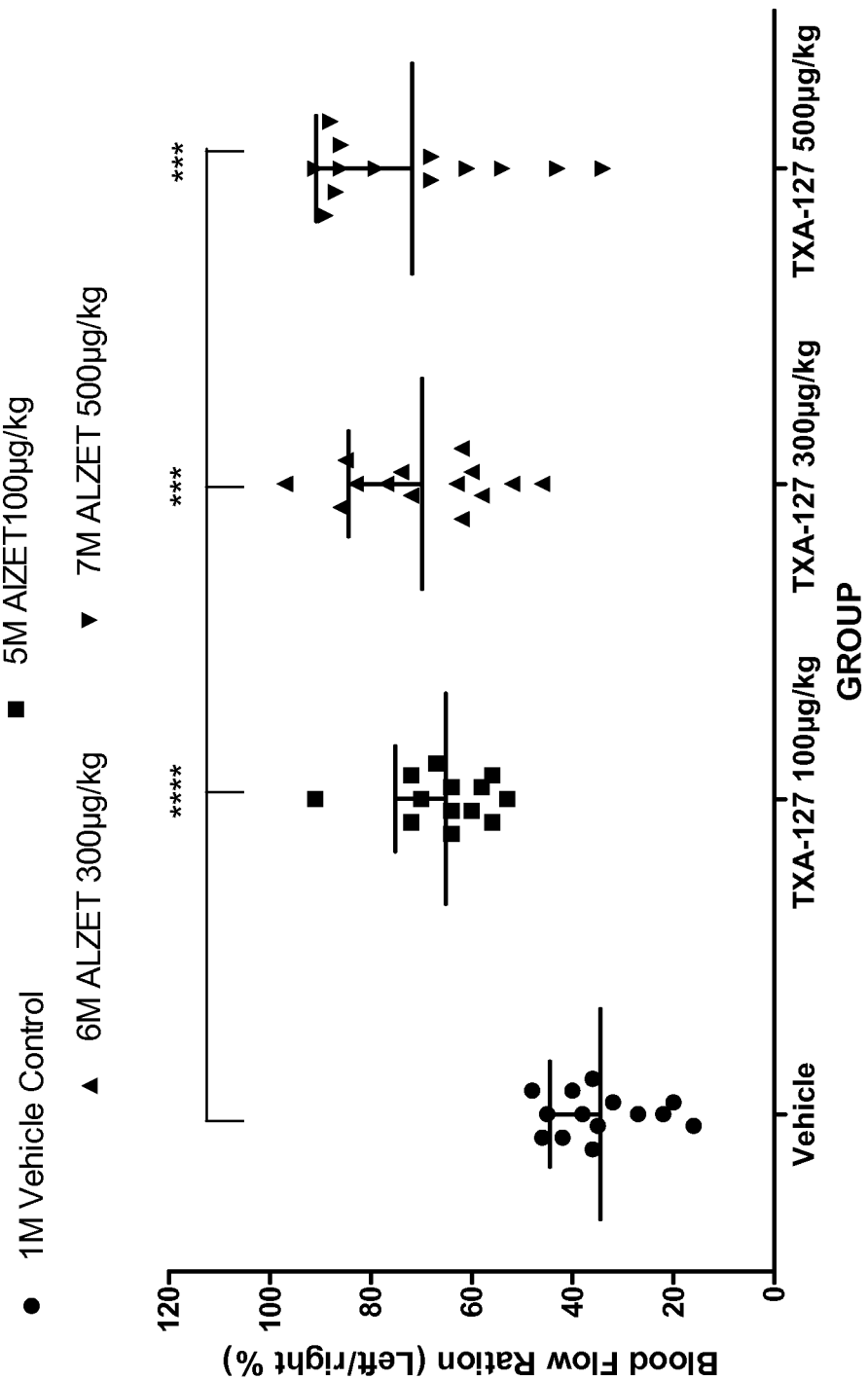
FIG. 9 shows exemplary changes in blood flow in rats exposed to one of: vehicle, 100 μg/kg TXA127 (SEQ ID NO: 1), 300 μg/kg TXA127, or 500 μg/kg TXA127 given via continuous infusion for 50 days.

In addition to the measurement of blood vessel diameter, blood flow measurements were also taken on Day 50 in all groups. Similar to vessel diameter above, FIGS. 8 and 9 show that by day 50 animals in all treatment groups show a statistically significant improvement in blood flow as compared to vehicle control animals. FIG. 8 shows that each treatment group receiving subcutaneously administered TXA127 showed enhanced blood flow (~35%) as compared to vehicle controls. FIG. 9 shows that animals receiving a continuous infusion of TXA127 via Alzet pump also showed enhanced (~30%) blood flow as compared to vehicle controls.

Second Phase of Study—Treatment of Stroke Complications Wherein Treatment is Initiated Seven Weeks after Stroke Event In the second phase of this Example, starting on Day 51, 24 hours post-cerebral blood flow measurement, 10 animals from the control group of the first phase received 500 ug/kg of subcutaneously administered TXA127 daily for 28 days, while 4 of the remaining control mice were treated only with vehicle. Behavioral tests were performed up to 50 days post start of this phase (for a total of 100 days). The second phase of this Example shows that administration of an angiotensin (1-7) peptide, even weeks after a stroke event, is still able to provide significant therapeutic benefit.

Figure 10:
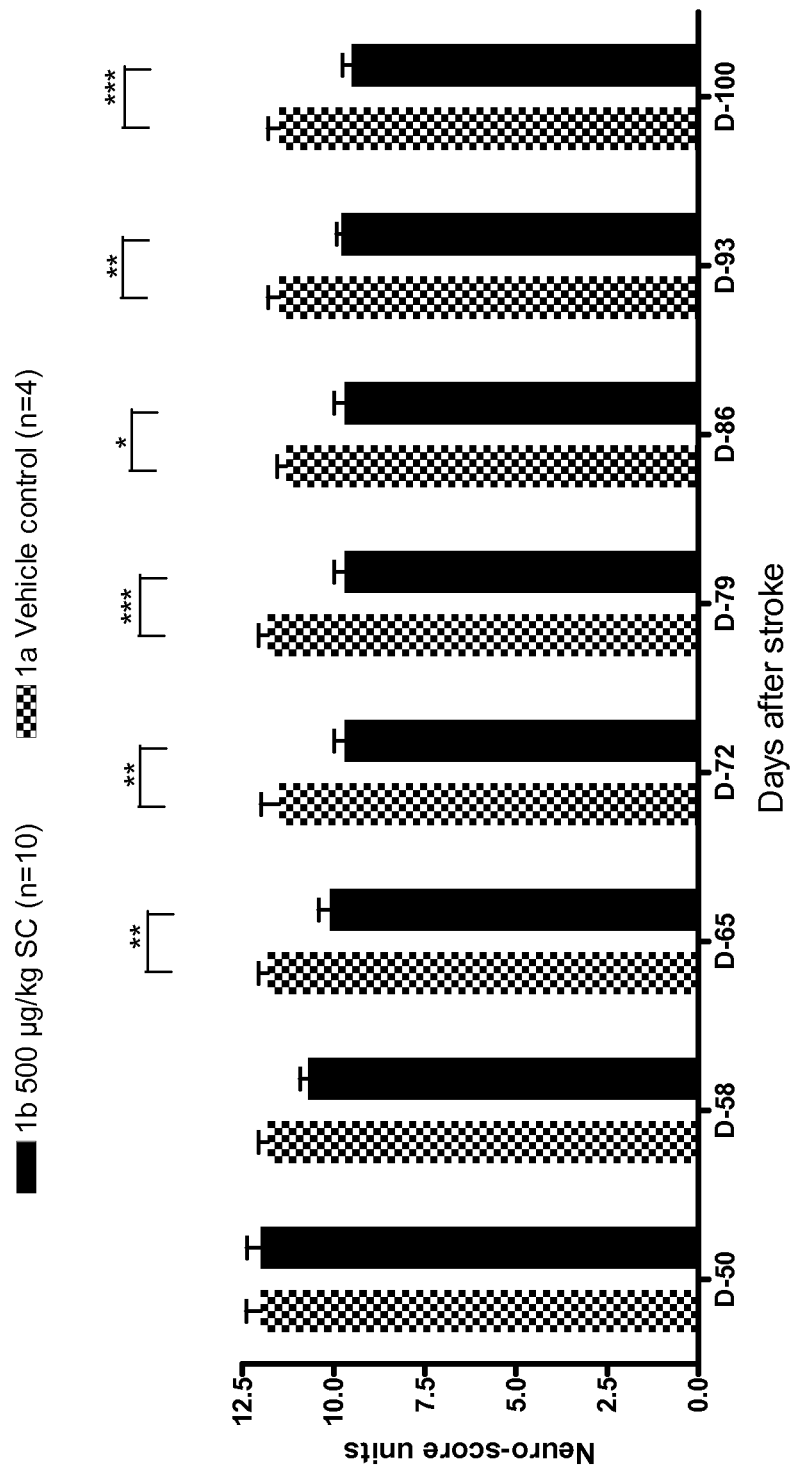
FIG. 10 shows exemplary neuroscores from rats exposed to either vehicle or 500 μg/kg TXA127 (SEQ ID NO: 1) for seven weeks, beginning seven weeks after a tMCAO event.

FIG. 10 shows the neuroscores from animals used in this phase of the Example. Even though animals in the treatment group did not receive a first treatment with TXA127 until day 51 after the stroke event, but day 65 (14 days after the initiation of treatment), there was statistically significant improvement observed in the treatment group as compared to the vehicle control animals.

Figure 11:
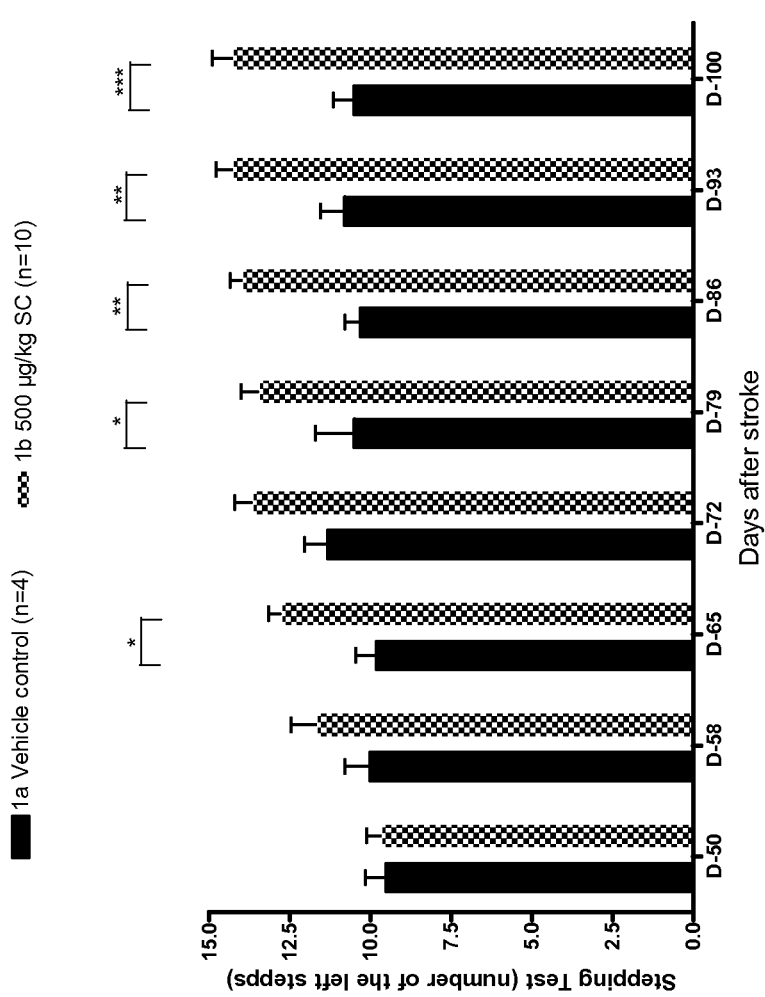
FIG. 11 shows exemplary results in a stepping test from exposed to either vehicle or 500 μg/kg TXA127 (SEQ ID NO: 1) for seven weeks, beginning seven weeks after a tMCAO event.

The results of the stepping test are shown in FIG. 11. Much like the neuroscore results above, a statistically significant improvement in performance was observed in the treatment group by day 65 as compared to the vehicle control group. By day 86 (35 days after the initiation of treatment with TXA127), the degree of improvement versus the control group showed increasing significance.

Figure 12:
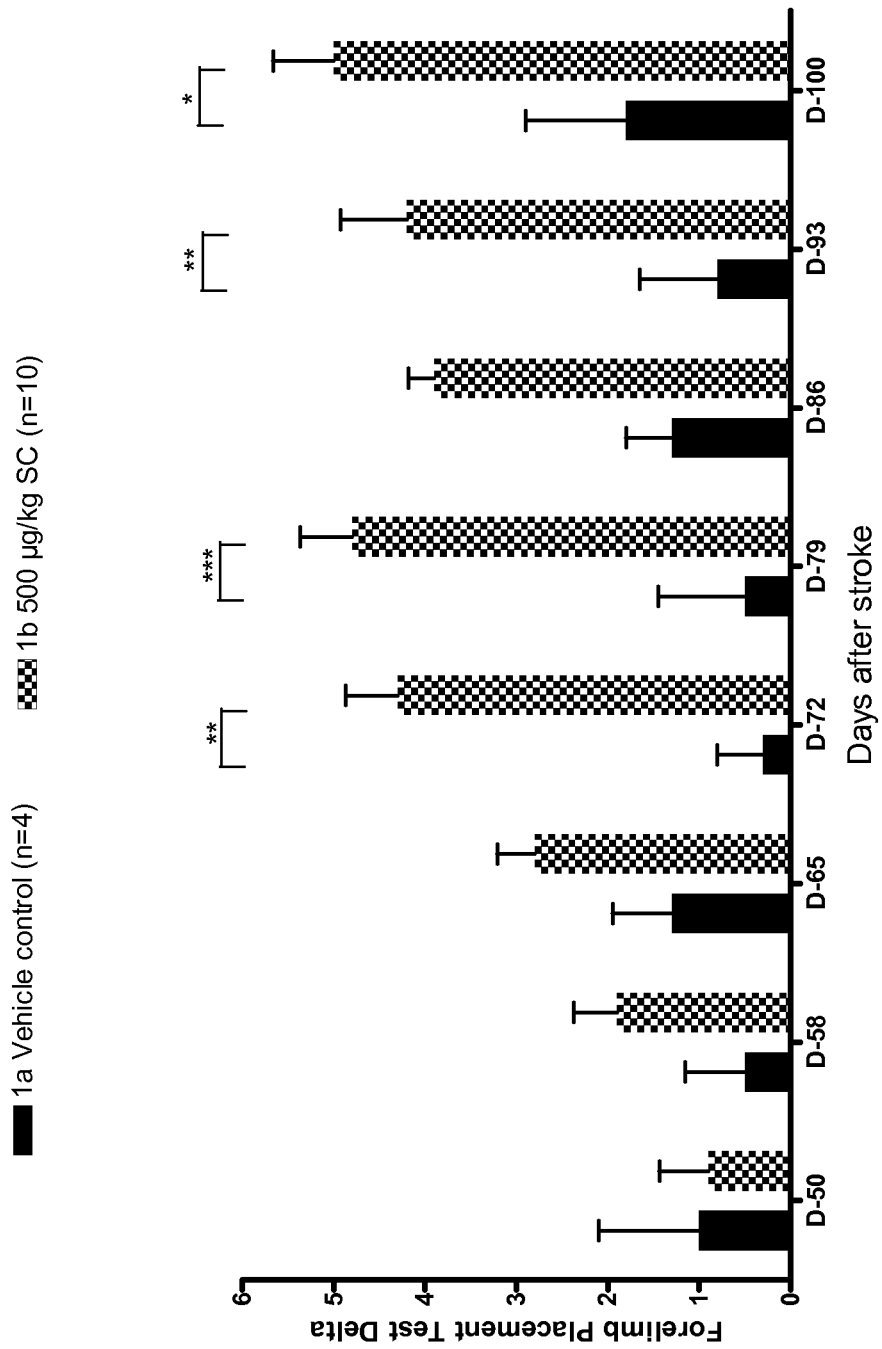
FIG. 12 shows exemplary results from a forelimb placement test from rats exposed to either vehicle or 500 μg/kg TXA127 (SEQ ID NO: 1) for seven weeks, beginning seven weeks after a tMCAO event.

FIG. 12 shows the results of a forelimb placement test. While the data shows a trend toward improvement as early as day 58, statistically significant improvement in performance occurred beginning on day 72.

Figure 13:
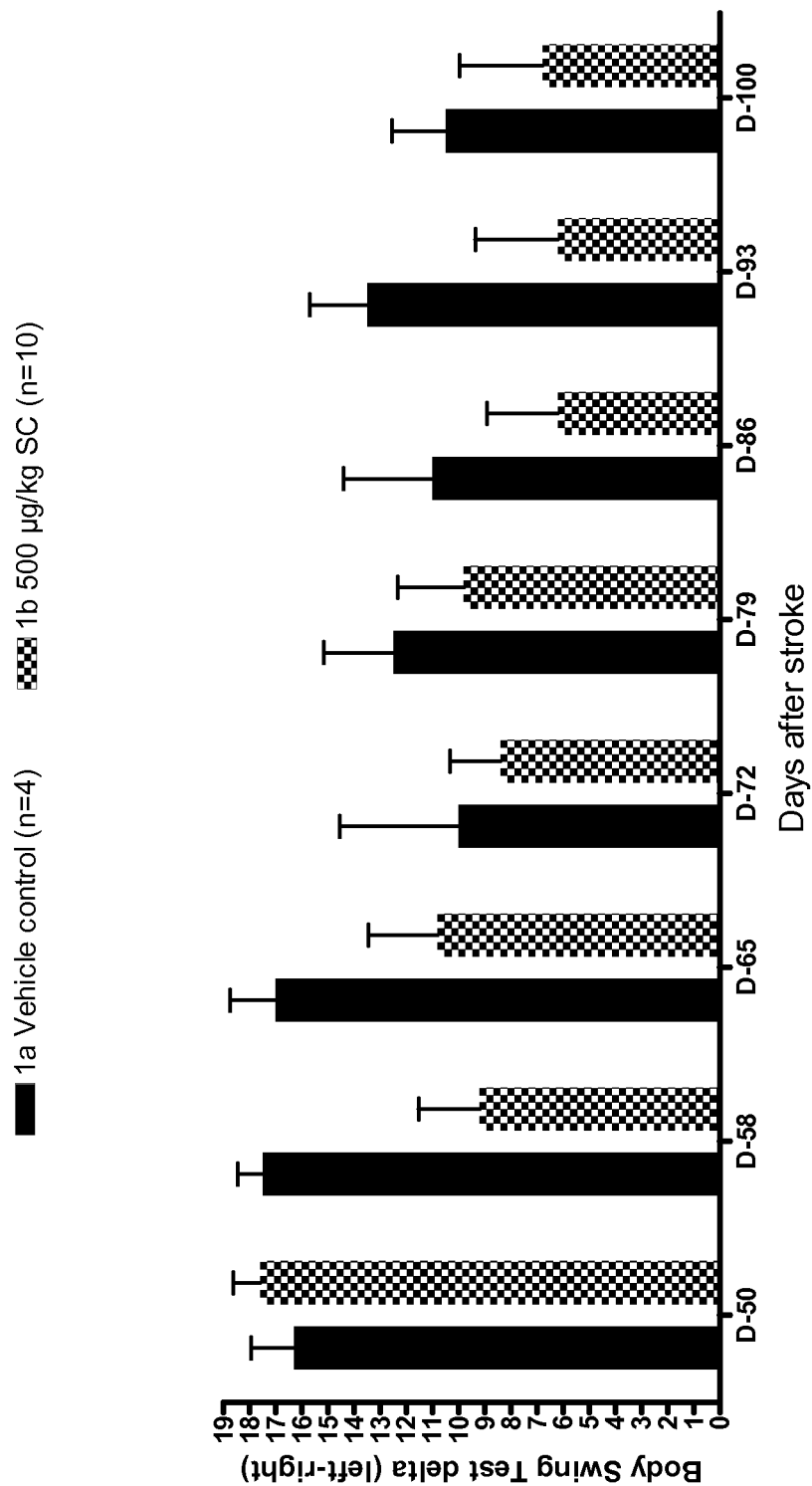
FIG. 13 shows exemplary results from a body swing test form rats exposed to either vehicle or 500 μg/kg TXA127 (SEQ ID NO: 1) for seven weeks, beginning seven weeks after a tMCAO event.

The results of the body swing test are shown in FIG. 13. A trend toward improved performance is observed as early as day 58 and was maintained throughout the rest of the observation period.

Figure 14:
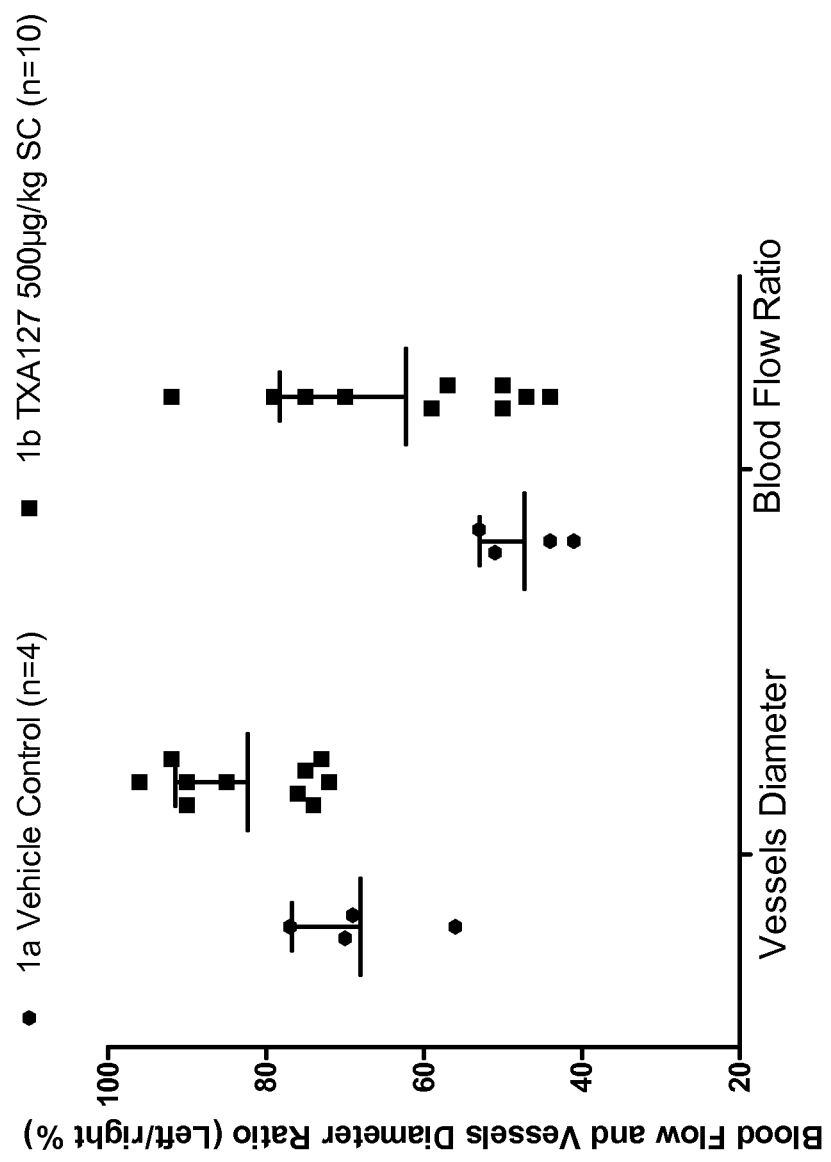
FIG. 14 shows an exemplary comparison of average blood vessel diameter and blood flow ratio between rats exposed to vehicle and rats exposed to 500 μg/kg TXA127 (SEQ ID NO: 1) for eight weeks, beginning seven weeks after a tMCAO event.

Blood vessel diameter and blood flow ratio was measured in all animals at the beginning of the second phase of the study on day 51, and again after the final behavioral test was concluded, on day 108. FIG. 14 shows that both the vessel diameter and blood flow ratio of animals in the treatment groups was improved as compared to animals in the vehicle control group.

This Example shows, among other things, that administration of an angiotensin (1-7) peptide well after a stroke event, whether it is 24 hours or 7 weeks, results in improved outcomes after stroke. To our knowledge, these results represent the first time a therapeutic has been shown to have significant effects on stroke recovery when the first administration is made at least a day after the event. Accordingly, angiotensin (1-7) peptides provide powerful and previously unknown treatment regimen for use in aiding patients who have suffered one or more stroke events.

Example 2

Delayed Treatment of Stroke with TXA302 (SEQ ID NO: 3)

In this Example the angiotensin (1-7) peptide TXA302 (SEQ ID NO: 3) was used in the rat Transient Middle Cerebral Artery Occlusion (tMCAO) model of stroke to determine the effects of this peptide weeks after a stroke event.

In this Example, a total of 30 Sprague Dawley rats were used, evenly split into two groups with 15 rats in each. Each rat was approximately 3 months old and weighed approximately 300 grams±20% at the initiation of the study.

As in Example 1 above, animal handling was performed according to the guidelines of the National Institutes of Health (NIH) and the Association for the Assessment and Accreditation of Laboratory Animal Care (AAALAC). Animals were fed ad libitum a commercial rodent diet, had free access to drinking water, and were housed under standard laboratory conditions with a 12 hour light/dark cycle.

In this Example, the day of the tMCAO procedure is defined as "Day 1" of the study and the tMCAO procedure was performed as described above in Example 1.

TXA302 dose volume was 0.5 ml/kg for daily injections. TXA302 was dissolved in phosphate buffered saline (PBS) to a concentration of 25 mg/ml (stock solution). On the day of injection, the stock solution was further diluted with PBS to a concentration of 0.1 mg/ml for a dose level of 50 µg/kg.

As in Example 1, animals were subjected to the mNSS test (Neuroscore) at Day 2, 24 hours post reperfusion. Only animals with an overall score of ≥10 were included in this Example.

Beginning on day 29 (28 days post-tMCAO procedure), animals were treated daily with a subcutaneous injection of either a saline solution (vehicle control animals) or 50 µg/kg TXA302. Table 2 shows the group design used in this Example.

TABLE 2

Group Allocation

| Group | Treatment | Dose | Administration | Treatment Duration (days) | N |
|---|---|---|---|---|---|
| 1 | Vehicle | 0 | SC | 42 | 15 |
| 2 | TXA302 | 50 µg/kg | SC | 42 | 15 |

Neurological Scoring (Pre-Operation, and Day 2, 29, 43, 50, 57, 64 and 71)

As in Example 1, each animal was subjected to a neuroscore test. The Modified Neurological Rating Scale (mNRS), or Neuroscore, was performed before the operation as described in Example 1 on day 2, day 29, day 43, day 50, day 57, day 64 and day 71. The individual making the behavioral assessments was unaware of the drug/dose given (blind test).

Figure 15:
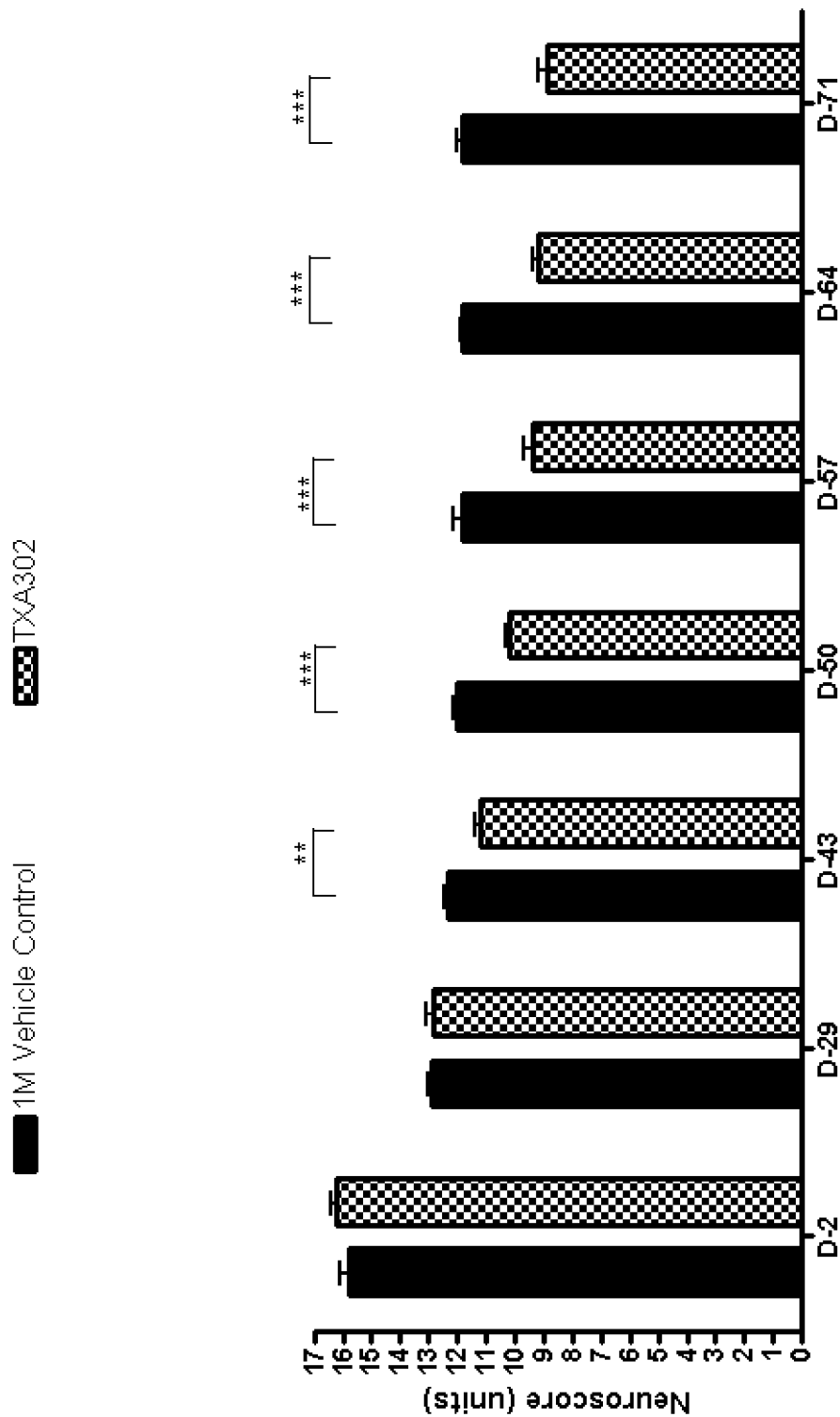
FIG. 15 shows exemplary neuroscores from rats exposed to either vehicle or 50 μg/kg TXA302 (SEQ ID NO: 3) for six weeks, beginning four weeks after a tMCAO event.

As shown in FIG. 15, by day 43, animals receiving TXA302 showed a statistically significant reduction in neuroscore as compared to vehicle control animals, which progressively improved between days 43 and 57, and this effect was at least maintained through day 71.

Stepping Test (Pre-Operation, and Day 29, 43, 50, 57, 64 and 71)

Animals were also tested for forelimb akinesia in a stepping test (ST) as described in Example 1 on days 29, 43, 50, 57, 64 and 71.

Figure 16:
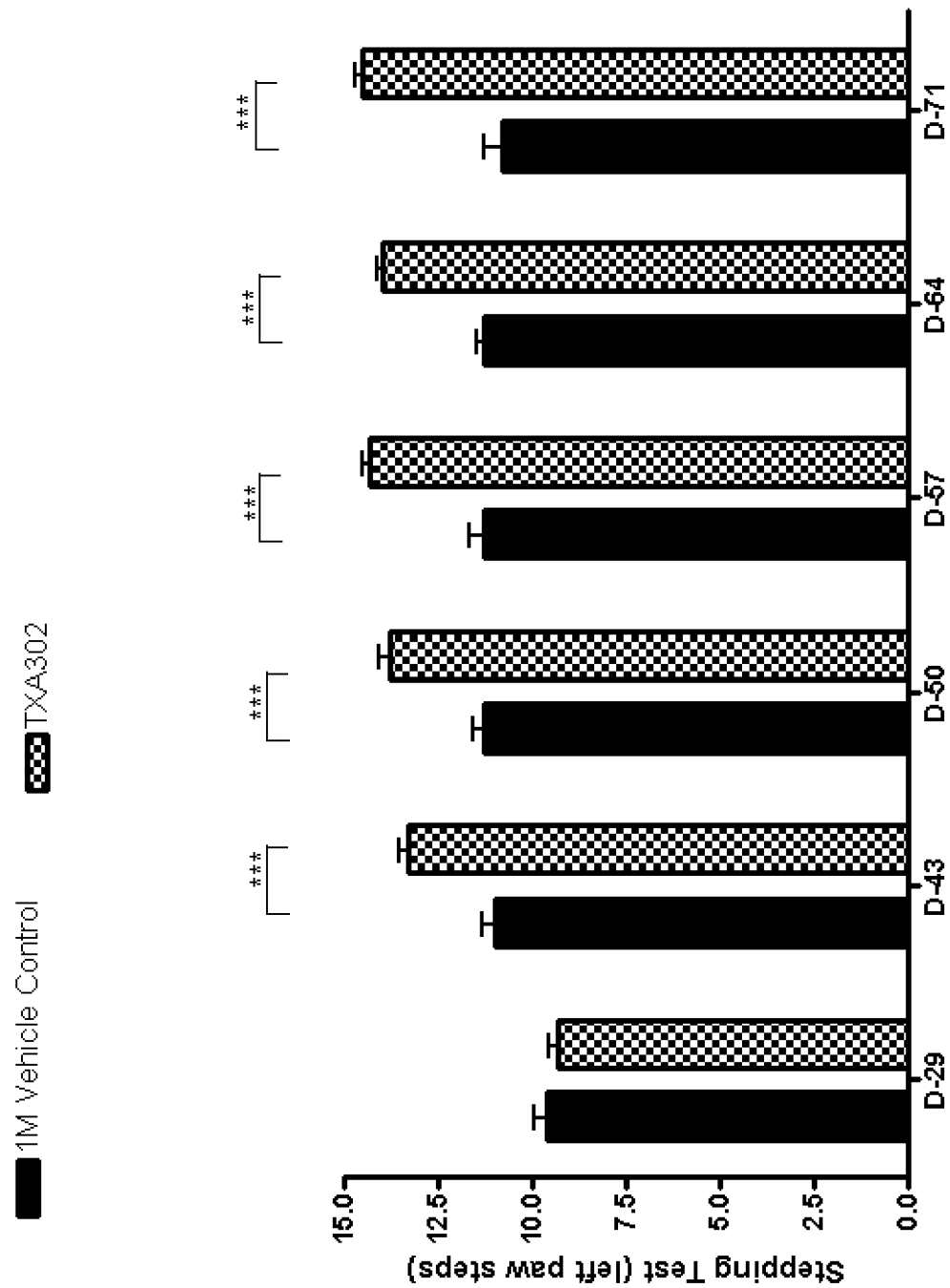
FIG. 16 shows exemplary results in a stepping test from rats exposed to either vehicle or 50 µg/kg TXA302 (SEQ ID NO: 3) for six weeks, beginning four weeks after a tMCAO event.

FIG. 16 shows that administration of TXA302 provided a significant improvement in performance in the stepping test by day 43, as compared to vehicle control animals. This effect was maintained through Day 71.

Limb Placement Test (Pre-Operation, and Day 29, 43, 50, 57, 64 and 71)

Animals were also subjected to a limb placement test as described in Example 1 on days 29, 43, 50, 57, 64 and 71.

Figure 17:
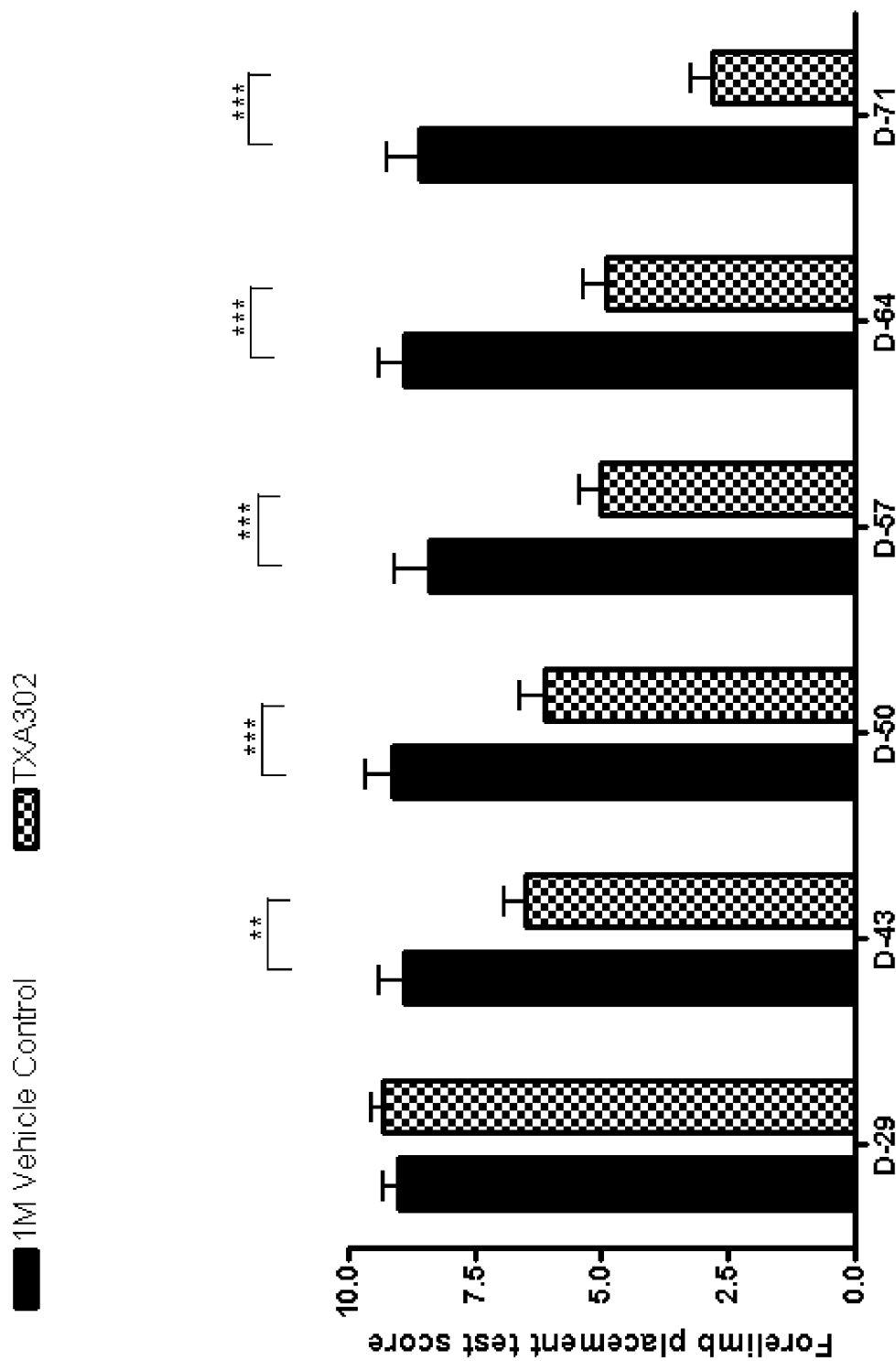
FIG. 17 shows exemplary results from a forelimb placement test from rats exposed to either vehicle or 50 µg/kg TXA302 (SEQ ID NO: 3) for six weeks, beginning four weeks after a tMCAO event.

The results provided in FIG. 17 show that animals treated with TXA302 enjoyed statistically significant improvements in performance by day 43 as compared to vehicle control animals. As with the results of the neuroscore and stepping test assessment, these improvements were maintained or improved further through day 71.

Body Swing Test (Pre-Operation, and Day 29, 43, 50, 57, 64 and 71)

Animals were also subjected to a body swing test as described in Example 1 on days 29, 43, 50, 57, 64 and 71.

Figure 18:
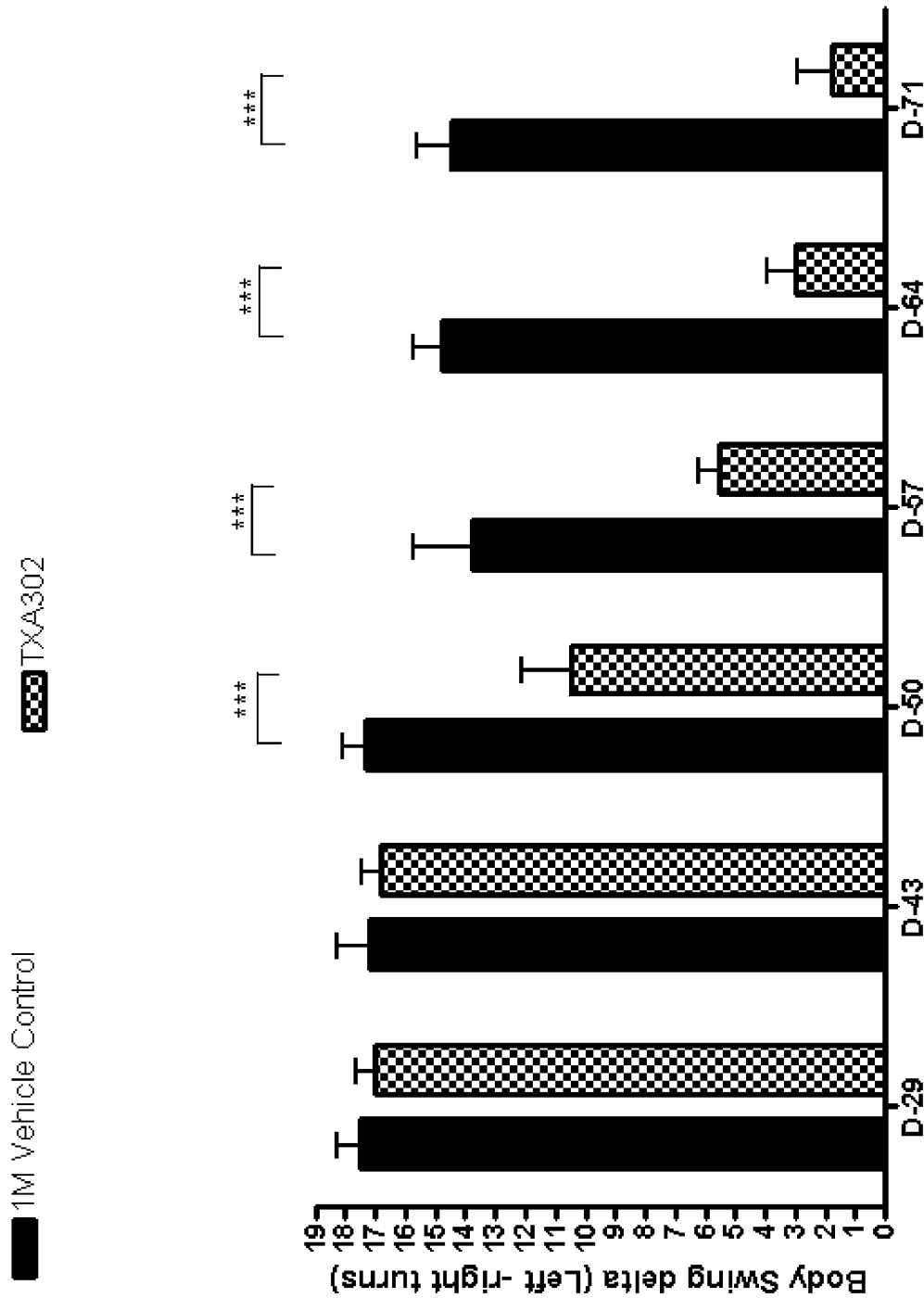
FIG. 18 shows exemplary results from a body swing test from rats exposed to either vehicle or 50 µg/kg TXA302 (SEQ ID NO: 3) for six weeks, beginning four weeks after a tMCAO event.

The results of the body swing test in FIG. 18 show that by day 50 a statistically significant improvement in performance was enjoyed by animals receiving TXA302. As with each of the other tests, improved performance in the TXA302 group was at least maintained through Day 71. Importantly, performance trended toward increasing improvement between days 50 and 71, nearing complete recovery of function.

Cylinder Test (Day 26 and 57)

Animals were also subjected to a cylinder test of motor function on days 26 and 57. The cylinder test is a well-known and accepted assessment of motor function and can aid in the determination of forelimb akinesia among other neurological deficits that may result from stroke. The cylinder test takes advantage of the rat's innate drive to explore a novel environment by standing on its hind limbs and leaning toward enclosed walls.

In this Example, animals were placed in a transparent cylinder (21 cm diameter and 34 cm height) for 5 minutes. A camera was placed adjacent to the cylinder to allow for remote monitoring of the results of the test, and a mirror was placed behind the cylinder at an angle to permit recording of forelimb movements whenever the animal was turned away from the camera. In this Example, the cylinder was tall enough that the animal could not reach the top edge by rearing and wide enough to permit a 2 cm space between the tip of the snout and the base of the tail when the animal was not rearing. No habituation to the cylinder was allowed prior to observation. If an animal did not exhibit exploratory behavior, animals were stimulated via one or more of: a) turning the lights in the room on and off 2-3 times, b) mildly shaking the cylinder for 2-3 seconds, or c) taking the animal out of the cylinder for 30 seconds and then putting it back in.

The number of wall contacts performed independently with the left and right forepaw were counted and noted up to a total of 20 wall contacts per animal per session, and only supporting contacts were counted (i.e., full appositions of the paws with open digits to the cylinder walls). Generally, a healthy animal will exhibit approximately equal left and right paw contacts with the cylinder. The ratio of left paw to right paw placements was recorded and presented in FIG. 19 as a ratio of (left contacts/right contacts)*100 (e.g., an animal exhibiting equal left/right placements would have a ratio of (1/1)*100=100, while an animal exhibiting twice as many right paw contacts as left paw contacts would have a ration of (1/2)*100=50).

Figure 19:
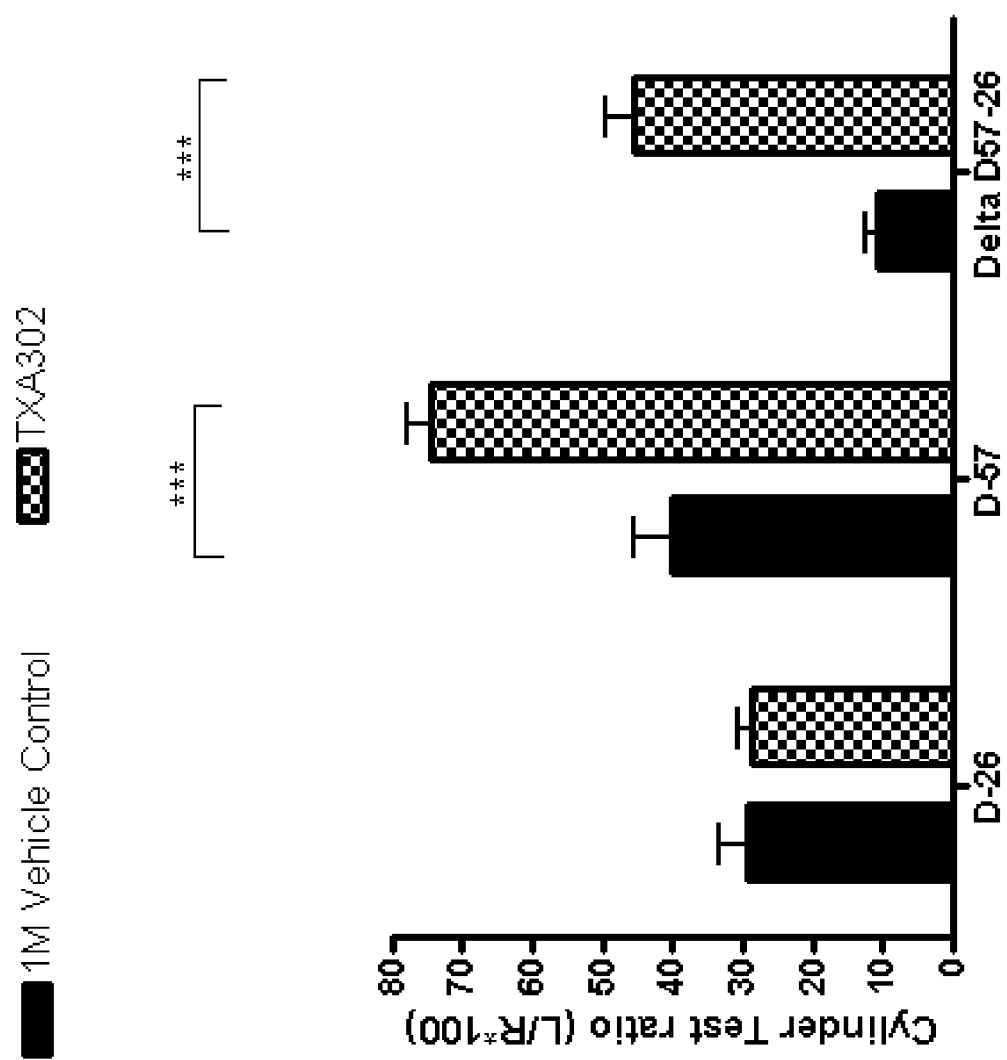
FIG. 19 shows exemplary results from a cylinder test of motor function from rats exposed to either vehicle or 50 µg/kg TXA302 (SEQ ID NO: 3) for four weeks, beginning four weeks after a tMCAO event.

As shown in FIG. 19, on day 26 all tested animals exhibited approximately three times as many right paw contacts as left paw contacts (ratio of ~0.3). By day 57, however, animals in the vehicle control condition exhibited a slight improvement over day 26 results (ratio ~0.4), while animals in the TXA302 condition exhibited a dramatic and statistically significant improvement in performance of nearly twice the improvement exhibited by vehicle control animals (ratio ~0.75).

This Example shows, among other things, that administration of TXA302 well after a stroke event, here 4 weeks, results in significantly improved outcomes after stroke. It is of particular note that in some functional assessments, improvement in performance appears to increase over time as angiotensin (1-7) peptides are administered. These results further support the previously unknown use of Angiotensin (1-7) peptides in the delayed treatment of stroke, even commencing weeks after a stroke event. Accordingly, angiotensin (1-7) peptides including TXA127 and TXA302 provide powerful and previously unknown treatment regimen for use in aiding patients who have suffered one or more stroke events.

Example 3

Delayed Treatment of Stroke with TXA127 (SEQ ID NO: 1) or TXA302 (SEQ ID NO: 3)

In this Example, two angiotensin (1-7) peptides, namely, TXA127 (SEQ ID NO: 1) and TXA302 (SEQ ID NO: 3) were used in the rat Transient Middle Cerebral Artery Occlusion (tMCAO) model of stroke to establish dose responses and to determine the comparative effects of these peptides when administration first begins four weeks after a stroke event.

In this Example, a total of 120 Sprague Dawley rats were used, evenly split into eight groups with 15 rats in each. Each rat was approximately 3 months old and weighed approximately 300 grams±20% at the initiation of the study.

As in Examples 1 and 2 above, animal handling was performed according to the guidelines of the National Institutes of Health (NIH) and the Association for the Assessment and Accreditation of Laboratory Animal Care (AAALAC). Animals were fed ad libitum a commercial rodent diet, had free access to drinking water, and were housed under standard laboratory conditions with a 12 hour light/dark cycle.

In this Example, the day of the tMCAO procedure is defined as "Day 1" of the study and the tMCAO procedure was performed as described above in Example 1.

The dose volume of both TXA 127 and TXA302 was 0.5 ml/kg for daily injections. TXA127 was diluted in phosphate buffered saline (PBS) at a concentration of 2 mg/ml for a dose level of 1,000 μg/kg; at a concentration of 1 mg/ml for dose level 500 μg/kg and at a concentration of 0.2 mg/ml for dose level 100 μg/kg. TXA302 was dissolved in PBS to a concentration of 1 mg/ml for dose level 500 μg/kg, at a concentration of 0.01 mg/ml for dose level 5 μg/kg, and at a concentration of 0.002 mg/ml for dose level 1 μg/kg.

As in Example 1, animals were subjected to the mNSS test (Neuroscore) at Day 2, 24 hours post reperfusion. Only animals with an overall score of ≥10 were included in this Example.

Beginning on day 29 (28 days post-tMCAO procedure), animals were treated daily with a subcutaneous injection of one of: vehicle, 100 μg/kg TXA127 (SEQ ID NO: 1), 500 μg/kg TXA127, 1,000 μg/kg TXA127, 1μg/kg TXA302 (SEQ ID NO: 3), 5 μg/kg TXA302, 50 μg/kg TXA302, or 500 μg/kg TXA302 given subcutaneously for up to eight weeks, beginning four weeks after a tMCAO event. Table 3 shows the group design used in this Example.

TABLE 3

| Group Allocation | | | | | |
|---|---|---|---|---|---|
| Group | Treatment | Dose | Administration | Treatment Duration (days) | Total Rats |
| 1 | Vehicle | 0 | SC | 56 | 15 |
| 2 | TXA127 | 100 μg/kg | SC | 56 | 15 |
| 3 | TXA127 | 500 μg/kg | SC | 56 | 15 |
| 4 | TXA127 | 1,000 μg/kg | SC | 56 | 15 |
| 5 | TXA302 | 1 μg/kg | SC | 56 | 15 |
| 6 | TXA302 | 5 μg/kg | SC | 56 | 15 |
| 7 | TXA302 | 500 μg/kg | SC | 56 | 15 |
| 8 | TXA302 | 500 μg/kg | SC | 56 | 15 |

Neurological Scoring (Pre-Operation, and Day 2, 29, 43, 50, 57, 64, 71, 78 and 85)

As in Examples 1 and 2, each animal was subjected to a neuroscore test. The Modified Neurological Rating Scale (mNRS), or Neuroscore, was performed before the operation as described in Example 1 on day 2, day 29, day 43, day 50, day 57, day 64, day 71. Day 78, and day 85. The individual making the behavioral assessments was unaware of the drug/dose given (blind test).

Figure 20:
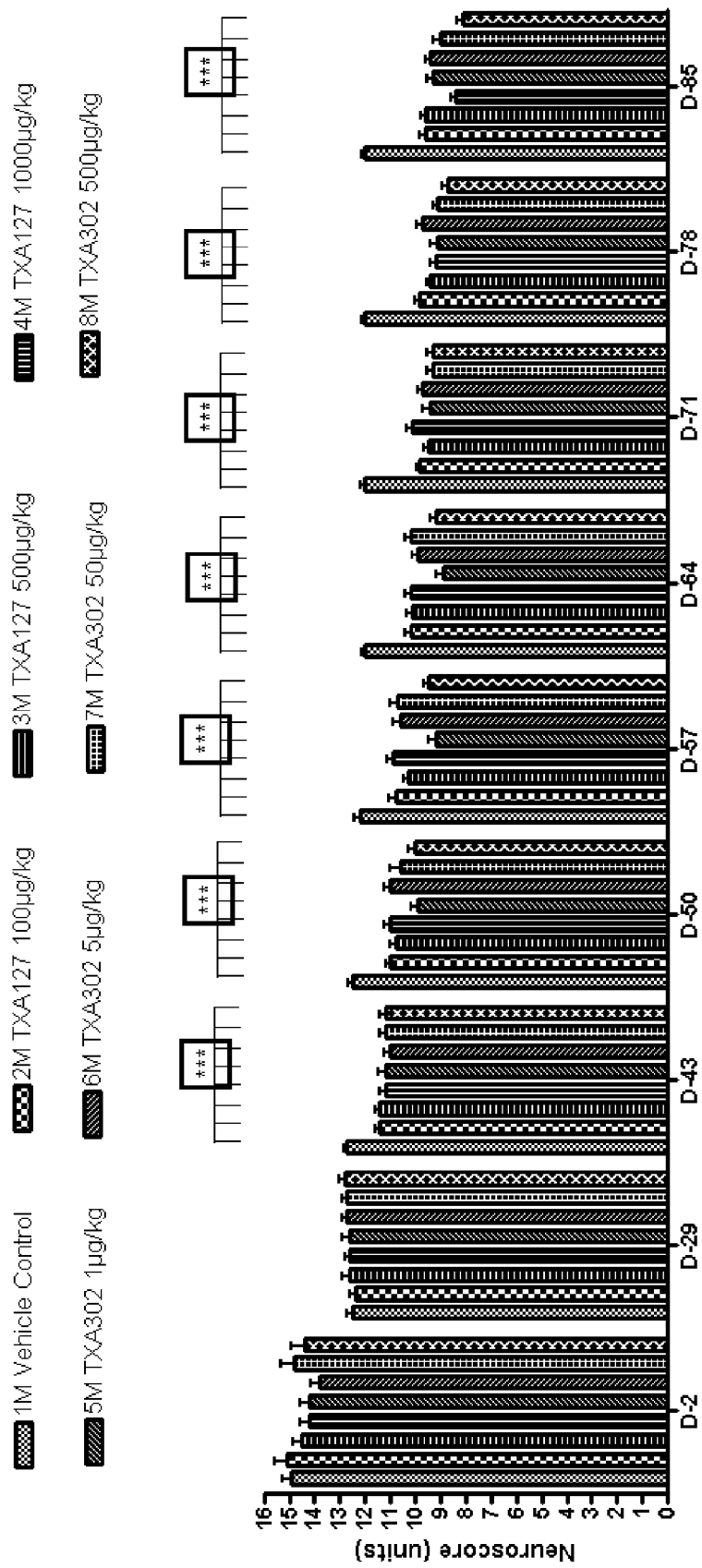
FIG. 20 shows exemplary neuroscores from rats exposed to one of: vehicle, 100 µg/kg TXA127 (SEQ ID NO: 1), 500 µg/kg TXA127, 1,000 µg/kg TXA127, 1,000 µg/kg TXA302 (SEQ ID NO: 3), 5 µg/kg TXA302, 50 µg/kg TXA302, or 500 µg/kg TXA302 given subcutaneously for up to eight weeks, beginning four weeks after a tMCAO event.

As shown in FIG. 20, by day 43, animals receiving either TXA127 or TXA302 showed a statistically significant reduction in neuroscore as compared to vehicle control animals, which progressively improved between days 43 and 64, and this effect was at least maintained through day 85.

Stepping Test (Pre-Operation, and Day 29, 43, 50, 57, 64, 71, 78 and 85)

Animals were also tested for forelimb akinesia in a stepping test (ST) as described in Example 1 on days 29, 43, 50, 57, 64, 71, 78 and 85.

Figure 21:
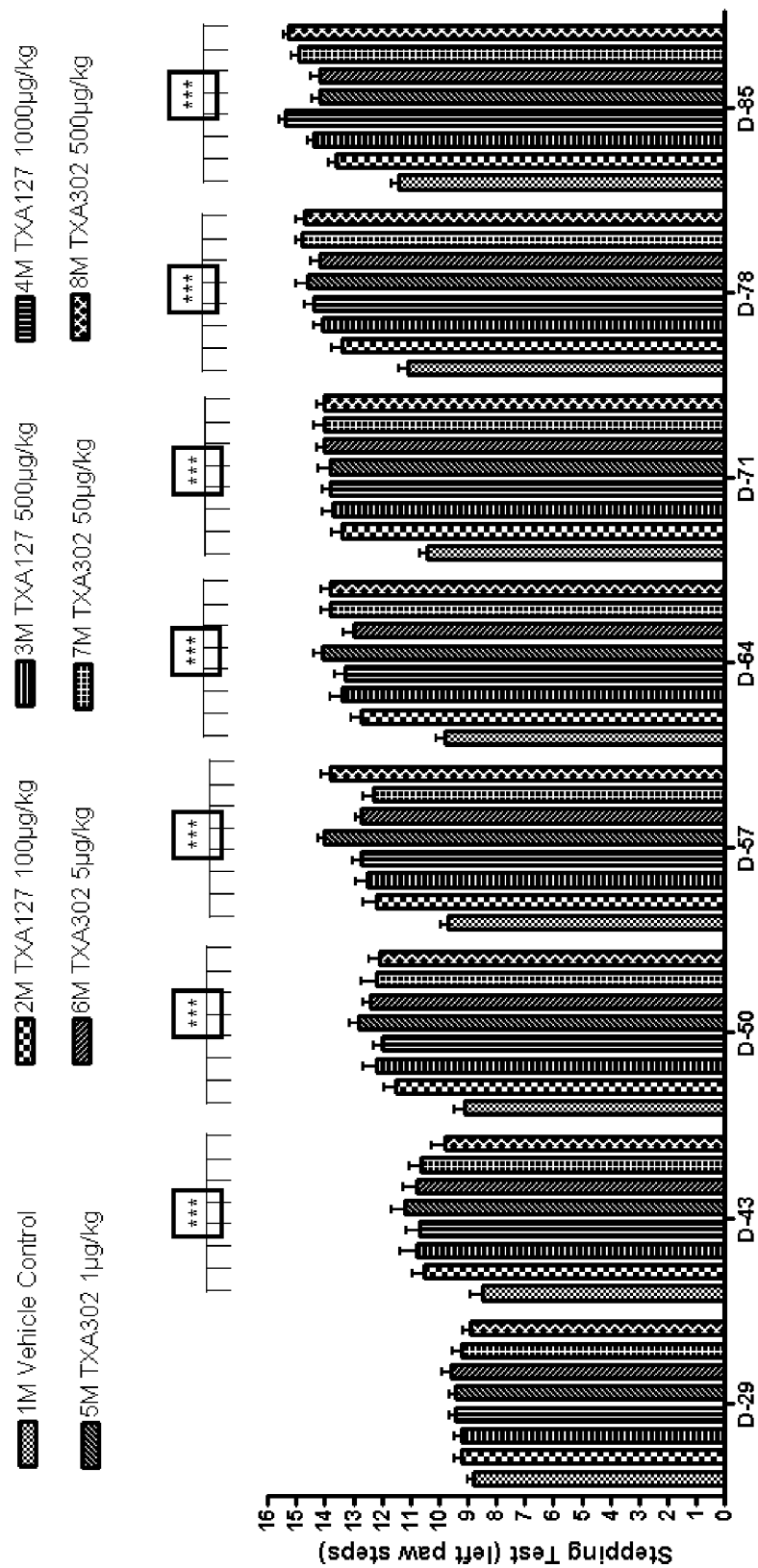
FIG. 21 shows exemplary results in a stepping test from rats exposed to one of: vehicle, 100 µg/kg TXA127 (SEQ ID NO: 1), 500 µg.kg TXA127, 1,000 µg/kg TXA127, 1 µg/kg TXA302 (SEQ ID NO: 3), 5 µg/kg TXA302, 50 µg/kg TXA302, or 500 µg/kg TXA302 given subcutaneously for up to eight weeks, beginning four weeks after a tMCAO event.

FIG. 21 shows that administration of either TXA127 or TXA302 provided a significant improvement in performance in the stepping test by day 43, as compared to vehicle control animals. This effect was maintained through Day 85.

Limb Placement Test (Pre-Operation, and Day 29, 43, 50, 57, 64, 71, 78, and 85)

Animals were also subjected to a limb placement test as described in Example 1 on days 29, 43, 50, 57, 64, 71, 78 and 85.

Figure 22:
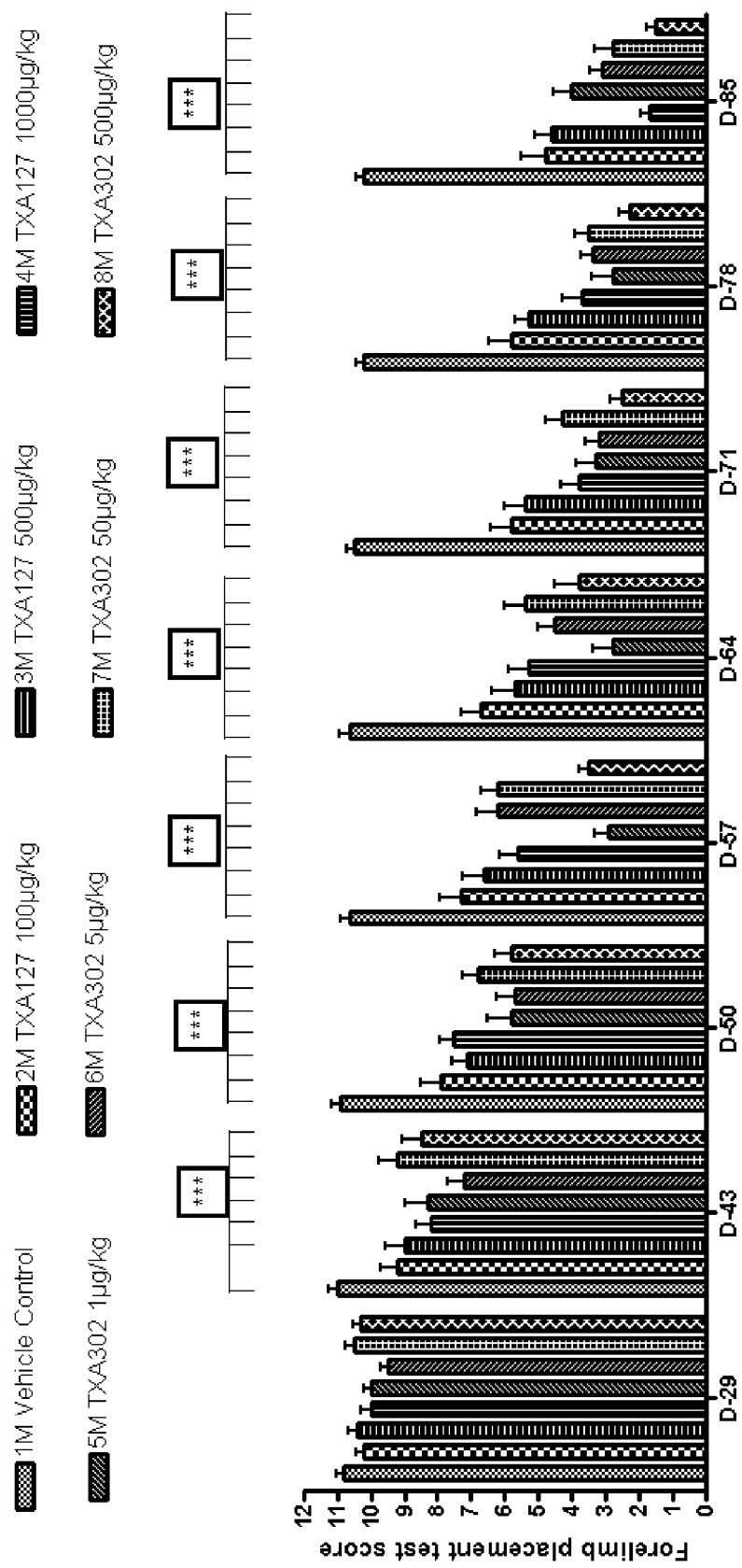
FIG. 22 shows exemplary results from a forelimb placement test from rats exposed to one of: vehicle, 100 µg/kg TXA127 (SEQ ID NO: 1), 500 µg/kg TXA127, 1,000 µg/kg TXA127, 1 µg/kg TXA302 (SEQ ID NO: 3), 5 µg/kg TXA302, 50 µg/kg TXA302, or 500 µg/kg TXA302 given subcutaneously for up to eight weeks, beginning four weeks after a tMCAO event.

The results provided in FIG. 22 show that animals treated with either TXA127 or TXA302 enjoyed statistically significant improvements in performance by day 43 as compared to vehicle control animals. As with the results of the neuroscore and stepping test assessment, these improvements were maintained or improved further through day 85.

Body Swing Test (Pre-Operation, and Day 29, 43, 50, 57, 64, 71, 78 and 85)

Animals were also subjected to a body swing test as described in Example 1 on days 29, 43, 50, 57, 64, 71, 78 and 85.

Figure 23:
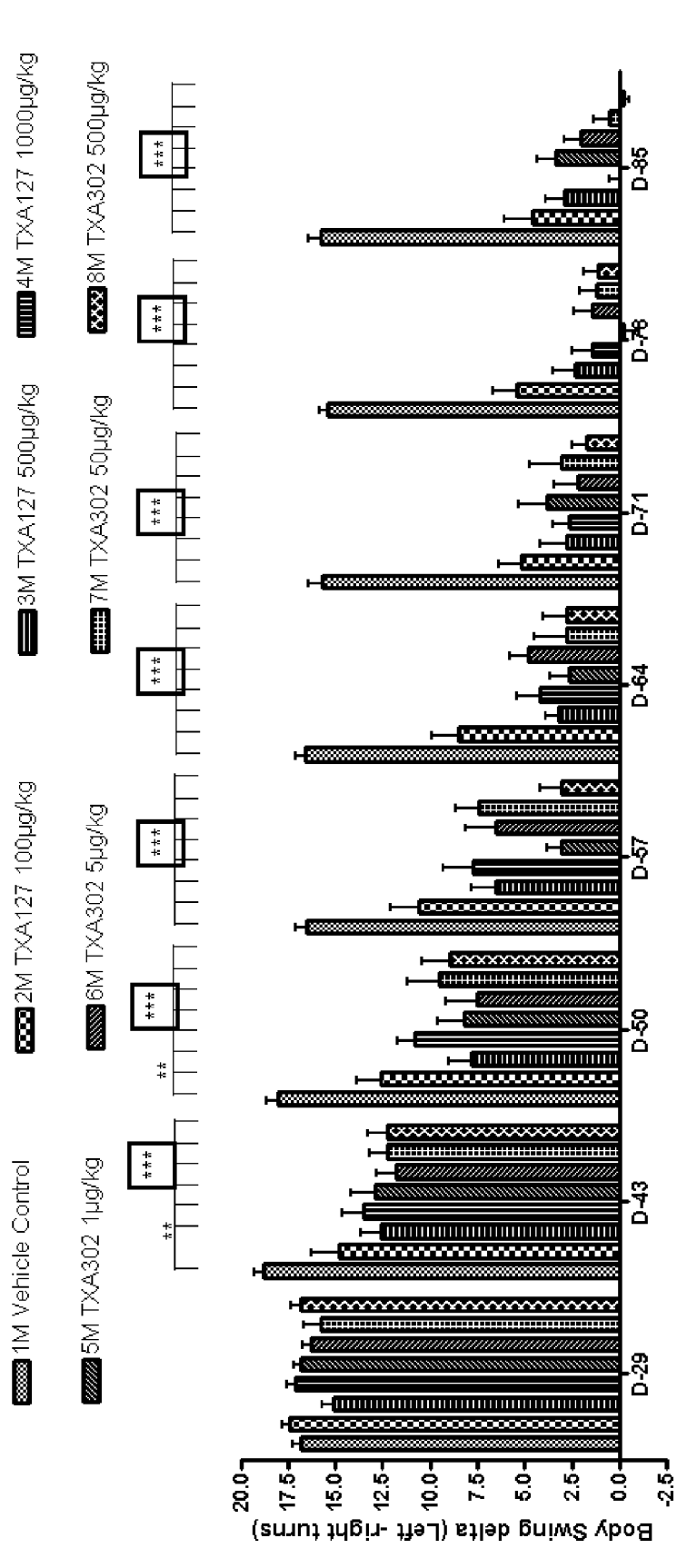
FIG. 23 shows exemplary results from a body swing test from rats exposed to one of: vehicle, 100 µg/kg TXA127 (SEQ ID NO: 1), 500 µg/kg TXA127, 1,000 µg/kg TXA127, 1 µg/kg TXA302 (SEQ ID NO: 3), 5 µg/kg TXA302, 50 µg/kg TXA302, or 500 µg/kg TXA302 given subcutaneously for up to eight weeks, beginning four weeks after a tMCAO event.

The results of the body swing test in FIG. 23 show that by day 43 a statistically significant improvement in performance was enjoyed by animals receiving either TXA127 or TXA302. As with each of the other tests, improved performance in the TXA302 group was at least maintained through Day 85. As in Example 2, performance trended toward increasing improvement between days 50 and 78, nearing or in some cases achieving substantially complete recovery of function.

Blood Flow Ratio and Blood Vessel Diameter (Day 86)

Figure 24:
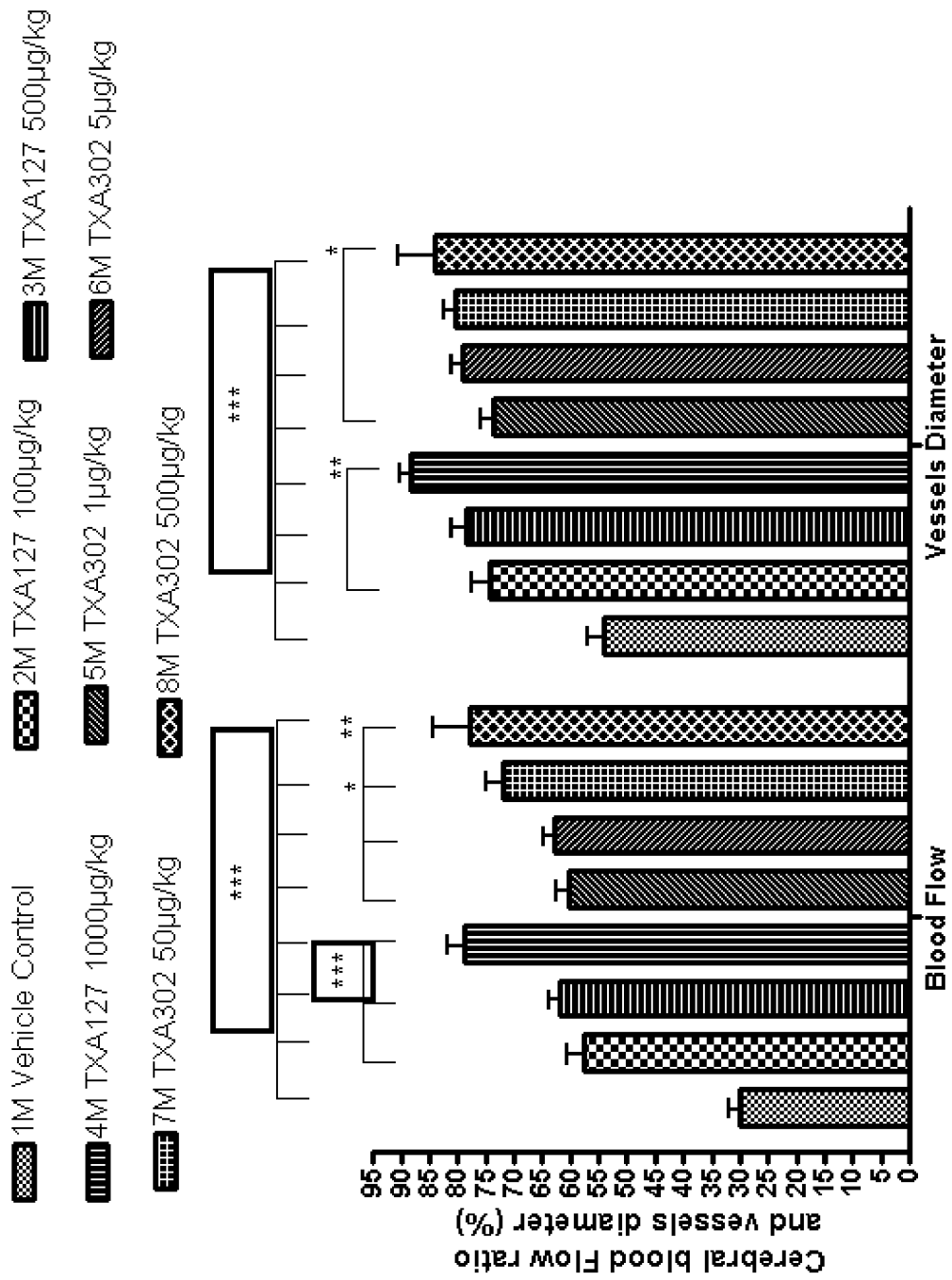
FIG. 24 shows an exemplary comparison of average blood flow ratio and blood vessel diameter between rats exposed to one of: vehicle, 100 µg/kg TXA127 (SEQ ID NO: 1), 500 µg/kg TXA127, 1,000 µg/kg TXA127, 1 µg/kg TXA302 (SEQ ID NO: 3), 5 µg/kg TXA302, 50 µg/kg TXA302, or 500 µg/kg TXA302 given subcutaneously for up to eight weeks, beginning four weeks after a tMCAO event.

Blood flow ratio and blood vessel diameter were measured as described in Example 1 in all animals on day 86. FIG. 24 shows that both the vessel diameter and blood flow ratio of animals in the treatment groups was significantly improved as compared to animals in the vehicle control group.

This Example shows, among other things, that angiotensin (1-7) peptides are effective at treating a variety of stroke-related complications when administered several weeks after a stroke event, at doses spanning at least one order of magnitude. Specifically, administration of either TXA127 at doses between 100 µg/kg and 1,000 µg/kg, or TXA302 at doses between 1 µg/kg and 500 µg/kg for up to eight weeks resulted in statistically significant improvement in several physical, cognitive, and physiological measures of function as compared to vehicle control animals at all doses tested. When compared to previously known therapies, which were effective in treating stroke-related complications only is administered within hours after a stroke event, angiotensin (1-7) peptides represent a powerful and effective new class of therapies for the treatment of stroke and stroke-related complications.

EQUIVALENTS AND SCOPE

Those skilled in the art will recognize, or be able to ascertain using no more than routine experimentation, many equivalents to the specific embodiments of the invention described herein.

I claim:

1. A method of alleviating, ameliorating, relieving, inhibiting, delaying onset of, reducing the severity of or reducing the incidence of stroke comprising
administering an angiotensin (1-7) peptide to a subject suffering from a stroke via systemic administration, wherein the systemic administration is not intracerebroventricular administration, wherein the first administration of the angiotensin (1-7) peptide starts at least 24 hours following the stroke, and wherein the angiotensin (1-7) peptide is administered without the use of modified stem cells.

2. The method of claim 1, wherein the angiotensin (1-7) peptide is administered at least 25 hours, 30 hours, 36 hours, 42 hours, 48 hours, 72 hours, 96 hours, or 120 hours following the stroke.

3. The method of claim 1, wherein the angiotensin (1-7) peptide is administered at least 1 week, 2 weeks, 3 weeks, 4 weeks, 5, weeks, 6 weeks, or 7 weeks following the stroke.

4. The method of claim 1, wherein the step of administering the angiotensin (1-7) peptide is the first treatment of stroke in the subject.

5. The method of claim 1, wherein the step of administering the angiotensin (1-7) peptide is conducted subsequent to a prior treatment of stroke in the subject.

6. The method of claim 5, wherein the prior treatment of stroke takes place within 3 hours.

7. The method of claim 5, wherein the prior treatment of stroke takes place within 12 hours.

8. The method of claim 1, wherein the systemic administration is oral administration.

9. The method of claim 1, wherein the systemic administration is intravenous administration.

10. The method of claim 1, wherein the angiotensin (1-7) peptide is administered at an effective dose ranging from about 1-1,000 μg/kg/day.

11. The method of claim 1, wherein the angiotensin (1-7) peptide is administered at an effective dose ranging from about 50-500 μg/kg/day.

12. The method of claim 1, wherein the angiotensin (1-7) peptide is administered at an effective dose ranging from about 1-60 μg/kg/day.

13. The method of claim 1, wherein the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO: 1).

14. The method of claim 1, wherein the angiotensin (1-7) peptide is a functional equivalent of SEQ ID NO: 1.

15. The method of claim 14, wherein the functional equivalent is a linear peptide.

16. The method of claim 15, wherein the linear peptide comprises a sequence that includes at least four amino acids from the seven amino acids that appear in the naturally-occurring Angiotensin (1-7), wherein the at least four amino acids maintain their relative positions as they appear in the naturally-occurring Angiotensin (1-7).

17. The method of claim 15, wherein the linear peptide contains 4-25 amino acids.

18. The method of claim 15, wherein the linear peptide has an amino acid sequence of $Asp^1$-$Arg^2$-$Val^3$-$Ser^4$-$Ile^5$-$His^6$-$Cys^7$ (SEQ ID NO: 2).

19. The method of claim 15, wherein the linear peptide has an amino acid sequence of $Ala^1$-$Arg^2$-$Val^3$-$Ser^4$-$Ile^5$-$His^6$-$Cys^7$ (SEQ ID NO: 3).

20. The method of claim 14, wherein the angiotensin (1-7) peptide comprises one or more chemical modifications to increase protease resistance, serum stability and/or bioavailability.

21. The method of claim 20, wherein the one or more chemical modifications comprise pegylation.

22. The method of claim 1, wherein the stroke is either ischemic stroke, hemorrhagic stroke, or a combination thereof.

23. The method of claim 1, wherein the administration of angiotensin (1-7) peptide results in a reduction in the intensity, severity, duration, and/or frequency of one or more complications of stroke.

24. The method of claim 23, wherein the one or more complications of stroke is selected from paralysis, memory loss, pain, seizure, dysphagia, aphasia, dysarthria, ataxia, depression, mood swings, and loss of vision.

* * * * *